US012606829B2

(12) United States Patent
Weinberger et al.

(10) Patent No.: US 12,606,829 B2
(45) Date of Patent: Apr. 21, 2026

(54) COMPOSITIONS FOR HERPESVIRUS TRANSCRIPTIONAL FEEDBACK CIRCUIT DISRUPTION AND USES THEREOF

(71) Applicant: The J. David Gladstone Institutes, San Francisco, CA (US)

(72) Inventors: Leor S. Weinberger, Oakland, CA (US); Sonali Chaturvedi, San Francisco, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 421 days.

(21) Appl. No.: 17/251,395

(22) PCT Filed: Jun. 12, 2019

(86) PCT No.: PCT/US2019/036841
§ 371 (c)(1),
(2) Date: Dec. 11, 2020

(87) PCT Pub. No.: WO2019/241435
PCT Pub. Date: Dec. 19, 2019

(65) Prior Publication Data
US 2021/0395746 A1      Dec. 23, 2021

Related U.S. Application Data

(60) Provisional application No. 62/684,099, filed on Jun. 12, 2018.

(51) Int. Cl.
*C12N 15/113*      (2010.01)
*A61K 31/522*      (2006.01)
(Continued)

(52) U.S. Cl.
CPC ........ *C12N 15/1133* (2013.01); *A61K 31/522* (2013.01); *A61K 31/662* (2013.01);
(Continued)

(58) Field of Classification Search
CPC .......... C12N 15/1133; C12N 2310/315; A61K 31/713
See application file for complete search history.

(56) References Cited

U.S. PATENT DOCUMENTS

| | | |
|---|---|---|
| 5,495,006 A | 2/1996 | Climie et al. |
| 7,642,275 B2 | 1/2010 | Bressi et al. |

(Continued)

FOREIGN PATENT DOCUMENTS

| | | | |
|---|---|---|---|
| JP | 2008092854 A | * | 4/2008 |
| WO | WO-9203456 A1 | | 3/1992 |

(Continued)

OTHER PUBLICATIONS

"International Application Serial No. PCT/US2019/036841, International Search Report mailed Oct. 1, 2019", 5 pgs.
(Continued)

*Primary Examiner* — Terra C Gibbs
(74) *Attorney, Agent, or Firm* — Schwegman Lundberg & Woessner, P.A.

(57) ABSTRACT

The present disclosure provides compositions and methods for inhibiting herpesvirus replication in a cell infected with herpesvirus. The composition includes a double stranded DNA molecule including a sequence of a cis regulatory sequence (crs) of a herpesvirus, wherein the crs is flanked on 5' end by a first sequence of at least 2 base pairs and on the 3' end by a second sequence of at least 2 base pairs.

10 Claims, 37 Drawing Sheets

Specification includes a Sequence Listing.

Cytomegalovirus is a double stranded DNA virus, belonging to b-Herpesviridae family Congenital infection CMV retinitis Infection in solid organ transplant Sequence of viral gene expression in CMV Immediate Early 2 (IE2) Protein

(51) Int. Cl.

| | |
|---|---|
| *A61K 31/662* | (2006.01) |
| *A61K 31/675* | (2006.01) |
| *A61K 31/7056* | (2006.01) |
| *A61K 31/713* | (2006.01) |

(52) U.S. Cl.
CPC ........ *A61K 31/675* (2013.01); *A61K 31/7056* (2013.01); *A61K 31/713* (2013.01); *C12N 2310/315* (2013.01); *C12N 2310/51* (2013.01)

(56) References Cited

U.S. PATENT DOCUMENTS

| | | |
|---|---|---|
| 7,683,185 B2 | 3/2010 | Joel et al. |
| 7,732,475 B2 | 6/2010 | Bressi et al. |
| 7,737,184 B2 | 6/2010 | Belvedere et al. |
| 7,741,494 B2 | 6/2010 | Bressi et al. |
| 7,772,245 B2 | 8/2010 | Anandan et al. |
| 7,795,304 B2 | 9/2010 | Belvedere et al. |
| 7,799,825 B2 | 9/2010 | Ferrigno et al. |
| 7,803,800 B2 | 9/2010 | Minucci et al. |
| 7,842,727 B2 | 11/2010 | Lan-hargest et al. |
| 7,842,835 B2 | 11/2010 | Kozikowski et al. |
| 2004/0023206 A1 | 2/2004 | Polansky |
| 2005/0234033 A1 | 10/2005 | Anandan et al. |
| 2010/0291003 A1 | 11/2010 | Rajagopal et al. |
| 2010/0292320 A1 | 11/2010 | Melvin, Jr. |
| 2010/0310500 A1 | 12/2010 | Graupe et al. |
| 2010/0311794 A1 | 12/2010 | Venkataramani |
| 2010/0317739 A1 | 12/2010 | Brown et al. |

FOREIGN PATENT DOCUMENTS

| | | |
|---|---|---|
| WO | WO-9819162 A1 | 5/1998 |
| WO | WO-0230879 A2 | 4/2002 |
| WO | WO-03082288 A1 | 10/2003 |
| WO | WO-2005108367 A1 | 11/2005 |
| WO | WO-2006017214 A2 | 2/2006 |
| WO | WO-2006017215 A2 | 2/2006 |
| WO | WO-2006123121 A1 | 11/2006 |
| WO | WO-2018075980 A1 | 4/2018 |
| WO | WO-2019241435 A1 | 12/2019 |

OTHER PUBLICATIONS

"International Application Serial No. PCT/US2019/036841, Written Opinion mailed Oct. 1, 2019", 12 pgs.

Chaturvedi, S, et al., "Disrupting Transcriptional Feedback Yields an Escape-Resistant Antiviral", BioRxiv, (Nov. 7, 2018).

"International Application Serial No. PCT/US2019/036841, International Preliminary Report on Patentability mailed Dec. 24, 2020", 14 pgs.

Adams, David, et al., "Patisiran, an RNAi Therapeutic, for Hereditary Transthyretin Amyloidosis", The New England Journal Of Medicine vol. 379 No. 1, (Jul. 2018), 11 pgs.

Asberg, A, et al., "Lessons Learned From a Randomized Study of Oral Valganciclovir Versus Parenteral Ganciclovir Treatment of Cytomegalovirus Disease in Solid Organ Transplant Recipients: The VICTOR Trial", Clinical Infectious Diseases, 62, pp. 1154-1160, (2016), 7 pgs.

Chan, Matilda, et al., "Animal Models of Corneal Injury", Bio Protoc., (Jul. 2015), 8 pgs.

Chang, W. L. William, et al., "Cloning of the Full-Length Rhesus Cytomegalovirus Genome as an Infectious and Self-Excisable Bacterial Artificial Chromosome for Analysis of Viral Pathogenesis", Journal Of Virology vol. 77 No. 9, (May 2003), 11 pgs.

Coen, Donald M, et al., "Two distinct loci confer resistance to acycloguanosine in herpes simplex virus type 1", Proc Natl A cad Sci US A 77, (1980), 2265-2269.

Coffin, J M, et al., "HIV Population Dynamics in Vivo: Implications for Genetic Variation, Pathogenesis, and Therapy", Science 267, pp. 483-489, (Jan. 27, 1995), 7 pgs.

Cunningham, Emmett T., "Cytomegalovirus: Ophthalmic Perspectives On A Pervasive Pathogen", Expert Review of Ophthalmology vol. 6 Issue 5, (Jan. 2014), 4 pgs.

Emery, V C, et al., "Prediction of cytomegalovirus load and resistance patterns after antiviral chemotherapy", Proc Natl Acad Sci US A 97, pp. 8039-8044, (Jul. 5, 2000), 6 pgs.

Enquist, Lynn W, et al., "Intrinsic and Innate Defenses of Neurons: Detente with the Herpesviruses", Journal of Virology 91, (Jan. 2017), 6 pgs.

Everett, R D, et al., "Herpes Simplex Virus Type 1 Genomes Are Associated with ND10 Nuclear Substructures in Quiescently Infected Human Fibroblasts", Journal of Virology 81, pp. 10991-11004, (Apr. 3, 2007), 14 pgs.

Everett, Roger D., et al., "Recruitment of Herpes Simplex Virus Type 1 Transcriptional Regulatory Protein ICP4 into Foci Juxtaposed to ND10 in Live, Infected Cells", Journal Of Virology vol. 77 No. 6, (Mar. 2003), 10 pgs.

Frobert, E, et al., "Resistance of herpes simplex viruses to acyclovir: An update from a ten-year survey in France", Antiviral Res 111, pp. 36-41, (2014), 3 pgs.

Goldberg, Daniel E, et al., "Outwitting Evolution: Fighting Drug-Resistant TB, Malaria, and HIV", Cell 148, (Mar. 16, 2012), 1271-1283.

Goldner, Thomas, et al., "The Novel Anticytomegalovirus Compound AIC246 (Letermovir) Inhibits Human Cytomegalovirus Replication through a Specific Antiviral Mechanism That Involves the Viral Terminase", Journal of Virology, vol. 85, (Oct. 2011), 10884-10893.

Isomura, H, et al., "A cis element between the TATA Box and the transcription start site of the major immediate-early promoter of human cytomegalovirus determines efficiency of viral replication", Journal of Virology, pp. 849-858, (Jan. 2008), 10 pgs.

Jaishankar, Dinesh, et al., "An off-target effect of BX795 blocks herpes simplex virus type 1 infection of the eye", Sci Transl Med.; 10(428), (Feb. 14, 2018), 24 pgs.

Kanasty, Rosemary, et al., "Delivery Materials For siRNA Therapeutics", Nature Materials vol. 12, (Nov. 2013), 11 pgs.

Khvorova, Anastasia, "The chemical evolution of oligonucleotide therapies of clinical utility", Nat Biotechnol., 35(3), (Mar. 2017), 24 pgs.

Lahmidi, Soumia, et al., "Dok-1 and Dok-2 Are Required To Maintain Herpes Simplex Virus 1-Specific CD8 T Cells in a Murine Model of Ocular Infection", Journal Of Virology vol. 91 Issue 15, (Aug. 2017), 15 pgs.

Lee, Henry H, et al., "Bacterial charity work leads to population-wide resistance", Nature 467, (Feb. 9, 2010), 82-85.

Liu, Bo, et al., "A cis-acting element in the major immediateearly (IE) promoter of human cytomegalovirus is required for negative regulation by IE2", Journal of Virology, vol. 65, No. 2, (Feb. 1991), p. 897-903.

Lu, Q, et al., "Mutation Spectra of Herpes Simplex Virus Type 1 Thymidine Kinase Mutants", J Virol 76, pp. 5822-5828, (Jun. 2002), 7 pgs.

Luecke, Stefanie, et al., "cGAS Is Activated By DNA In A Length-Dependent Manner", EMBO Reports vol. 18 No. 10, (Oct. 2017), 9 pgs.

Lurain, Nell S, et al., "Antiviral Drug Resistance of Human Cytomegalovirus", Microbiol Rev 23, (Oct. 2010), 689-712.

M, Elia, et al., "Cytomegalovirus Anterior Uveitis in Immunocompetent Patients", In EyeNet Magazine, pp. 37-38., (2016), 2 pgs.

Macias, Mimi P., et al., "An In Vitro System For Human Cytomegalovirus Immediate Early 2 Protein (IE2)-Mediated Site Dependent Repression Of Transciprtion And Direct Binding Of IE2 To The Major Immediate Early Promoter", Proceedings of the National Academy of Sciences vol. 90 No. 2, (Jan. 1993), 5 pgs.

Meylan, Sylvain, et al., "Targeting Antibiotic Tolerance, Pathogen by Pathogen", Cell172, (Mar. 8, 2018), 1228-1238.

Mulamba, Gilbert B., et al., "Human Cytomegalovirus Mutant with Sequence-Dependent Resistance to the Phosphorothioate Oligonucleotide Fomivirsen", Antimicrobial Agents And Chemotherapy vol. 42 No. 4, (Apr. 1998), 3 pgs.

(56)          References Cited

OTHER PUBLICATIONS

Pai, Anand, et al., "Fate-Regulating Circuits in Viruses: From Discovery to New Therapy Targets", Annu. Rev. Virol .. 4, (Aug. 11, 2017), 469-490.

Perelson, a S, et al., "Modelling Viral And Immune System Dynamics", Nat Rev Immnunol 2, pp. 28-36, (Jan. 2002), 9 pgs.

Reed, L. J., et al., "A Simple Method of Estimating Fifty Per Cent Endpoints", American Journal of Epidemiology, vol. 27, Issue 3, May 1938, pp. 493-497, https://doi.org/10.1093/oxfordjournals.aje.a118408, (5/1/38), 4 pgs.

Renzette, Nicholas, et al., "Extensive genome-wide variability of human cytomegalovirus in congenitally infected infants", PLoS Pathog 7, e1001344, (May 2011), 14 pgs.

Renzette, Nicholas, et al., "Limits and Patterns of Cytomegalovirus Genomic Diversity In Humans", Proceedings of the National Academy of Sciences vol. 112 No. 30, (Jul. 2015), 9 pgs.

Rosi, Nathaniel L., et al., "Oligonucleotide-Modified Gold Nanoparticles for Intracellular Gene Regulation", Science vol. 312 No. 5776, (May 2006).

Skouboe, M K, et al., "STING agonists enable antiviral cross-talk between human cells and confer protection against genital herpes in mice", PLoS Pathog 14, e1006976, (2018), 22 pgs.

Skouboe, Morten K., et al., "STONG Agonists Enable Antiviral Cross-Talk Between Human Cells And Confer Protection Against Genital Herpes In Mice", PLOS Pathogens Research Article, (Apr. 2018), 22 pgs.

Teng, M W, et al., "An endogenous accelerator for viral gene expression confers a fitness advantage", Cell 151, pp. 1569-1580., (Dec. 21, 2012), 27 pgs.

Vardi, N, et al., "Feedback-mediated signal conversion promotes viral fitness", Proc Natl Acad Sci U S A 115, pp. E8803-E8810, (2018), 8 pgs.

Weller, Sandra K, et al., "Herpes simplex viruses: mechanisms of DNA replication", Cold Spring Harb Perspect Biol 4, a013011, (2012), 15 pgs.

* cited by examiner

Cytomegalovirus is a double stranded DNA virus, belonging to b-Herpesviridae family Congenital infection CMV retinitis Infection in solid organ transplant Sequence of viral gene expression in CMV Immediate early (IE) genes → Early (E) genes → Late (L) genes Immediate Early 2 (IE2) Protein 1          579

N          C

Autoregulation
DNA binding
Dimerization
Transactivation

**Theoretical and biochemical assays to optimize
oligomerization of IE2 in the presence of ONT**

Optimizing IE2 oligomerization by ONT

Theoretical and biochemical assays to optimize
oligomerization of IE2 in the presence of ONT

IE2 oligomerize as a ring around ONT

In-vitro assays to optimize oligomerization of IE2 in the presence of ONT

Minimal circuit of IE2

ONT breaks negative feedback in IE2 minimal circuit

In-vitro assays to optimize oligomerization of IE2 in the presence of ONT

ONT breaks IE2 negative feedback leading to cytotoxicity in a dose dependent manner Transcription regulatory circuit disruptor interferes with
Herpesvirus productive infection in cell culture

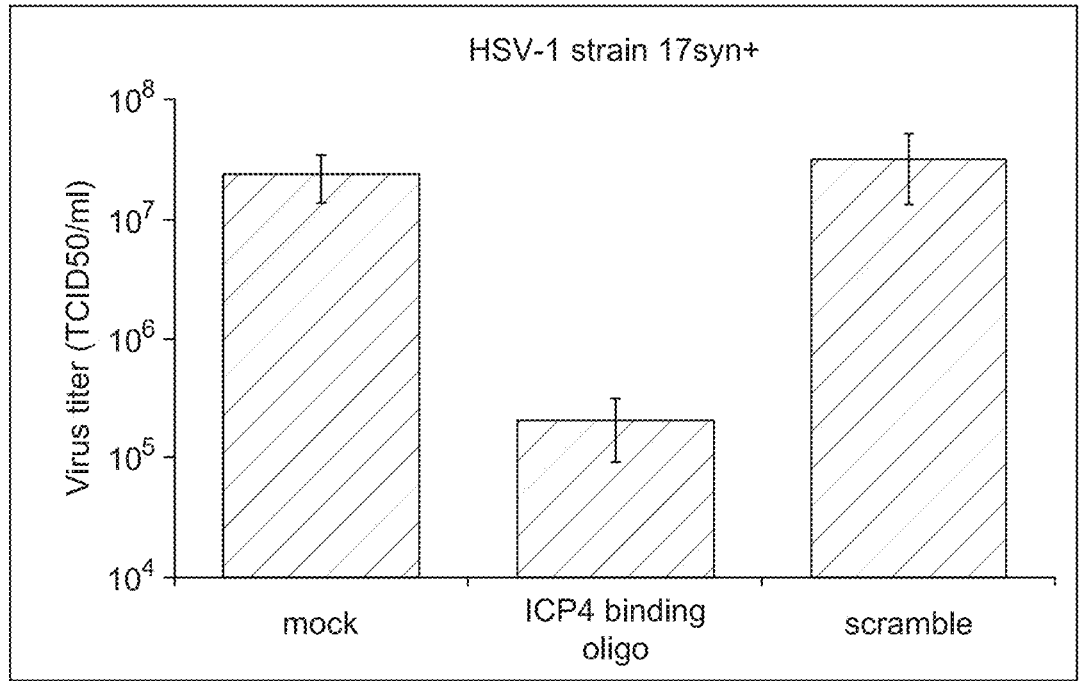
FIG. 5 (Cont`d)

Transcription regulatory circuit disruptor interferes with Herpesvirus productive infection in mice

Relative quantification of HSV1 in cornea cy3-C-DOT^C                          free cy3 dye C-DOT^C(N)      GACAGATCGTTTAGTGAACCGTACACGA
C-DOT^C        G*ACAGATCGTT*TAGTGAACC*GTACACG*A
C-DOT^Scram    A*TACCGCGTAA*CCAGAGGT*ATATAGGT*C C-DOT^C(N): Non phosphorothioated

| CMV  | T | C | G | T | T | T | A | G | T | G | A | A | C | C |
|------|---|---|---|---|---|---|---|---|---|---|---|---|---|---|
| RhCMV | T | C | G | T | T | T | A | G | G | G | A | A | C | C |
| MCMV | C | C | A | G | C | G | T | C | G | G | T | A | C | C |
FIG. 14A
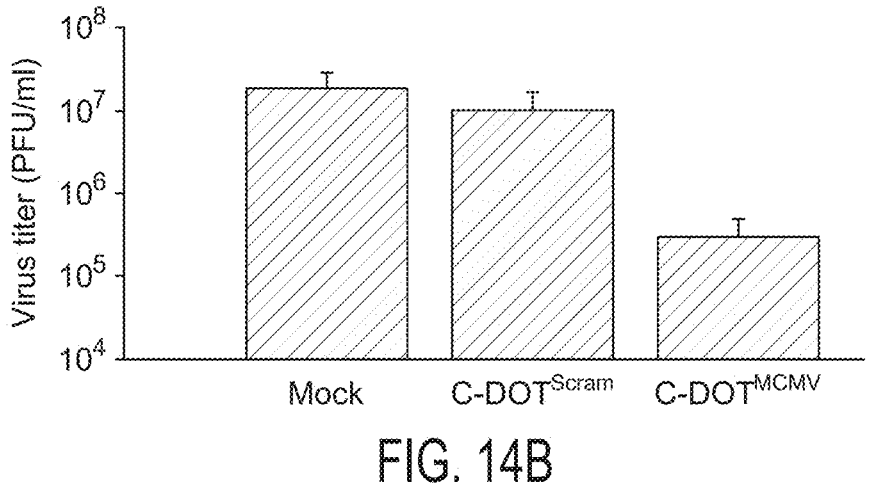
FIG. 14B
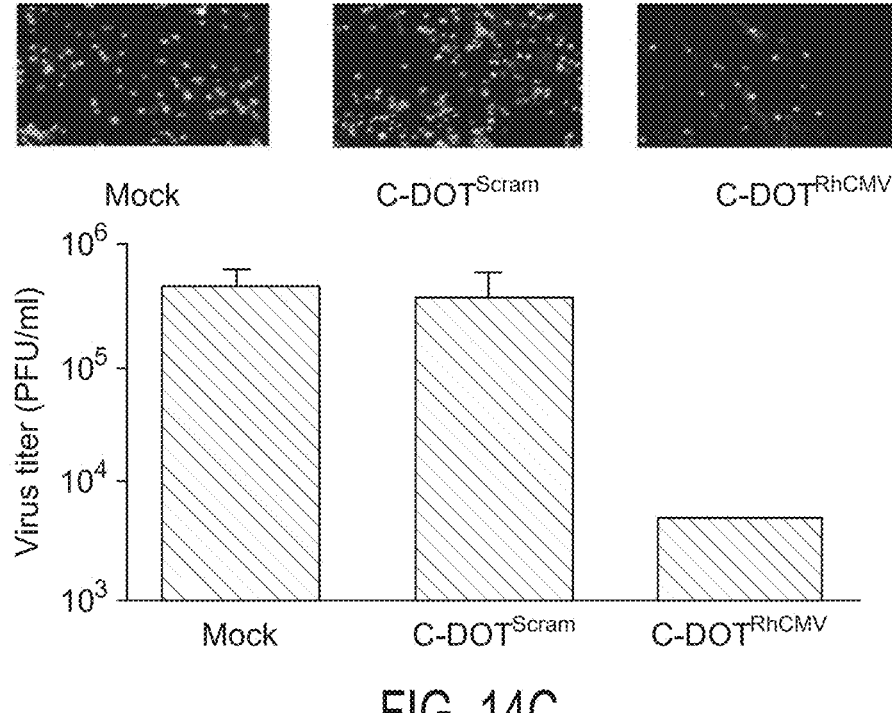
FIG. 14C GCV: Ganciclovir resistant
FOS: Foscarnet resistant Bright field                                      cy3-C-DOT

SEQUENCE LISTING

<160> NUMBER OF SEQ ID NOS: 47

<210> SEQ ID NO 1
<211> LENGTH: 28
<212> TYPE: DNA
<213> ORGANISM: Artificial sequence
<220> FEATURE:
<223> OTHER INFORMATION: synthetic sequence

<400> SEQUENCE: 1
gacagatcgt ttagtgaacc gtacacga                                              28

<210> SEQ ID NO 2
<211> LENGTH: 28
<212> TYPE: DNA
<213> ORGANISM: Artificial sequence
<220> FEATURE:
<223> OTHER INFORMATION: synthetic sequence

<400> SEQUENCE: 2
gacagaccag cgtcggtacc gtacacga                                              28

<210> SEQ ID NO 3
<211> LENGTH: 29
<212> TYPE: DNA
<213> ORGANISM: Artificial sequence
<220> FEATURE:
<223> OTHER INFORMATION: synthetic sequence

<400> SEQUENCE: 3
ccgaggacgc cccgatcgtc cacacggag                                             29

<210> SEQ ID NO 4
<211> LENGTH: 14
<212> TYPE: DNA
<213> ORGANISM: Artificial sequence
<220> FEATURE:
<223> OTHER INFORMATION: synthetic sequence

<400> SEQUENCE: 4
cgtttagtga accg                                                            14

<210> SEQ ID NO 5
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond  is present between the
      nucleotides at positions 1 and 2
<220> FEATURE:
<221> NAME/KEY: misc_feature
<222> LOCATION: (11)..(12)
<223> OTHER INFORMATION: A Phosphorothioate bond  is present between the
      nucleotides at positions 11 and 12
<220> FEATURE:
<221> NAME/KEY: misc_feature
<222> LOCATION: (20)..(21)
<223> OTHER INFORMATION: A Phosphorothioate bond  is present between the
      nucleotides at positions 20 and 21
<220> FEATURE:
<221> NAME/KEY: misc_feature
<222> LOCATION: (28)..(29)
<223> OTHER INFORMATION: A Phosphorothioate bond  is present between the
      nucleotides at positions 28 and 29

<400> SEQUENCE: 5

-continued

```
gacagatcgt ttagtgaacc gtacacga                                    28

<210> SEQ ID NO 6
<211> LENGTH: 14
<212> TYPE: DNA
<213> ORGANISM: Artificial sequence
<220> FEATURE:
<223> OTHER INFORMATION: synthetic sequence

<400> SEQUENCE: 6
cgtttaggga accg                                                   14

<210> SEQ ID NO 7
<211> LENGTH: 28
<212> TYPE: DNA
<213> ORGANISM: Artificial sequence
<220> FEATURE:
<223> OTHER INFORMATION: synthetic sequence

<400> SEQUENCE: 7
gacagatcgt ttagggaacc gtacacga                                    28

<210> SEQ ID NO 8
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond is present between the
      nucleotides at positions 1 and 2.
<220> FEATURE:
<221> NAME/KEY: misc_feature
<222> LOCATION: (10)..(11)
<223> OTHER INFORMATION: A Phosphorothioate bond is present between the
      nucleotides at positions 10 and 11.
<220> FEATURE:
<221> NAME/KEY: misc_feature
<222> LOCATION: (19)..(20)
<223> OTHER INFORMATION: A Phosphorothioate bond is present between the
      nucleotides at positions 19 and 20.
<220> FEATURE:
<221> NAME/KEY: misc_feature
<222> LOCATION: (27)..(28)
<223> OTHER INFORMATION: A Phosphorothioate bond is present between the
      nucleotides at positions 27 and 28.

<400> SEQUENCE: 8
gacagatcgt ttagggaacc gtacacga                                    28

<210> SEQ ID NO 9
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond is present between the
      nucleotides at positions 1 and 2
<220> FEATURE:
<221> NAME/KEY: misc_feature
<222> LOCATION: (9)..(10)
<223> OTHER INFORMATION: A Phosphorothioate bond is present between the
      nucleotides at positions 9 and 10
<220> FEATURE:
<221> NAME/KEY: misc_feature
<222> LOCATION: (16)..(17)
```

<223> OTHER INFORMATION: A Phosphorothioate bond is present between the
      nucleotides at positions 16 and 17
<220> FEATURE:
<221> NAME/KEY: misc_feature
<222> LOCATION: (27)..(28)
<223> OTHER INFORMATION: A Phosphorothioate bond is present between the
      nucleotides at positions 27 and 28

<400> SEQUENCE: 9
gacagaccag cgtcggtacc gtacacga                                          28

<210> SEQ ID NO 10
<211> LENGTH: 15
<212> TYPE: DNA
<213> ORGANISM: Artificial sequence
<220> FEATURE:
<223> OTHER INFORMATION: synthetic sequence

<400> SEQUENCE: 10
cgccccgatc gtcca                                                        15

<210> SEQ ID NO 11
<211> LENGTH: 29
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (3)..(4)
<223> OTHER INFORMATION: A Phosphorothioate bond is present between the
      nucleotides at positions 3 and 4.
<220> FEATURE:
<221> NAME/KEY: misc_feature
<222> LOCATION: (8)..(9)
<223> OTHER INFORMATION: A Phosphorothioate bond is present between the
      nucleotides at positions 8 and 9.
<220> FEATURE:
<221> NAME/KEY: misc_feature
<222> LOCATION: (17)..(18)
<223> OTHER INFORMATION: A Phosphorothioate bond is present between the
      nucleotides at positions 17 and 18.
<220> FEATURE:
<221> NAME/KEY: misc_feature
<222> LOCATION: (26)..(27)
<223> OTHER INFORMATION: A Phosphorothioate bond is present between the
      nucleotides at positions 26 and 27.

<400> SEQUENCE: 11
ccgaggacgc cccgatcgtc cacacggag                                         29

<210> SEQ ID NO 12
<211> LENGTH: 64
<212> TYPE: DNA
<213> ORGANISM: Artificial sequence
<220> FEATURE:
<223> OTHER INFORMATION: synthetic sequence

<400> SEQUENCE: 12
taatacgact cactataggg cgaattggag ctcgtttagt gaaccgtcag atctctagaa       60
gctt                                                                    64

<210> SEQ ID NO 13
<211> LENGTH: 64
<212> TYPE: DNA
<213> ORGANISM: Artificial sequence
<220> FEATURE:
<223> OTHER INFORMATION: synthetic sequence

<400> SEQUENCE: 13

-continued

```
aagcttctag agatctgacg gttcactaaa cgagctccaa ttcgccctat agtgagtcgt      60
atta                                                                  64

<210> SEQ ID NO 14
<211> LENGTH: 50
<212> TYPE: DNA
<213> ORGANISM: Artificial sequence
<220> FEATURE:
<223> OTHER INFORMATION: synthetic sequence

<400> SEQUENCE: 14
taatacgact cactataggg cgaattggag ctcggcaggc atgcaagctt                 50

<210> SEQ ID NO 15
<211> LENGTH: 50
<212> TYPE: DNA
<213> ORGANISM: Artificial sequence
<220> FEATURE:
<223> OTHER INFORMATION: synthetic sequence

<400> SEQUENCE: 15
aagcttgcat gcctgccgag ctccaattcg ccctatagtg agtcgtatta                 50

<210> SEQ ID NO 16
<211> LENGTH: 21
<212> TYPE: DNA
<213> ORGANISM: Artificial sequence
<220> FEATURE:
<223> OTHER INFORMATION: synthetic sequence

<400> SEQUENCE: 16
agatcgttta gtgaaccgta c                                                21

<210> SEQ ID NO 17
<211> LENGTH: 21
<212> TYPE: DNA
<213> ORGANISM: Artificial sequence
<220> FEATURE:
<223> OTHER INFORMATION: synthetic sequence

<400> SEQUENCE: 17
gtacggttca ctaaacgatc t                                                21

<210> SEQ ID NO 18
<211> LENGTH: 28
<212> TYPE: DNA
<213> ORGANISM: Artificial sequence
<220> FEATURE:
<223> OTHER INFORMATION: synthetic sequence

<400> SEQUENCE: 18
tcgtgtacgg ttcactaaac gatctgtc                                         28

<210> SEQ ID NO 19
<211> LENGTH: 28
<212> TYPE: DNA
<213> ORGANISM: Artificial sequence
<220> FEATURE:
<223> OTHER INFORMATION: synthetic sequence

<400> SEQUENCE: 19
ataccgcgta accagaggta tataggtc                                         28

<210> SEQ ID NO 20
```

```
<211> LENGTH: 28
<212> TYPE: DNA
<213> ORGANISM: Artificial sequence
<220> FEATURE:
<223> OTHER INFORMATION: synthetic sequence

<400> SEQUENCE: 20
gacctatata cctctggtta cgcggtat                                    28

<210> SEQ ID NO 21
<211> LENGTH: 28
<212> TYPE: DNA
<213> ORGANISM: Artificial sequence
<220> FEATURE:
<223> OTHER INFORMATION: synthetic sequence

<400> SEQUENCE: 21
tcgtgtacgg ttccctaaac gatctgtc                                   28

<210> SEQ ID NO 22
<211> LENGTH: 28
<212> TYPE: DNA
<213> ORGANISM: Artificial sequence
<220> FEATURE:
<223> OTHER INFORMATION: synthetic sequence

<400> SEQUENCE: 22
tcgtgtacgg taccgacgct ggtctgtc                                   28

<210> SEQ ID NO 23
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to
      5Cy3.

<400> SEQUENCE: 23
gacagatcgt ttagtgaacc gtacacga                                   28

<210> SEQ ID NO 24
<211> LENGTH: 34
<212> TYPE: DNA
<213> ORGANISM: Artificial sequence
<220> FEATURE:
<223> OTHER INFORMATION: synthetic sequence

<400> SEQUENCE: 24
cgtttagtga accgcgcgcg cgtttagtga accg                            34

<210> SEQ ID NO 25
<211> LENGTH: 34
<212> TYPE: DNA
<213> ORGANISM: Artificial sequence
<220> FEATURE:
<223> OTHER INFORMATION: synthetic sequence

<400> SEQUENCE: 25
cggttcacta aacgcgcgcg cggttcacta aacg                            34

<210> SEQ ID NO 26
<211> LENGTH: 29
<212> TYPE: DNA
```

-continued

```
<213> ORGANISM: Artificial sequence
<220> FEATURE:
<223> OTHER INFORMATION: synthetic sequence
<220> FEATURE:
<221> NAME/KEY: misc_feature
<222> LOCATION: (3)..(4)
<223> OTHER INFORMATION: A Phosphorothioate bond is positioned between
      the nucleotides at positions 3 and 4.
<220> FEATURE:
<221> NAME/KEY: misc_feature
<222> LOCATION: (12)..(13)
<223> OTHER INFORMATION: A Phosphorothioate bond is positioned between
      the nucleotides at positions 12 and 13.
<220> FEATURE:
<221> NAME/KEY: misc_feature
<222> LOCATION: (21)..(22)
<223> OTHER INFORMATION: A Phosphorothioate bond is positioned between
      the nucleotides at positions 21 and 22.
<220> FEATURE:
<221> NAME/KEY: misc_feature
<222> LOCATION: (26)..(27)
<223> OTHER INFORMATION: A Phosphorothioate bond is positioned between
      the nucleotides at positions 26 and 27.

<400> SEQUENCE: 26
ccgaggacgc cccgatcgtc cacacggag                                         29

<210> SEQ ID NO 27
<211> LENGTH: 20
<212> TYPE: DNA
<213> ORGANISM: Artificial sequence
<220> FEATURE:
<223> OTHER INFORMATION: synthetic sequence

<400> SEQUENCE: 27
gggggacgat cgtcgggggg                                                   20

<210> SEQ ID NO 28
<211> LENGTH: 20
<212> TYPE: DNA
<213> ORGANISM: Artificial sequence
<220> FEATURE:
<223> OTHER INFORMATION: synthetic sequence

<400> SEQUENCE: 28 cccccegacg atcgtccccc                                                   20

<210> SEQ ID NO 29
<211> LENGTH: 22
<212> TYPE: DNA
<213> ORGANISM: Artificial sequence
<220> FEATURE:
<223> OTHER INFORMATION: synthetic sequence

<400> SEQUENCE: 29
ccgtgacaat tacctggcct tc                                                22

<210> SEQ ID NO 30
<211> LENGTH: 20
<212> TYPE: DNA
<213> ORGANISM: Artificial sequence
<220> FEATURE:
<223> OTHER INFORMATION: synthetic sequence

<400> SEQUENCE: 30
cagggccttc agctggtttc                                                   20

<210> SEQ ID NO 31
<211> LENGTH: 23
```

-continued

```
<212> TYPE: DNA
<213> ORGANISM: Artificial sequence
<220> FEATURE:
<223> OTHER INFORMATION: synthetic sequence

<400> SEQUENCE: 31
ttcctacttg gcagtacatc tac                                           23

<210> SEQ ID NO 32
<211> LENGTH: 23
<212> TYPE: DNA
<213> ORGANISM: Artificial sequence
<220> FEATURE:
<223> OTHER INFORMATION: synthetic sequence

<400> SEQUENCE: 32
cctataggct aagctatacc atc                                           23

<210> SEQ ID NO 33
<211> LENGTH: 17
<212> TYPE: DNA
<213> ORGANISM: Artificial sequence
<220> FEATURE:
<223> OTHER INFORMATION: synthetic sequence

<400> SEQUENCE: 33
tgacatcctc gcccagg                                                  17

<210> SEQ ID NO 34
<211> LENGTH: 23
<212> TYPE: DNA
<213> ORGANISM: Artificial sequence
<220> FEATURE:
<223> OTHER INFORMATION: synthetic sequence

<400> SEQUENCE: 34
ttactgagac ttgttcctca ggt                                           23

<210> SEQ ID NO 35
<211> LENGTH: 19
<212> TYPE: DNA
<213> ORGANISM: Artificial sequence
<220> FEATURE:
<223> OTHER INFORMATION: synthetic sequence

<400> SEQUENCE: 35
tgaccgagga ttgcaacga                                                19

<210> SEQ ID NO 36
<211> LENGTH: 19
<212> TYPE: DNA
<213> ORGANISM: Artificial sequence
<220> FEATURE:
<223> OTHER INFORMATION: synthetic sequence

<400> SEQUENCE: 36
cggcatgatt gacagcctg                                                19

<210> SEQ ID NO 37
<211> LENGTH: 20
<212> TYPE: DNA
<213> ORGANISM: Artificial sequence
<220> FEATURE:
<223> OTHER INFORMATION: synthetic sequence

<400> SEQUENCE: 37
```

-continued gtctgacggt ctgtctctgg                                                    20

<210> SEQ ID NO 38
<211> LENGTH: 20
<212> TYPE: DNA
<213> ORGANISM: Artificial sequence
<220> FEATURE:
<223> OTHER INFORMATION: synthetic sequence

<400> SEQUENCE: 38
caagaagatg cggctgtctc                                                    20

<210> SEQ ID NO 39
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond is present between the
      nucleotides at positions 1 and 2.
<220> FEATURE:
<221> NAME/KEY: misc_feature
<222> LOCATION: (8)..(9)
<223> OTHER INFORMATION: A Phosphorothioate bond is present between the
      nucleotides at positions 8 and 9.
<220> FEATURE:
<221> NAME/KEY: misc_feature
<222> LOCATION: (17)..(18)
<223> OTHER INFORMATION: A Phosphorothioate bond is present between the
      nucleotides at positions 17 and 18.
<220> FEATURE:
<221> NAME/KEY: misc_feature
<222> LOCATION: (27)..(28)
<223> OTHER INFORMATION: A Phosphorothioate bond is present between the
      nucleotides at positions 27 and 28.

<400> SEQUENCE: 39
tcgtgtacgg ttcactaaac gatctgtc                                           28

<210> SEQ ID NO 40
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond is present between the
      nucleotides at positions 1 and 2
<220> FEATURE:
<221> NAME/KEY: misc_feature
<222> LOCATION: (11)..(12)
<223> OTHER INFORMATION: A Phosphorothioate bond is present between the
      nucleotides at positions 11 and 12
<220> FEATURE:
<221> NAME/KEY: misc_feature
<222> LOCATION: (19)..(20)
<223> OTHER INFORMATION: A Phosphorothioate bond is present between the
      nucleotides at positions 19 and 20
<220> FEATURE:
<221> NAME/KEY: misc_feature
<222> LOCATION: (27)..(28)
<223> OTHER INFORMATION: A Phosphorothioate bond is present between the
      nucleotides at positions 27 and 28

<400> SEQUENCE: 40
ataccgcgta accagaggta tataggtc                                           28

```
<210> SEQ ID NO 41
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond is present between the
      nucleotides at positions 1 and 2.
<220> FEATURE:
<221> NAME/KEY: misc_feature
<222> LOCATION: (9)..(10)
<223> OTHER INFORMATION: A Phosphorothioate bond is present between the
      nucleotides at positions 9 and 10.
<220> FEATURE:
<221> NAME/KEY: misc_feature
<222> LOCATION: (17)..(18)
<223> OTHER INFORMATION: A Phosphorothioate bond is present between the
      nucleotides at positions 17 and 18.
<220> FEATURE:
<221> NAME/KEY: misc_feature
<222> LOCATION: (27)..(28)
<223> OTHER INFORMATION: A Phosphorothioate bond is present between the
      nucleotides at positions 27 and 28.

<400> SEQUENCE: 41
gacctatata cctctggtta cgcggtat                                        28

<210> SEQ ID NO 42
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond is present between the
      nucleotides at positions 1 and 2.
<220> FEATURE:
<221> NAME/KEY: misc_feature
<222> LOCATION: (11)..(12)
<223> OTHER INFORMATION: A Phosphorothioate bond is present between the
      nucleotides at positions 11 and 12.
<220> FEATURE:
<221> NAME/KEY: misc_feature
<222> LOCATION: (19)..(20)
<223> OTHER INFORMATION: A Phosphorothioate bond is present between the
      nucleotides at positions 19 and 20.
<220> FEATURE:
<221> NAME/KEY: misc_feature
<222> LOCATION: (27)..(28)
<223> OTHER INFORMATION: A Phosphorothioate bond is present between the
      nucleotides at positions 27 and 28.

<400> SEQUENCE: 42
tcgtgtacgg taccgacgct ggtctgtc                                        28

<210> SEQ ID NO 43
<211> LENGTH: 28
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(2)
<223> OTHER INFORMATION: A Phosphorothioate bond is present between the
      nucleotides at positions 1 and 2.
<220> FEATURE:
<221> NAME/KEY: misc_feature
<222> LOCATION: (9)..(10)
<223> OTHER INFORMATION: A Phosphorothioate bond is present between the
```

-continued

```
       nucleotides at positions 9 and 10.
<220> FEATURE:
<221> NAME/KEY: misc_feature
<222> LOCATION: (18)..(19)
<223> OTHER INFORMATION: A Phosphorothioate bond is present between the
       nucleotides at positions 18 and 19.
<220> FEATURE:
<221> NAME/KEY: misc_feature
<222> LOCATION: (27)..(28)
<223> OTHER INFORMATION: A Phosphorothioate bond is present between the
       nucleotides at positions 27 and 28.

<400> SEQUENCE: 43
tcgtgtacgg ttccctaaac gatctgtc                                          28

<210> SEQ ID NO 44
<211> LENGTH: 29
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to
       5Cy3
<220> FEATURE:
<221> NAME/KEY: misc_feature
<222> LOCATION: (3)..(4)
<223> OTHER INFORMATION: A Phosphorothioate bond is present between the
       nucleotides at positions 3 and 4.
<220> FEATURE:
<221> NAME/KEY: misc_feature
<222> LOCATION: (8)..(9)
<223> OTHER INFORMATION: A Phosphorothioate bond is present between the
       nucleotides at positions 8 and 9.
<220> FEATURE:
<221> NAME/KEY: misc_feature
<222> LOCATION: (17)..(18)
<223> OTHER INFORMATION: A Phosphorothioate bond is present between the
       nucleotides at positions 17 and 18.
<220> FEATURE:
<221> NAME/KEY: misc_feature
<222> LOCATION: (26)..(27)
<223> OTHER INFORMATION: A Phosphorothioate bond is present between the
       nucleotides at positions 26 and 27.

<400> SEQUENCE: 44
ccgaggacgc cccgatcgtc cacacggag                                         29

<210> SEQ ID NO 45
<211> LENGTH: 14
<212> TYPE: DNA
<213> ORGANISM: Artificial sequence
<220> FEATURE:
<223> OTHER INFORMATION: synthetic sequence

<400> SEQUENCE: 45
tcgtttagtg aacc                                                         14

<210> SEQ ID NO 46
<211> LENGTH: 14
<212> TYPE: DNA
<213> ORGANISM: Artificial sequence
<220> FEATURE:
<223> OTHER INFORMATION: synthetic sequence

<400> SEQUENCE: 46
tcgtttaggg aacc                                                         14

<210> SEQ ID NO 47
```

-continued

```
<211> LENGTH: 14
<212> TYPE: DNA
<213> ORGANISM: Artificial sequence
<220> FEATURE:
<223> OTHER INFORMATION: synthetic sequence

<400> SEQUENCE: 47
ccagcgtcgg tacc                                                              14
```

COMPOSITIONS FOR HERPESVIRUS TRANSCRIPTIONAL FEEDBACK CIRCUIT DISRUPTION AND USES THEREOF

CROSS-REFERENCE TO RELATED APPLICATIONS

This application is a U.S. National Stage Filing under 35 U.S.C. 371 from International Patent Application Serial No. PCT/US2019/036841, filed Jun. 12, 2019, Published as WO 2019/241435 on Dec. 19, 2019, which application claims the benefit of U.S. provisional application Ser. No. 62/684,099, filed on Jun. 12, 2018, the contents of both of which are incorporated herein by reference in their entireties.

SUPPORT OF GOVERNMENT CLAUSE

This invention was made with government support under GM083395 awarded by the National Institutes of Health. The government has certain rights in the invention.

INCORPORATION BY REFERENCE OF SEQUENCE LISTING

A Sequence Listing is provided herewith as a text file, "2398379.txt" created on Jan. 4, 2024 and having a size of 16,390 bytes. The contents of the text file are incorporated by reference herein in their entirety.

INTRODUCTION

Eight herpesviruses routinely infect humans: herpes simplex virus types 1 and 2, varicella-zoster virus, cytomegalovirus, Epstein-Barr virus, human herpesvirus 6 (variants A and B), human herpesvirus 7, and Kaposi's sarcoma virus or human herpesvirus 8. A simian virus, B virus, occasionally infects humans. All herpesviruses can establish latent infection within specific tissues.

Herpesviruses are divided into three groups: The α herpesviruses, herpes simplex virus types 1 and 2, and varicella-zoster virus; β herpesviruses, cytomegalovirus, and human herpesviruses 6 and 7; and γ herpesviruses, Epstein-Barr virus and human herpesvirus 8.

Cytomegalovirus (CMV) is associated with widespread morbidity and mortality. Infection with CMV is common, and it has been estimated that between 50% and 85% of people in the United States have had a CMV infection by the time they are 40 years old. Although CMV infection generally does not produce symptoms in healthy adults, high-risk groups, including immunocompromised organ transplant recipients and HIV-infected individuals, are at risk of developing CMV-associated disease. CMV is a leading cause of birth defects.

SUMMARY

The present disclosure provides a method for inhibiting herpesvirus replication in a cell infected with herpesvirus, the method including contacting the cell with a double stranded DNA molecule including a sequence of a cis regulatory sequence (crs) of a herpesvirus, wherein the crs is flanked on the 5' end by a first sequence of at least 2 base pairs and on the 3' end by a second sequence of at least 2 base pairs. Compositions including a double stranded DNA molecule including a sequence of a cis regulatory sequence (crs) of a herpesvirus, wherein the ers is flanked on the S' end by a first sequence of at least 2 base pairs and on the 3' end by a second sequence of at least 2 base pairs are also provided herein. The present disclosure further provides a method of treating a herpesvirus infection in an individual, the method comprising administering to the individual an effective amount of a double stranded DNA molecule including a sequence of a cis regulatory sequence (crs) of a herpesvirus, wherein the ers is flanked on the S' end by a first sequence of at least 2 base pairs and on the 3' end by a second sequence of at least 2 base pairs. In some cases, the crs is flanked on the 5' end by a first sequence of at least 3, 4, 5, 6, or 7 base pairs and on the 3' end by a second sequence of at least 3, 4, 5, 6, or 7 base pairs. In certain aspects, the first sequence and the second sequence have the same nucleotide sequence. In certain aspects, the first sequence and the second sequence have different nucleotide sequences. In certain aspects, the first sequence and the second sequence have the length. In certain aspects, the first sequence and the second sequence have different lengths. In certain aspects, the nucleotide sequences of the first sequence and/or the second sequence are heterologous to the crs.

The present disclosure also provides a method for inhibiting replication of a herpesvirus in a cell infected with a herpesvirus, the method including contacting the cell with a double stranded DNA molecule including a sequence of a cis regulatory sequence (crs) of the herpesvirus, wherein the crs is flanked on the S' end by a first sequence of at least 2 base pairs and on the 3' end by a second sequence of at least 2 base pairs. In some cases, the crs is flanked on the 5' end by a first sequence of at least 7 base pairs and on the 3' end by a second sequence of at least 7 base pairs. In some cases, one or both of the first sequence of at least 2 base pairs and the second sequence of at least 2 base pairs does not have a DNA sequence of a naturally occurring herpesvirus. In some cases, the herpesvirus is selected from cytomegalovirus (CMV), herpes simplex virus-1 (HSV-1), herpes simplex virus-2 (HSV-2), varicella zoster virus, Epstein-Barr virus (EBV), and Kaposi's sarcoma-associated herpesvirus (KSHV).

The present disclosure provides a method of treating a herpesvirus infection in an individual, the method comprising administering to the individual an effective amount of a double stranded DNA molecule comprising a sequence comprising a sequence of a cis regulatory sequence (crs) of the herpesvirus, wherein the crs is flanked on the 5' end by a first sequence of at least 2 base pairs and on the 3' end by a second sequence of at least 2 base pairs. In some cases, the herpesvirus is CMV. In some cases, the herpesvirus is HSV-1. In some cases, the individual is a human. In some cases, the method includes administering an effective amount of at least two double stranded DNA molecules, each comprising a sequence of a cis regulatory sequence (crs) of a different herpesvirus, wherein the crs is flanked on the 5' end by a first sequence of at least 2 base pairs and on the 3' end by a second sequence of at least 2 base pairs. In certain aspects, the first sequence flanking the first DNA molecule and the first sequence flanking the second DNA molecule have the same sequence. In certain aspects, the first sequence flanking the first DNA molecule and the first sequence flanking the second DNA molecule have different sequences. In certain aspects, the second sequence flanking the first DNA molecule and the second sequence flanking the second DNA molecule have the same sequence. In certain aspects, the second sequence flanking the first DNA molecule and the second sequence flanking the second DNA molecule have different sequences.

In some cases, the method of treating a herpesvirus infection includes administering at least a second therapeutic agent to the individual. In some cases, the second therapeutic agent is ganciclovir, foscarnet, cidofovir, maribavir, or valganciclovir. In some cases, the second therapeutic agent is an HDAC inhibitor.

In some cases, the individual receiving a treatment for herpesvirus infection is an organ transplant recipient. In some cases, the individual is a bone marrow transplant recipient. In some cases, the individual does not have a herpesvirus infection, and is a prospective organ transplant recipient. In some cases, the individual does not have a herpesvirus infection, and is a prospective bone marrow transplant recipient. In some cases, the individual is a pregnant female. In some cases, the individual is a neonate.

The present disclosure provides a method of inhibiting herpesvirus replication in an organ or tissue, the method comprising contacting the organ or tissue in vitro or ex vivo with a double stranded DNA molecule including a sequence including a sequence of a cis regulatory sequence (crs) of the herpesvirus, wherein the crs is flanked on the 5' end by a first sequence of at least 2 base pairs and on the 3' end by a second sequence of at least 2 base pairs, as provided herein. In some cases, the herpesvirus is CMV. In some cases, the herpesvirus is HSV-1. In some cases, the organ or tissue is contacted in vitro or ex vivo with the double stranded DNA molecule including a sequence including a sequence of a cis regulatory sequence (crs) of the herpesvirus for a period of time of from about 15 minutes to about 48 hours, or more than 48 hours, wherein the crs is flanked on the 5' end by a first sequence of at least 2 base pairs and on the 3' end by a second sequence of at least 2 base pairs. In some cases, the organ or tissue is contacted in vitro or ex vivo with the double stranded DNA molecule in a liquid medium.

The present disclosure provides a method of reducing the likelihood that a transplant recipient will become infected with herpesvirus from a donor organ or tissue, the method comprising: a) contacting the organ or tissue in vitro or ex vivo with a double stranded DNA molecule including a sequence including a sequence of a cis regulatory sequence (crs) of the herpesvirus, wherein the crs is flanked on the 5' end by a first sequence of at least 2 base pairs and on the 3' end by a second sequence of at least 2 base pairs, thereby producing a double stranded DNA molecule-treated organ or tissue; and b) transplanting the double stranded DNA molecule-treated organ or tissue into the transplant recipient. In some cases, the herpesvirus is CMV. In some cases, the herpesvirus is HSV-1.

The present disclosure provides a composition, the composition including a double stranded DNA molecule comprising a sequence of a cis regulatory sequence (crs) of the herpesvirus, wherein the crs is flanked on the 5' end by a first sequence of at least 2 base pairs and on the 3' end by a second sequence of at least 2 base pairs, as provided herein. In some cases, the crs is flanked on the 5' end by a first sequence of at least 7 base pairs and on the 3' end by a second sequence of at least 7 base pairs. In some cases, one or both of the first sequence of at least 2 base pairs and the second sequence of at least 2 base pairs does not have a DNA sequence of a naturally occurring herpesvirus. In some cases, the herpesvirus is selected from cytomegalovirus (CMV), herpes simplex virus-1 (HSV-1), herpes simplex virus-2 (HSV-2), varicella zoster virus, Epstein-Barr virus (EBV), and Kaposi's sarcoma-associated herpesvirus (KSHV).

In certain aspects, the DNA molecule may include a modification(s) that increases the half-life, e.g., in vivo half-life of the molecule. In certain aspects, the DNA molecule may include a modified backbone. In certain aspects, the DNA molecule may include a modified backbone comprising internal phosphorothioate bonds. In certain aspects, the DNA molecule may include a backbone comprising a plurality phosphorothioate bonds, such as, at least 2, 3, 4, 5, 6, 7, and up to 14 phosphorothioate bonds. In certain aspects, the phosphorothioate bonds may be distributed evenly across the DNA molecule.

BRIEF DESCRIPTION OF THE DRAWINGS

FIG. 1 also provides a schematic depicting the sequence of viral gene expression in CMV and a schematic depicting functional regions of the CMV Immediate Early (IE2) protein.

FIGS. 6A-6E. Feedback disruption inhibits viral replication in an in vivo model. Schematic of the HSV-1 corneal infection model in mice (a). I mages showing that an ICP-4 disruptor, a double stranded oligonucleotide (ONT) having the sequence CCGAGGACGCCCCGATCGTCCACACG-GAG (SEQ ID NO: 3), interferes with HSV1 replication in cornea. Bottom rows show magnified versions of the identified areas of the images in the row above (b). Quantification of HSV-1 YFP expressing cells in corneas, as determined from the YFP: DAPI ratio (c). HSV-1 viral titers from HSV-1 infected corneas 2 days after treatment with either 25 μM PBS, scrambled dsDNA sequence (C-DOT$^{Seram}$) or C-DOT for HSV-1 (C-DOT$^H$) (d). HSV-1 viral genomic DNA quantification by qPCR 2 days after treatment (e).

Figure 6A:
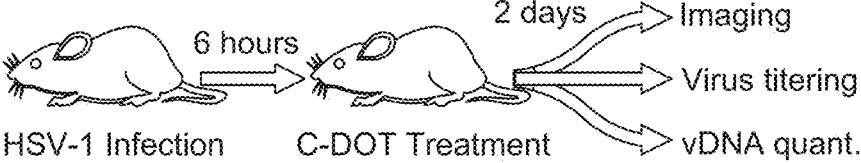
Figure 6B:
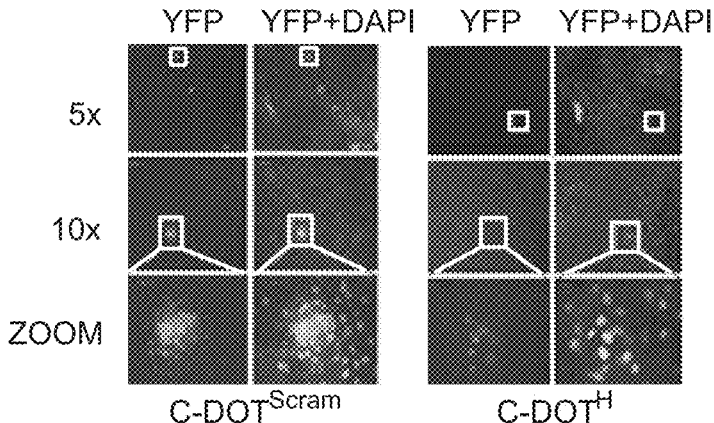
Figure 6C:
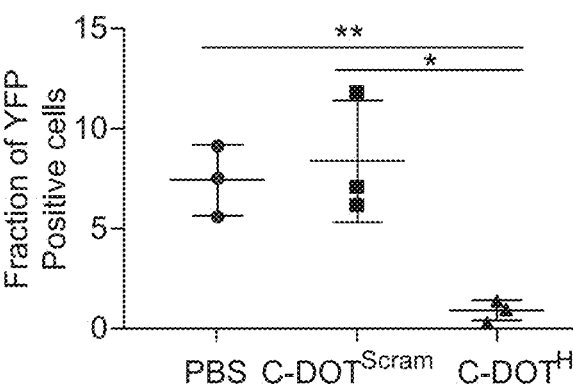
Figure 6D:
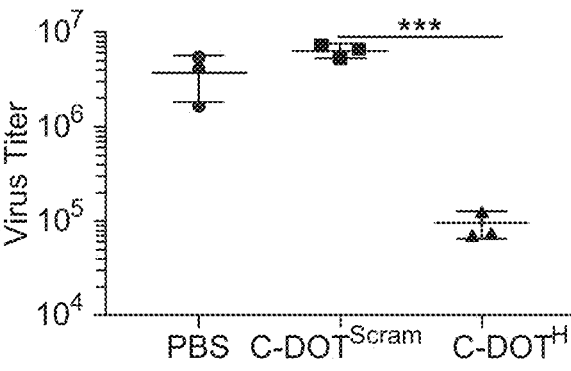
Figure 6E:
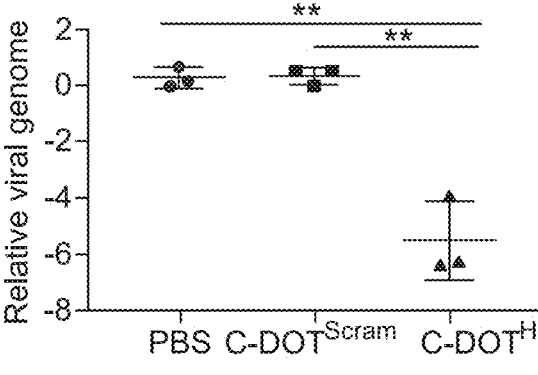
Figure 6F:
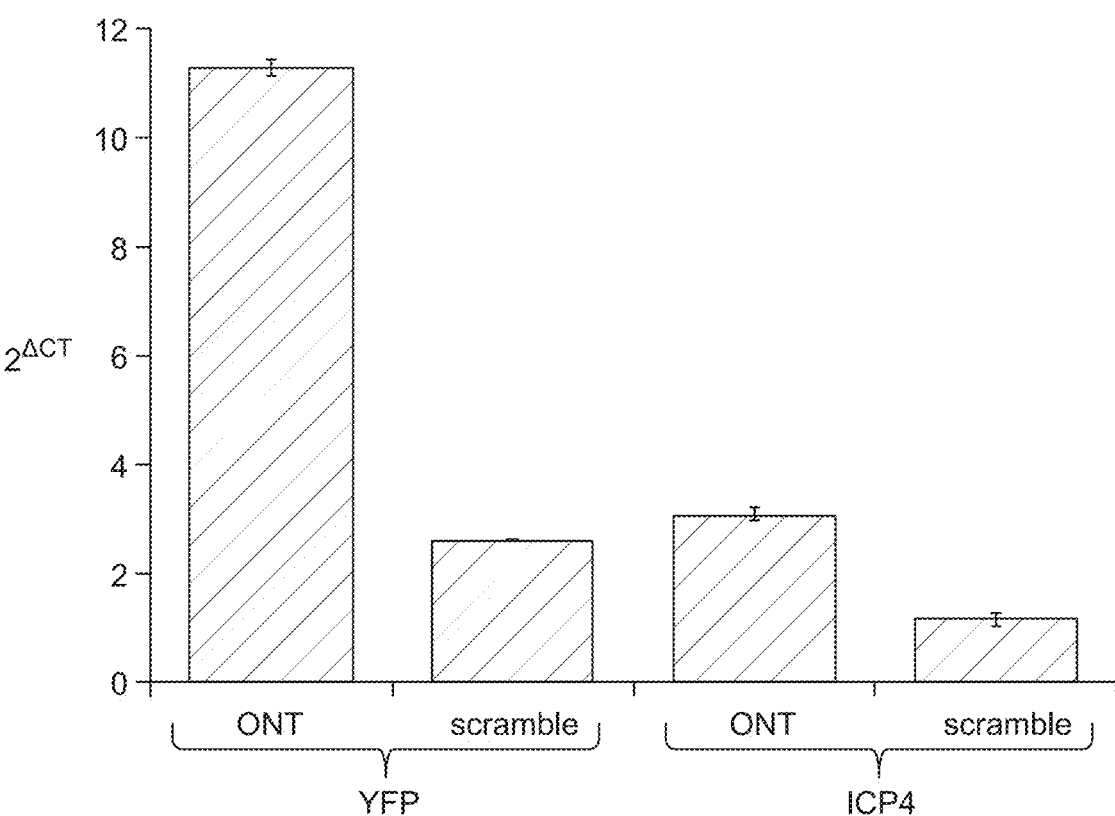

FIG. 6E provides a graph showing that a transcription regulatory circuit disruptor, a double stranded oligonucleotide (ONT) having the sequence CCGAGGACGCCCC-GATCGTCCACACGGAG (SEQ ID NO: 3), interferes with Herpesvirus productive infection in mice.

FIGS. 7A-7G. Feedback circuit disruption interferes with viral replication even at high MOI and limits the evolution of resistance. (a) Flow cytometry of ARPE-19 cells nucleofected with the 28 bp dsDNA that titrates IE86 (C-DOT$^C$) or scrambled dsDNA sequence (C-DOT$^{Scram}$) and infected with a clinically derived CMV (TB40E) encoding an IE86-YFP (MOI=0.1) then analyzed at 2 days post infection (dpi). (b) Flow cytometry of ARPE-19 cells nucleofected with a 29 bp DNA to titrate IE175 (C-DOT$^H$) or scrambled dsDNA sequence (C-DOT$^{Scram}$) and infected with HSV-1 (17syn+ strain) encoding an IE175-YFP (MOI=0.1) then analyzed at 2 dpi. (c) Single-round viral titering of CMV in the presence of 100 μM GCV, PBS, or 25 μM C-DOT$^C$ (or C-DOT$^{Scram}$) at 4-days post infection under different initial MOIs. (d) Single-round viral titering of HSV-1 in presence of 100 μM ACV or 25 μM C-DOT$^H$ (or C-DOT$^{Scram}$) at 4-days post infection under different HSV-1 MOIs. (e) Schematic of the continuous-culture experiment; ARPE-19 cells (+/−C-DOT) were infected with CMV or HSV-1 (0.1 Multiplicity of Infection "MOI") and at 4-day post infection, supernatant was collected and was used to infect naïve ARPE-19 cells +/−C-DOT until day 60. (f) Graph illustrating that disrupting viral transcriptional regulatory circuitry using a double stranded oligonucleotide (ONT) having the sequence GACAGATCGTTTAGTGAACCGTACACGA (SEQ ID NO: 1) constitutes an escape resistant therapeutic strategy in Herpesviruses (HCMV). (g) Graph illustrating that disrupting viral transcriptional regulatory circuitry using a double stranded oligonucleotide (ONT) having the sequence CCGAGGACGCCCCGATCGTCCACACGGAG (SEQ ID NO: 3) constitutes an escape resistant therapeutic strategy in Herpesviruses (HSV-1).

FIGS. 8A-8F. Schematic of the IE86-protein binding assay (a). FPLC chromatography profiles of IE86 protein fragment input and dsDNA input prior to co-incubation (b). Chromatographs of IE86 fragment incubated with either a sequence-scrambled control dsDNA oligonucleotides or ers-containing dsDNA oligonucleotides of differential lengths (c). Schematic of the minimal IE negative-feedback circuit (MIEP-IE86-IRES-GFP) encoded within the feedback-reporter cell line (left) and flow cytometry of feedback reporter cells 48 h after nucleofection with either a 28 bp crs-containing DNA oligonucleotide, a scrambled DNA oligonucleotide (negative control), or mock nucleofection (no DNA oligonucleotide) showing that ers-encoding DNA oligonucleotides disrupt feedback and act as a putative C-DOTs (right) (d). (e)-(f) The 28 bp crs-containing DNA oligonucleotide optimally disrupts feedback and induces cytotoxicity in the feedback-reporter cell line.

Figure 9:
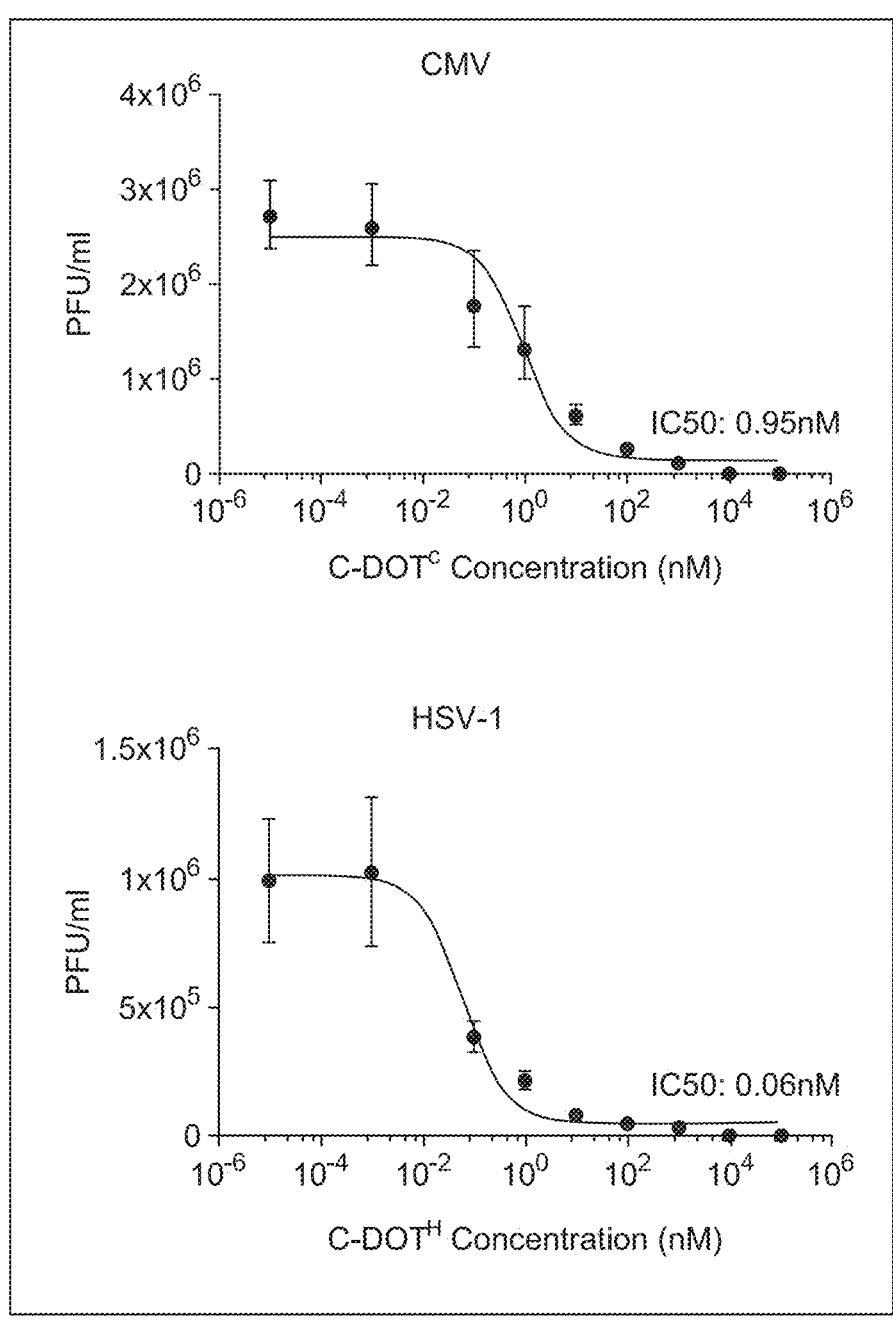

FIG. 9 provides a dose-response analysis in a 96-well plate format. The IC50 is <InM for both CMV and HSV-1 C-DOTs.

Figure 10:
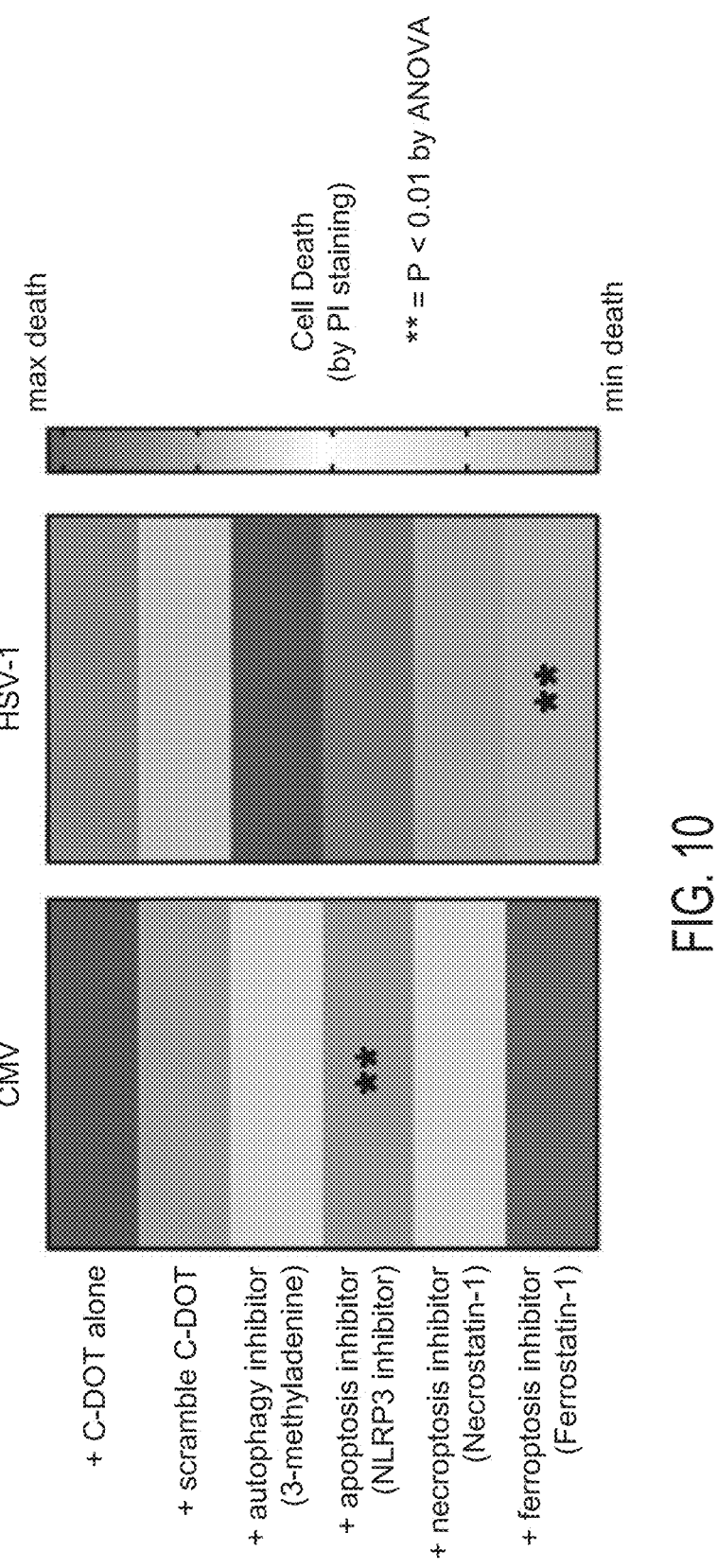

FIG. 10 provides a cell-death pathway analysis (pharmacological inhibitors). The mechanism of C-DOT-induced cell death (in the context of the virus infection) was identified using three separate approaches: (i) RNAseq: to identify misregulated expression patterns and the cell-death pathways these group into (ii) Antibody staining: for specific cell-death pathway markers (iii) Pharmacological inhibitors: of cell-death pathways to test which mitigate C-DOT-induced death. These approaches consistently show that CDOT-induced IE86 and IE175 overexpression, respectively, and cause cytotoxicity through distinct cell-death pathways: CDOT-induced IE86 overexpression causes cell death by apoptosis, whereas CDOT-induced IE175 overexpression causes cell death by ferroptosis (a related regulated death pathway). C-DOT alone caused cell death in CMV and HSV-1. Scramble C-DOT caused minimal cell death in CMV and HSV-1.

FIGS. 11A-11D show simulations and in-vitro analyses indicating that excess crs DNA oligos competitively bind IE86 and would break negative feedback to increase IE86 levels. (SEQ ID NOs: 1 and 19)

Figure 12A:
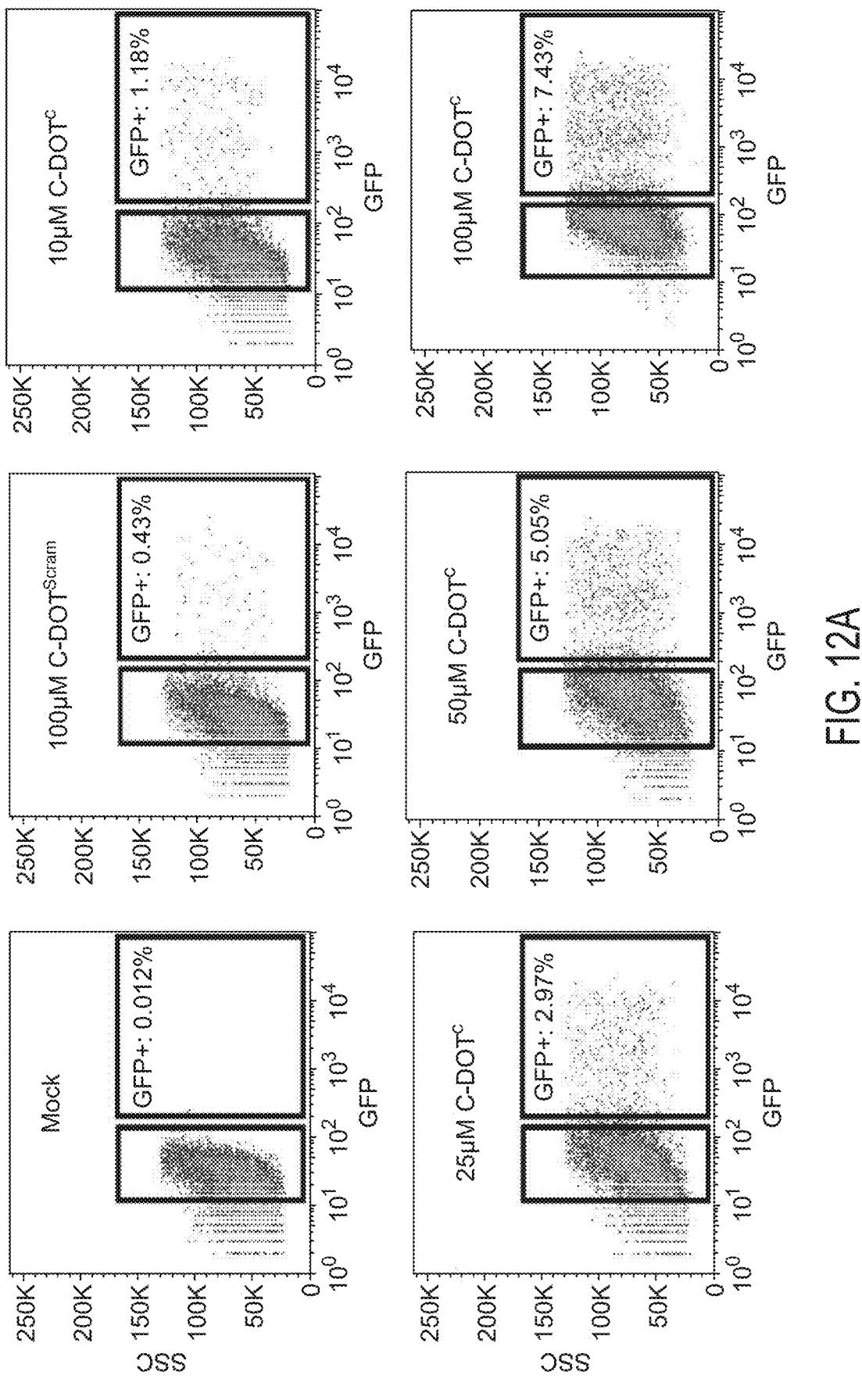
Figure 12B:
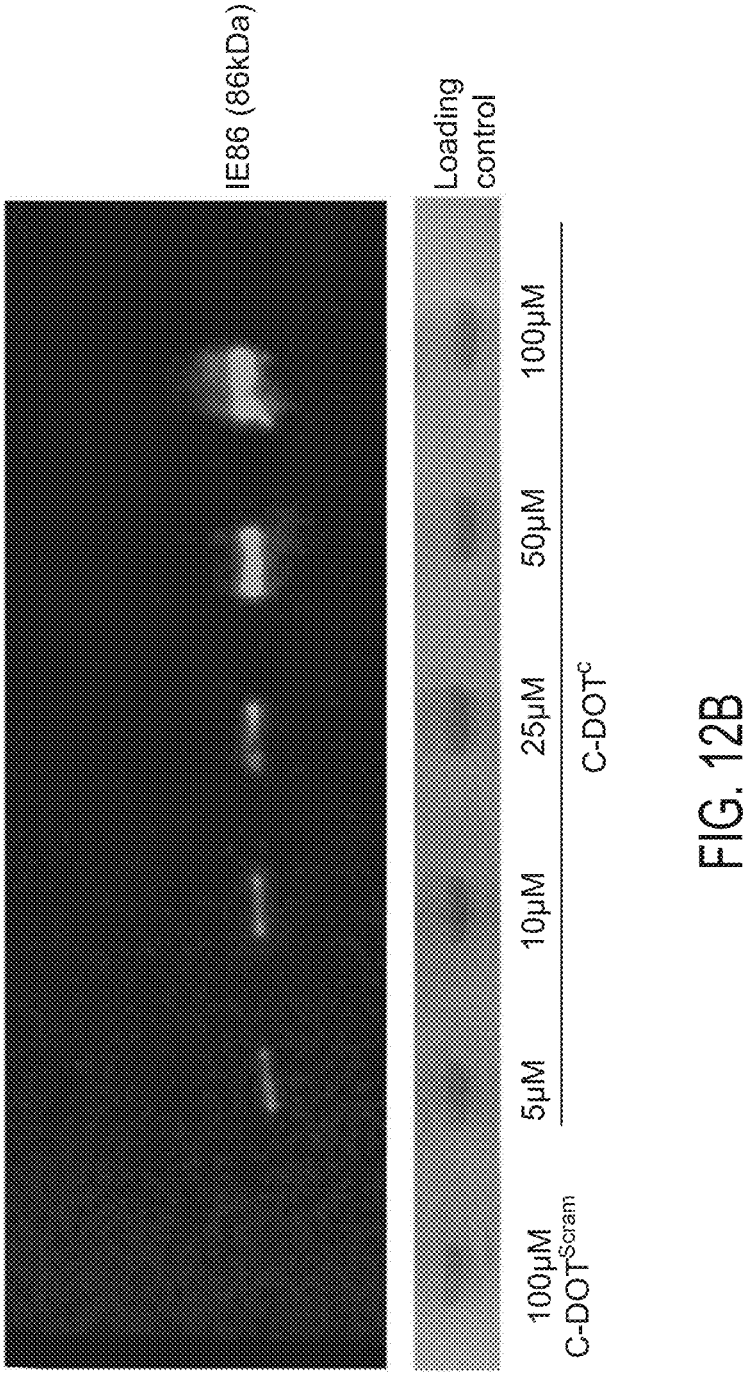
Figure 12C:
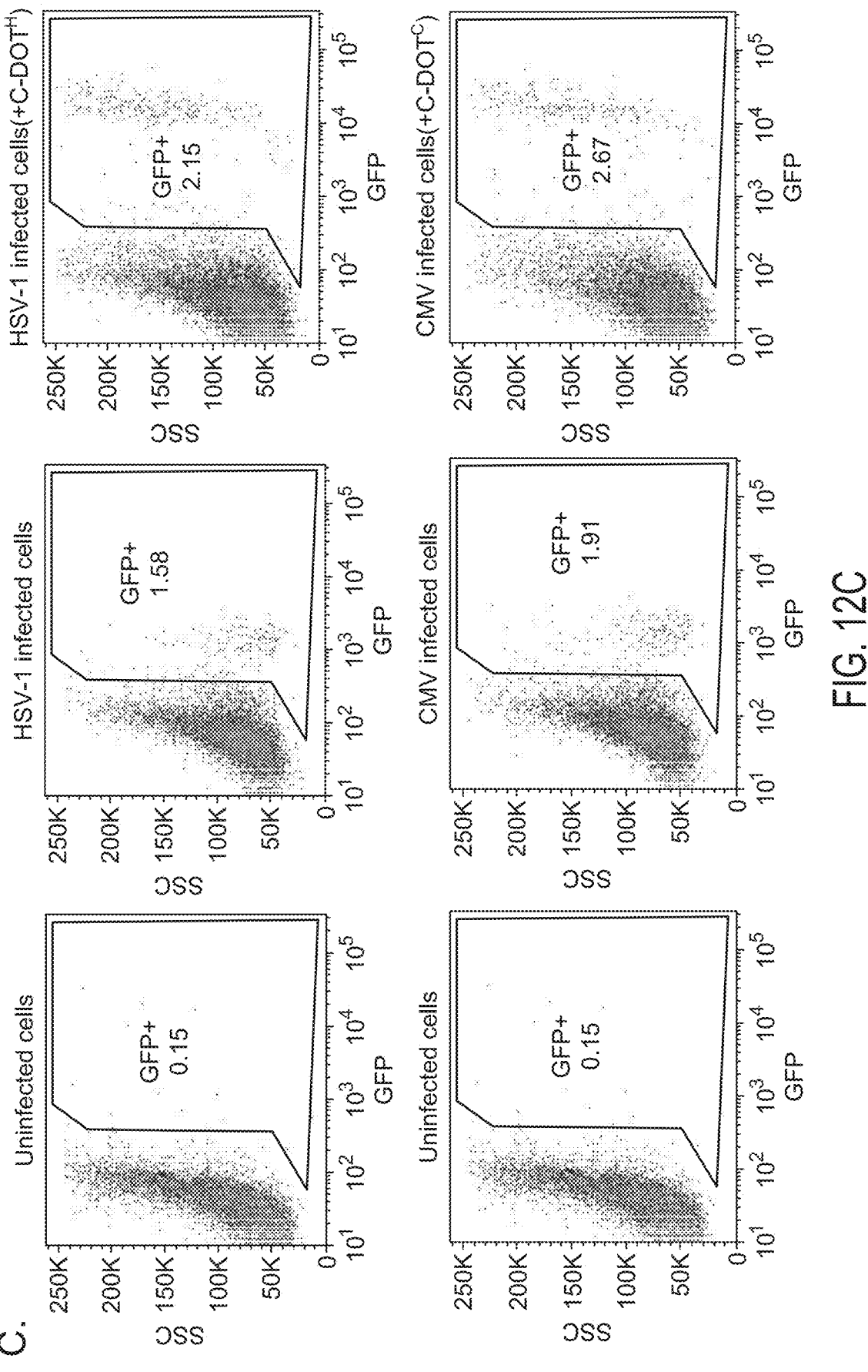

FIGS. 12A-12C show C-DOTs break IE negative feedback in a dose-dependent manner and do not alter cell permissiveness to viral infection.

Figure 13A:
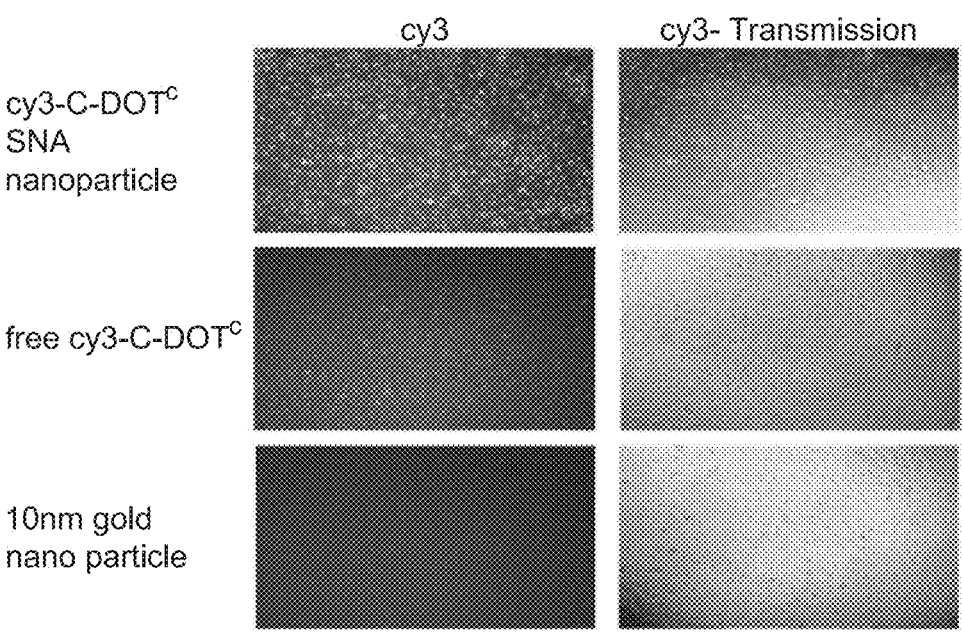
Figure 13B:
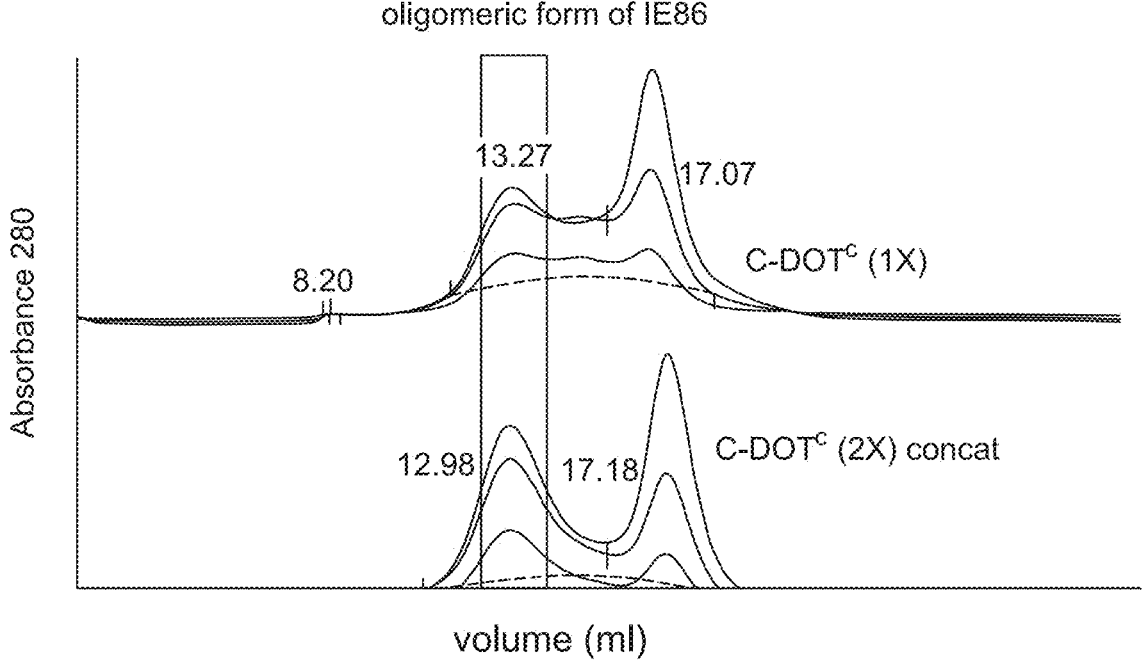
Figure 13C:
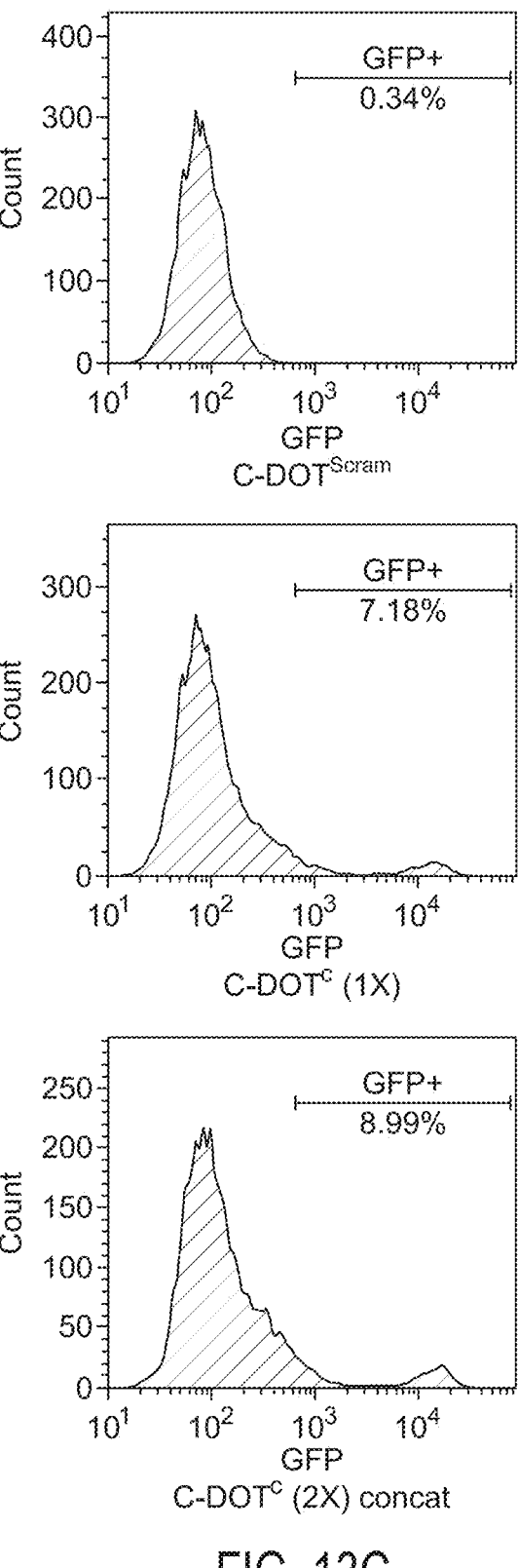
Figure 14D:
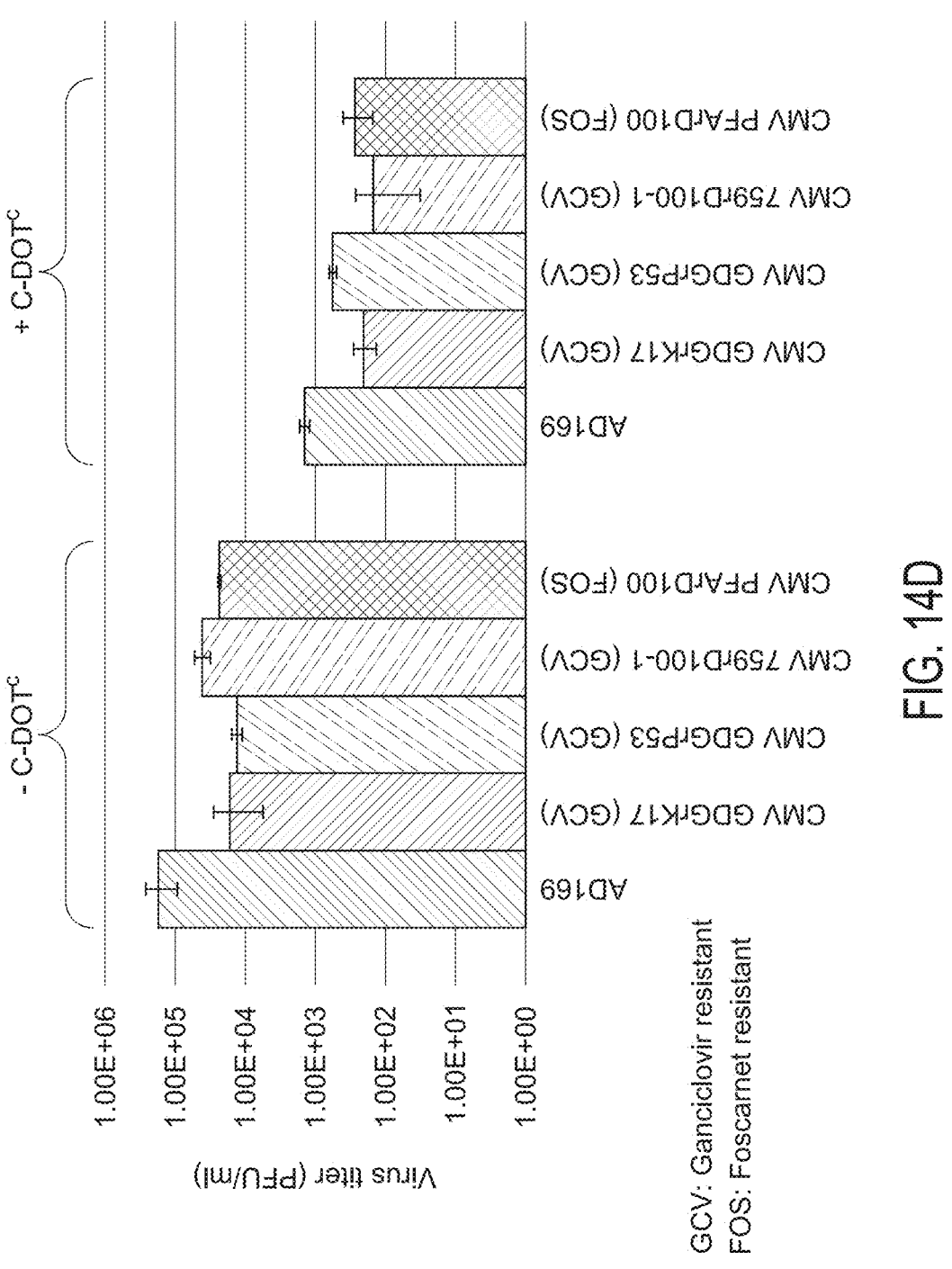

FIGS. 13A-13C show C-DOT nanoparticles enhance cell delivery and C-DOT concatemers enhance IE86 sequestration and feedback disruption.

FIGS. 14A-14D show C-DOTs can be engineered to interfere with a broad range of species-specific herpesviruses including drug-resistant strains. (SEQ ID NOs: 45, 46 and 47)

FIGS. 15A-15F show C-DOTs do not activate innate immune responses in cell lines and—unlike fomivirsen and acyclovir—do not select for resistant viral mutants.

Figure 16A:
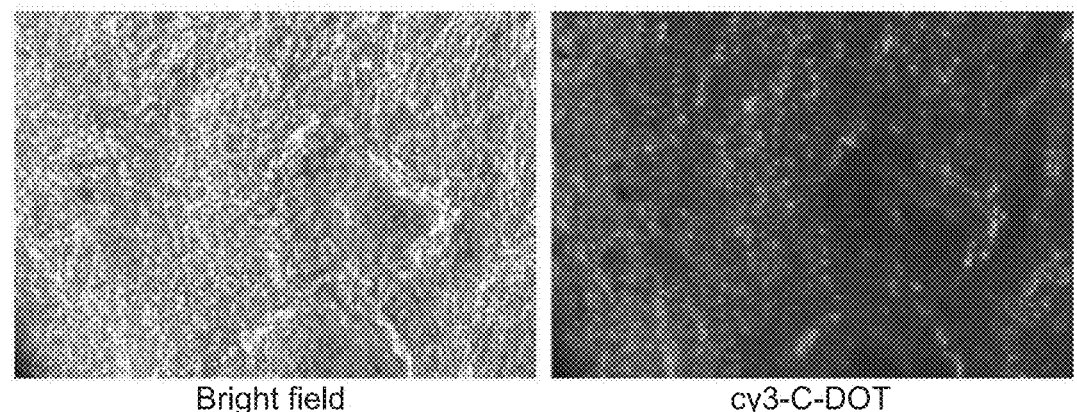
Figure 16B:
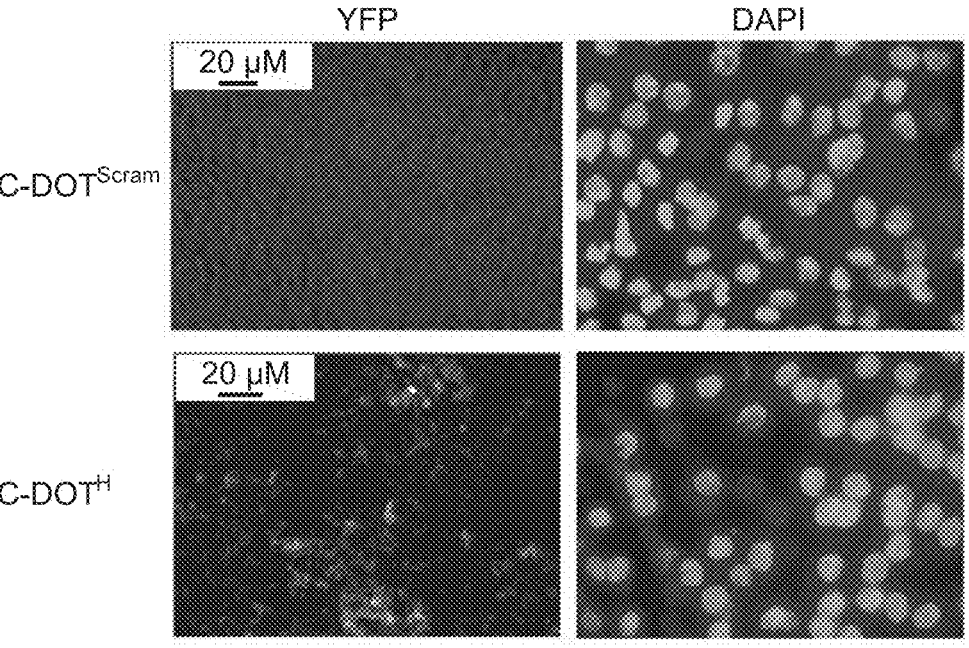
Figure 17A:
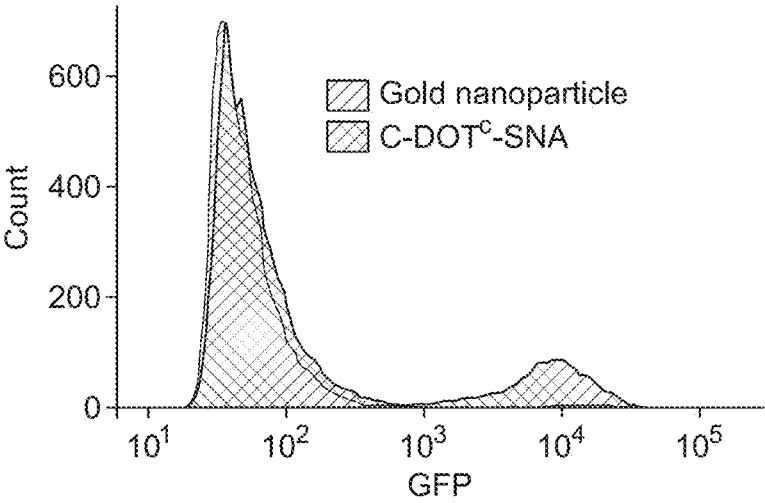
Figure 17B:
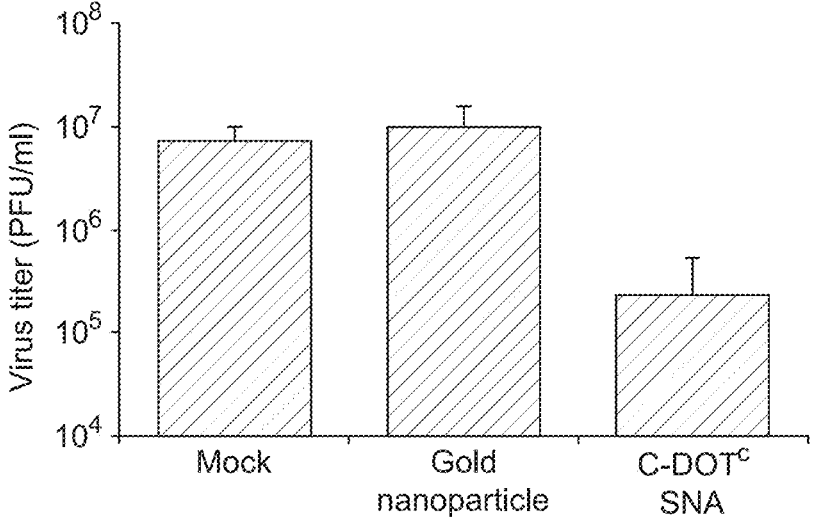
Figure 17C:
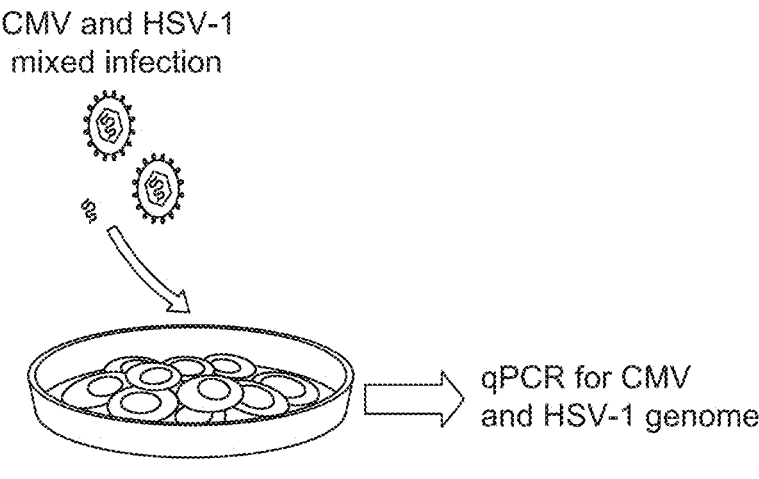
Figure 17D:
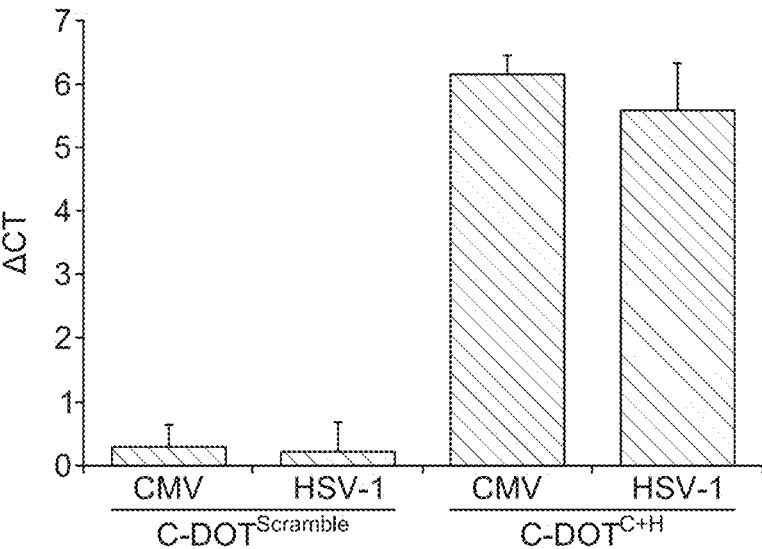

FIGS. 16A-16B show C-DOTs can diffuse into naïve mouse corneal cells and increase IE175 expression in mouse corneas following HSV-1 infection.

FIGS. 17A-17D show nanoparticle C-DOTs efficiently break transcriptional negative feedback and interfere with virus replication and C-DOTs efficiently inhibit virus replication in a mixed infection setting.

Definitions

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones The term "heterologous" refers to two components that are defined by structures derived from different sources. For example, in the context of a polypeptide, a "heterologous" polypeptide may include operably linked amino acid sequences that are derived from different polypeptides (e.g., a first component comprising a recombinant polypeptide and a second component derived from a native GDF15 polypeptide). Similarly, in the context of a polynucleotide encoding a chimeric polypeptide, a "heterologous" polynucleotide may include nucleic acid sequences that includes a first component derived from a first source, e.g., a virus and a second component that has a sequence not present next to the first component in the virus. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). For example, a T7 promoter operably linked to a polynucleotide encoding a GDF15 polypeptide or domain thereof is said to be a heterologous nucleic acid. In the context of recombinant cells, "heterologous" can refer to the presence of a nucleic acid (or gene product, such as a polypeptide) that is of a different genetic origin than the host cell in which it is present. In the context of the DNA molecules disclosed herein the flanking first and second sequences be heterologous to the crs.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

The term "herpesvirus" is well understood in the art, and refers to any member of the family Herpesviridae. Herpesviruses include, e.g., cytomegalovirus (CMV), herpes simplex virus-1 (HSV-1), herpes simplex virus-2 (HSV-2), varicella zoster virus, Epstein-Barr virus (EBV), and Kaposi's sarcoma-associated herpesvirus (KSHV; also known as human herpesvirus-8 or HHV-8).

The term "cytomegalovirus," also known as CMV, refers to a member of the herpesvirus family in any species, including human. CMV is also referred to as a Betaherpesviridae. CMV is a herpesvirus that infects mononuclear cells and lymphocytes.

The term "human cytomegalovirus, or HCMV" indicates a member of the CMV family that infects humans. HCMV is a beta human herpesvirus with a genome size of 230 Kbp, coding more than 70 viral proteins. HCMV is also designated as human herpesvirus 5 (HHV-5). Mouse CMV (mCMV) indicates a member of the CMV family that infects mice. Rhesus monkey CMV (rhCMV) indicates a member of the CMV family that infects rhesus monkeys.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some cases, the individual is a human. In some cases, the individual is a non-human primate.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A "therapeutically effective amount" or "efficacious amount" refers to the amount of a compound that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The disclosures of U.S. Patent Application Publication Nos. US 2017-0360778 A1 and US 2016-0002668 A1 are incorporated by reference herein in their entirety.

It must be noted that as used herein and in the appended claims, the singular forms "a," "an," and "the" include plural referents unless the context clearly dictates otherwise. Thus, for example, reference to "a double stranded DNA molecule" includes a plurality of such compounds and reference to "the composition" includes reference to one or more compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

DETAILED DESCRIPTION

The present disclosure provides a method for inhibiting replication of a herpesvirus in a cell infected with a herpesvirus, the method including contacting the cell with a double stranded DNA molecule including a sequence including a sequence of a cis regulatory sequence (crs) of the herpesvirus, wherein the crs is flanked on the 5' end by a first sequence of at least 2 base pairs and on the 3' end by a second sequence of at least 2 base pairs. Compositions including a double stranded DNA molecule including a sequence including a sequence of a cis regulatory sequence (crs) of a herpesvirus, wherein the crs is flanked on the S' end by a first sequence of at least 2 base pairs and on the 3' end by a second sequence of at least 2 base pairs, are also provided herein. The present disclosure further provides a method of treating a herpesvirus infection in an individual, the method comprising administering to the individual an effective amount of a double stranded DNA molecule including a sequence including a sequence of a cis regulatory sequence (crs) of a herpesvirus, wherein the crs is flanked on the 5' end by a first sequence of at least 2 base pairs and on the 3' end by a second sequence of at least 2 base pairs.

In some cases, one or both of the first sequence of at least 2 base pairs and the second sequence of at least 2 base pairs does not have a DNA sequence of a naturally occurring herpesvirus. In some cases, the herpesvirus is selected from cytomegalovirus (CMV), herpes simplex virus-1 (HSV-1), herpes simplex virus-2 (HSV-2), varicella zoster virus, Epstein-Barr virus (EBV), and Kaposi's sarcoma-associated herpesvirus (KSHV).

In some cases, a double stranded DNA molecule including a sequence of a cis regulatory sequence (crs) of the herpesvirus as described herein inhibits herpesvirus replication by at least 10%, at least 20%, at least 30%, at least 40%, at least 50%, at least 60%, at least 70%, at least 80%, or at least 90%, compared to the level of herpesvirus replication in a herpesvirus-infected cell in the absence of the double stranded DNA molecule. In some cases, a double stranded DNA molecule including a sequence of a cis regulatory sequence (crs) of the herpesvirus as described herein inhibits CMV replication by at least 10%, at least 20%, at least 30%, at least 40%, at least 50%, at least 60%, at least 70%, at least 80%, or at least 90%, compared to the level of CMV replication in a CMV-infected cell in the absence of the double stranded DNA molecule. In some cases, a double stranded DNA molecule including a sequence of a cis regulatory sequence (crs) of the herpesvirus as described herein inhibits HSV-1 replication by at least 10%, at least 20%, at least 30%, at least 40%, at least 50%, at least 60%, at least 70%, at least 80%, or at least 90%, compared to the level of HSV-1 replication in a HSV-1-infected cell in the absence of the double stranded DNA molecule.

In some cases, an effective amount of a double stranded DNA molecule as described herein is an amount that, when administered to an individual in need thereof in monotherapy or combination therapy in one or more administrations, is effective to reduce herpesvirus viral load (e.g., CMV and/or HSV-1) in the individual by at least 10%, at least 20%, at least 30%, at least 40%, at least 50%, at least 60%, at least 70%, at least 80%, or at least 90%, compared to the viral load in the individual before treatment with the double stranded DNA molecule, or in the absence of treatment with the double stranded DNA molecule.

In some cases, an effective amount of a double stranded DNA molecule as described herein is an amount that, when administered to an individual in need thereof in monotherapy or combination therapy in one or more administrations, is effective to reduce the number of herpesvirus (e.g., CMV and/or HSV-1) genome copies in the individual by at least 10%, at least 20%, at least 30%, at least 40%, at least 50%, at least 60%, at least 70%, at least 80%, or at least 90%, compared to the number of herpesvirus genome copies in the individual before treatment with the double stranded DNA molecule, or in the absence of treatment with the double stranded DNA molecule.

In some cases, an effective amount of a double stranded DNA molecule as described herein is an amount that, when administered to an individual in need thereof in monotherapy or combination therapy in one or more administrations, is effective to kill cells infected with herpesvirus (e.g., CMV and/or HSV-1). For example, in some cases, an effective amount of a double stranded DNA molecule as described herein is an amount that, when administered to an individual in need thereof in monotherapy or combination therapy in one or more doses, is effective to kill at least 10%, at least 15%, at least 20%, at least 25%, at least 30%, at least 40%, at least 50%, at least 60%, at least 70%, or more than 70%, of the herpesvirus-infected (e.g., CMV and/or HSV-1) cells in the individual.

In some cases, a double stranded DNA molecule as described herein is administered prior to exposure of the individual to herpesvirus. In some cases, a double stranded DNA molecule is administered after exposure of the individual to herpesvirus. In some cases, a double stranded DNA molecule is administered to an individual who has been diagnosed as having a herpesvirus infection.

In some cases, a double stranded DNA molecule as described herein is administered as monotherapy. In some cases, a double stranded DNA molecule is administered in combination therapy with one or more additional therapeutic agents.

In some cases, a double stranded DNA molecule as described herein is administered to an individual prior to exposure of the individual to CMV. In some cases, a double stranded DNA molecule as described herein is administered to an individual after exposure of the individual to CMV. In some cases, a double stranded DNA molecule as described herein is administered to an individual who has been diagnosed as having a CMV infection.

In some cases, a double stranded DNA molecule as described herein is administered to an individual prior to exposure of the individual to HSV-1. In some cases, a double stranded DNA molecule as described herein is administered to an individual after exposure of the individual to HSV-1. In some cases, a double stranded DNA molecule as described herein is administered to an individual who has been diagnosed as having a HSV-1 infection.

Herpesvirus

The present disclosure provides a composition comprising a double stranded DNA molecule comprising a sequence comprising a sequence of a cis regulatory sequence (crs) of the herpesvirus, wherein the crs is flanked on the 5' end by a first sequence of at least 2 base pairs and on the 3' end by a second sequence of at least 2 base pairs. The flanking sequences can be any suitable length (e.g., 2-7, 2-10, 3-7, 3-10, 4-7, 4-10, 5-7, or 5-10 base pairs or more), limited only by delivery and/or packaging constraints for the DNA. In some cases, the flanking sequences are 7 base pairs or more in length, e.g., 7-10, 10-20, 20-30, 30-40, 40-50, etc. In some cases, one or both of the flanking sequences have a DNA sequence of a naturally occurring herpesvirus, e.g., the DNA sequences present upstream and downstream of the crs. In some cases, one or both of the flanking sequences does not have a DNA sequence of a naturally occurring herpesvirus. In some cases, the herpesvirus is selected from cytomegalovirus (CMV), herpes simplex virus-1 (HSV-1), herpes simplex virus-2 (HSV-2), varicella zoster virus, Epstein-Barr virus (EBV), and Kaposi's sarcoma-associated herpesvirus (KSHV). In some cases, one or both of the flanking sequences have an artificial sequence. Any artificial sequence may be selected, e.g., a random sequence of one or more of the bases G, A, T, C may be selected.

In some embodiments, the herpesvirus is CMV. In some cases, the herpesvirus is HCMV and the sequence of the herpesvirus crs comprises CGTTTAGTGAACCG (SEQ ID NO: 4). In some cases, the sequence of the herpesvirus crs has at least 90% (e.g., 95%, 98%, 99% or 100%) sequence identity to a sequence of the crs of HCMV (e.g., CGTT-TAGTGAACCG (SEQ ID NO: 4)). In some cases, the sequence of the herpesvirus crs flanked on the 5' end by a first sequence of at least 7 base pairs and on the 3' end by a second sequence of at least 7 base pairs comprises GACA-GATCGTTTAGTGAACCGTACACGA (SEQ ID NO: 1). In some cases, the sequence of the herpesvirus ers flanked on the 5' end by a first sequence of at least 7 base pairs and on the 3' end by a second sequence of at least 7 base pairs comprises G*ACAGATCGTT*TAGTGAACC*GTACACG*A (SEQ ID NO: 5), wherein * is a phosphorothioated bond.

In some cases, the herpesvirus is Rhesus CMV (RhCMV). In some cases, the sequence of the herpesvirus ers comprises CGTTTAGGGAACCG (SEQ ID NO: 6). In some cases, the sequence of the herpesvirus crs has at least 90% (e.g., 95%, 98%, 99% or 100%) sequence identity to a sequence of the crs of RhCMV (e.g., CGTTTAGGGAACCG (SEQ ID NO: 6)). In some cases, the sequence of the herpesvirus crs flanked on the 5' end by a first sequence of at least 7 base pairs and on the 3' end by a second sequence of at least 7 base pairs comprises GACAGATCGTTTAGG-GAACCGTACACGA (SEQ ID NO: 7). In some cases, the sequence of the herpesvirus crs flanked on the 5' end by a first sequence of at least 7 base pairs and on the 3' end by a second sequence of at least 7 base pairs comprises G*ACAGATCGT*TTAGGGAAC*CGTACACG*A (SEQ ID NO: 8), wherein * is a phosphorothioated bond.

In some cases, the herpesvirus is Mouse CMV (MCMV). In some cases, the sequence of the herpesvirus crs comprises CAGCGTCGGTACCG (SEQ ID NO: 9). In some cases, the sequence of the crs has at least 90% (e.g., 95%, 98%, 99% or 100%) sequence identity to a sequence of the crs of MCMV (e.g., CAGCGTCGGTACCG (SEQ ID NO: 9)). In some cases, the sequence of the herpesvirus crs flanked on the 5' end by a first sequence of at least 7 base pairs and on the 3' end by a second sequence of at least 7 base pairs comprises GACAGACCAGCGTCGGTACCGTACACGA (SEQ ID NO: 2). In some cases, the sequence of the herpesvirus crs flanked on the 5' end by a first sequence of at least 7 base pairs and on the 3' end by a second sequence of at least 7 base pairs comprises G*ACAGACCA*GCGTCGG*TACCGTACACG*A (SEQ ID NO: 9), wherein * is a phosphorothioated bond.

In some other cases, the herpesvirus is HSV-1. In some cases, the sequence of the herpesvirus crs comprises CGCCCCGATCGTCCA (SEQ ID NO: 10). In some cases, the sequence of the herpesvirus crs has at least 90% (e.g., 95%, 98%, 99% or 100%) sequence identity to a sequence of the crs of HSV-1 (e.g., CGCCCCGATCGTCCA (SEQ ID NO: 10)). In some cases, the sequence of the herpesvirus crs flanked on the 5' end by a first sequence of at least 7 base pairs and on the 3' end by a second sequence of at least 7 base pairs comprises CCGAGGACGCCCCGATCGTC-CACACGGAG (SEQ ID NO: 3). In some cases, the sequence of the herpesvirus crs flanked on the 5' end by a first sequence of at least 7 base pairs and on the 3' end by a second sequence of at least 7 base pairs comprises CCG*AGGAC*GCCCCGATC*GTCCACACG*GAG (SEQ ID NO: 11), wherein * is a phosphorothioated bond.

Reducing Herpesvirus in Transplant Organs and Tissues

The present disclosure provides a method of inhibiting herpesvirus replication in an organ or tissue, the method comprising contacting the organ or tissue in vitro or ex vivo with a double stranded DNA molecule including a sequence comprising a sequence of a cis regulatory sequence (crs) of the herpesvirus, wherein the crs is flanked on the 5' end by a first sequence of at least 2 base pairs and on the 3' end by a second sequence of at least 2 base pairs. In some cases, the herpesvirus is CMV. In some cases, the herpesvirus is HSV-1. In some cases, the individual is a human. In some cases, the method includes administering at least a second therapeutic agent. In some cases, the second therapeutic agent is ganciclovir, foscarnet, cidofovir, maribavir, or val-ganciclovir. In some cases, the second therapeutic agent is an HDAC inhibitor. In some cases, the individual is an organ transplant recipient. In some cases, the individual is a bone marrow transplant recipient. In some cases, the individual does not have a herpesvirus infection, and is a prospective organ transplant recipient. In some cases, the individual does not have a herpesvirus infection, and is a prospective bone marrow transplant recipient. In some cases, the individual is a pregnant female. In some cases, the individual is a neonate.

The present disclosure provides a method of reducing the amount of CMV (e.g., reducing the number of genome copies of CMV) in an organ or tissue, the method comprising contacting the organ or tissue in vitro or ex vivo with a double stranded DNA molecule including a sequence comprising a sequence of a cis regulatory sequence (crs) of the CMV, wherein the crs is flanked on the 5' end by a first sequence of at least 2 base pairs and on the 3' end by a second sequence of at least 2 base pairs. In some cases, the organ or tissue is autologous (the organ or tissue is obtained from a donor, where the donor is also the recipient of the organ or tissue). In some cases, the organ or tissue is allogeneic (the organ or tissue is obtained from a genetically different donor of the same species as the recipient). In some cases, the organ or tissue is xenogeneic (the organ or tissue is obtained from a different species from the recipient).

Organs and tissues suitable for use in a subject method include, but are not limited to, a kidney, a liver, a pancreas, a heart, a lung, skin, blood tissue (including whole blood; red blood cells; white blood cells; cord blood; and the like, where the blood tissue may comprise an isolated population of blood cells (buffy coat; red blood cells; platelets; lymphocytes; T cells; B cells; or some other population), or where the blood tissue comprises a mixed population of cells), small intestine, an endothelial tissue, a vascular tissue (e.g., a blood vessel), an eye, a stomach, a thymus, bone, bone marrow, cornea, a heart valve, an islet of Langerhans, or a tendon. As used herein, "organ" encompasses a whole organ or a part of an organ. As used herein, "tissue" encompasses a whole tissue or part of a tissue. As used herein, "tissue" encompasses a cell population.

In some cases, the organ or tissue is contacted in vitro or ex vivo with the double stranded DNA molecule for a period of time of from about 15 minutes to about 48 hours, or more than 48 hours. For example, in some cases, the organ or tissue is contacted in vitro or ex vivo with the double stranded DNA molecule for a period of time of from 15 minutes to 1 hour, from 1 hour to 2 hours, from 2 hours to 4 hours, from 4 hours to 8 hours, from 8 hours to 12 hours, from 12 hours to 24 hours, from 24 hours to 48 hours, or more than 48 hours.

In some cases, the organ or tissue is contacted in vitro or ex vivo with the double stranded DNA molecule in an amount and for a period of time to reduce the CMV genome copies in the organ or tissue. In some cases, an effective amount of a double stranded DNA molecule is an amount that, when contacted with an organ or tissue, is effective to reduce the number of CMV genome copies in the organ or tissue by at least 10%, at least 20%, at least 30%, at least 40%, at least 50%, at least 60%, at least 70%, at least 80%, or at least 90%, compared to the number of CMV genome copies in the organ or tissue before contacting with the double stranded DNA molecule, or in the absence of contacting with the double stranded DNA molecule. In some cases, an effective amount of a double stranded DNA molecule is an amount that, when contacted with an organ or tissue for a period of time of from about 2 hours to 48 hours, is effective to reduce the number of CMV genome copies in the organ or tissue by at least 10%, at least 20%, at least 30%, at least 40%, at least 50%, at least 60%, at least 70%, at least 80%, or at least 90%, compared to the number of CMV genome copies in the organ or tissue before contacting with the double stranded DNA molecule, or in the absence of contacting with the double stranded DNA molecule.

In some cases, the organ or tissue is contacted in vitro or ex vivo with the double stranded DNA molecule in a liquid medium. The liquid medium can comprise, in addition to the double stranded DNA molecule, one or more of a buffer, a salt, a preservative, etc. In some cases, the liquid medium comprises, in addition to the double stranded DNA molecule, one or both of an HDAC inhibitor, and a transcriptional transactivator.

Modified Oligonucleotides

The oligonucleotides of the present disclosure may be modified to modulate various properties of the oligonucleotides, e.g., increase half-life and/or to facilitate delivery of the oligonucleotides into cells.

In some cases, the oligonucleotides of the present disclosure are modified to increase their uptake into a cell, e.g., cell permeability of the oligonucleotides may be increased by the modification(s). The oligonucleotides may be conjugated to any suitable moiety that increases their permeability through a cell membrane, such as, one or more lipid moieties.

In certain embodiments, the oligonucleotides of the present disclosure are modified to include various nucleic acid analogs without modification to the sequence of the respective oligonucleotides. Suitable analogs include, but are not limited to, peptide nucleic acids (PNAs), locked nucleic acids (LNAs), bridged nucleic acids (BNAs), and the like.

In some cases, the oligonucleotides of the present disclosure include a modified backbone. In some cases, the oligonucleotides are modified to increase their half-life. Suitable modifications include, e.g., phosphorothioate linkages, phosphorodithioate linkages, methylphosphonate linkages, phosphoramidate linkages, 2'-modifications (e.g., modifications of the 2' position with methyl and methoxyethyl groups), and the like.

In another aspect, the oligonucleotides of the present disclosure may be modified to facilitate delivery of the oligonucleotides. In some cases, the oligonucleotides are conjugated to or encapsulated by a moiety that facilitates the delivery of the oligonucleotides. Suitable moieties include delivery vehicles such as, nanoparticles, vesicles, liposomes, micelles, dendrimers, viral particles, microbeads, and the like.

Subjects Suitable for Treatment

Subjects suitable for treatment with a method of the present disclosure for treating a herpesvirus infection include individuals who have been diagnosed as having a herpesvirus infection. Subjects suitable for treatment with a method of the present disclosure for treating a herpesvirus infection include individuals who have not been diagnosed as having a herpesvirus infection. In some cases, the individual does not have a herpesvirus infection, but is at greater risk than the general population of contracting a herpesvirus infection.

In some cases, the individual has a herpesvirus infection, and also has an immunodeficiency virus (e.g., human immunodeficiency virus, HIV) infection. In some cases, the individual does not have an immunodeficiency virus (e.g., human immunodeficiency virus; HIV) infection.

In some cases, the individual is an organ transplant recipient. In some cases, the individual is a liver transplant recipient. In some cases, the individual is a kidney transplant recipient. In some cases, the individual is a liver transplant recipient. In some cases, the individual is a bone marrow transplant recipient. In some cases, the individual is a lung transplant recipient.

In some cases, the individual does not have a herpesvirus infection; and is a prospective organ transplant recipient. In some cases, the individual does not have a herpesvirus infection; and is a prospective liver transplant recipient. In some cases, the individual does not have a herpesvirus infection; and is a prospective kidney transplant recipient. In some cases, the individual does not have a herpesvirus infection; and is a prospective bone marrow transplant recipient. In some cases, the individual does not have a herpesvirus infection; and is a prospective lung transplant recipient.

In some cases, the individual is a pregnant female, e.g., a pregnant human female. In some cases, the individual is a neonate, e.g., a human neonate. In some cases, the individual is from 1 hour old to 4 weeks old, e.g., from 1 hour to 4 hours, from 4 hours to 8 hours, from 8 hours to 12 hours, from 12 hours to 1 day, from 1 day to 1 week, or from 1 week to 4 weeks, old. In some cases, the individual is from 4 weeks old to 6 months old.

Compositions and Formulations

An active agent is administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For the purposes of the following description of formulations, "active agent" includes an active agent as described above, and optionally one or more additional therapeutic agent.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an active is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

In certain aspects, the compositions and/or formulations may include at least two, at least three, at least four, or more of the different DNA molecules provided herein. For example, a composition may include a) a first double stranded DNA molecule comprising a HSV crs from a first HSV and b) a second double stranded DNA molecule comprising a HSV crs from a second HSV. The first and second HSVs may be selected independently from HSV-1, HSV-2, and CMV.

In some cases, a composition may include: a) a first double stranded DNA molecule comprising a HSV ers from a first HSV; b) a second double stranded DNA molecule comprising a HSV crs from a second HSV; and c) a third double stranded DNA molecule comprising a HSV crs from a third HSV. The first, second, and third HSVs may be selected from HSV-1, HSV-2, and CMV.

Dosages

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Where two different active agents are administered, a first active agent and a second active agent can be administered in separate formulations. A first active agent and a second active agent can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. An active agent can also be delivered to the subject by enteral administration, e.g., oral administration.

Combination Therapy

In some cases, a method of the present disclosure for treating a herpesvirus infection in an individual comprises administering to the individual, in combined effective amounts: a) a double stranded DNA molecule as described herein; and b) at least a second therapeutic agent. Suitable second therapeutic agents include, but are not limited to, ganciclovir, foscarnet, cidofovir, maribavir, valganciclovir, and intravenous immunoglobulin (IVIG). Suitable second agents include, but are not limited to, histone deacetylase (HDAC) inhibitors. Suitable second agents include, but are not limited to, transcriptional transactivators Suitable transcriptional transactivators include, e.g., protein kinase C agonists, prostratin; TNF-alpha; 12-deoxyphorbol 13-phenylacetate (DPP); protein-based therapeutic agents that act through related cell-signaling pathways (e.g., the HSV-1 VP16 transactivator); and the like. In some cases, the transcriptional transactivator is prostratin. In some cases, the transcriptional transactivator is TNF-$\alpha$. In some cases, the transcriptional transactivator is a prostratin analog as described in U.S. Pat. No. 8,067,632.

HDAC inhibitors are known in the art, and any of a variety of HDAC inhibitors can be used. In some cases, the HDAC inhibitor inhibits all Class I HDACs, but does not substantially inhibit any Class II HDAC or any Class III HDAC. In some cases, the HDAC inhibitor specifically inhibits HDAC1 (and does not substantially inhibit other HDAC polypeptides, e.g., does not substantially inhibit HDAC 2, 3, 4, 5, 6, 7, 8, 9, or 10, or any Class III HDAC). In some cases, the HDAC inhibitor specifically inhibits HDAC2 (and does not substantially inhibit other HDAC polypeptides, e.g., does not substantially inhibit HDAC 1, 3, 4, 5, 6, 7, 8, 9, or 10, or any Class III HDAC). In some cases, the HDAC inhibitor inhibits both HDAC1 and HDAC2, but does not substantially inhibit other HDAC polypeptides, e.g., does not substantially inhibit HDAC 3, 4, 5, 6, 7, 8, 9, or 10, or any Class III HDAC.

Examples of HDAC inhibitors include trichostatin A (TSA) ((R,2E,4E)-7-(4-(dimethylamino)phenyl)-N-hydroxy-4,6-dimethyl-7-oxohepta-2,4-dienamide); suberoylanilide hydroxamic acid (SAHA); sulfonamides such as oxamflatin ((E)-N-hydroxy-5-(3-(phenylsulfonamido) phenyl) pent-2-en-4-ynamide); and belinostat (PXD101) ((E)-N-hydroxy-3-(4-(N-phenylsulfamoyl) phenypacrylamide). Other hydroxamic-acid-sulfonamide inhibitors of histone deacetylase are described in: Lavoie et al. (2001) Bioorg. Med. Chem. Lett. 11:2847-50; Bouchain et al. (2003) J. Med. Chem. 846:820-830; Bouchain et al. (2003) Curr. Med. Chem. 10:2359-2372; Marson et al. (2004) Bioorg. Med. Chem. Lett. 14:2477-2481; Finn et al. (2005) Helv. Chim. Acta 88:1630-1657; WO2002030879; WO2003082288; WO20050011661; WO2005108367; WO2006123121; WO2006017214; WO2006017215; and US2005/0234033. Other structural classes of histone deacetylase inhibitors include short chain fatty acids, cyclic peptides, and benzamides. Acharya et al. (2005) Mol. Pharmacol. 68:917-932.

In some cases, the HDAC inhibitor is a short-chain fatty acid, e.g., a butyrate or a phenylbutyrate. In some cases, the HDAC inhibitor is an epoxyketone-containing cyclic tetrapeptide, e.g. trapoxin. In some cases, the HDAC inhibitor is a non-epoxyketone-containing cyclic tetrapeptide. In some cases, the HDAC inhibitor is a hydroxamic acid, e.g., SAHA. In some cases, the HDAC inhibitor is a benzamide. In some cases, the HDAC inhibitor is valproate. In some cases, the HDAC inhibitor is TSA. In some cases, the HDAC inhibitor is PXD101.

Further examples of HDAC inhibitors include those disclosed in, e.g., Dokmanovic et al. (2007) Mol. Cancer. Res. 5:981; U.S. Pat. Nos. 7,642,275; 7,683,185; 7,732,475; 7,737,184; 7,741,494; 7,772,245; 7,795,304; 7,799,825; 7,803,800; 7,842,727; 7,842,835; U.S. Patent Publication No. 2010/0317739; U.S. Patent Publication No. 2010/0311794, U.S. Patent Publication No. 2010/0310500; U.S. Patent Publication No. 2010/0292320; and U.S. Patent Publication No. 2010/0291003. In some cases, a given HDAC inhibitor or class of HDAC inhibitors is specifically excluded.

In some cases, a method of the present disclosure for treating a herpesvirus infection in an individual comprises administering to the individual, in combined effective amounts: a) a first double stranded DNA molecule comprising a HSV crs from a first HSV and b) a second double stranded DNA molecule comprising a HSV crs from a second HSV. The first and second HSVs may be selected independently from HSV-1, HSV-2, and CMV.

In some cases, a method of the present disclosure for treating a herpesvirus infection in an individual comprises administering to the individual, in combined effective amounts: a) a first double stranded DNA molecule comprising a HSV crs from a first HSV; b) a second double stranded DNA molecule comprising a HSV crs from a second HSV;

and c) a third double stranded DNA molecule comprising a HSV crs from a third HSV. The first, second, and third HSVs may be selected from HSV-1, HSV-2, and CMV.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular (ly); i.p., intraperitoneal (ly); s.c., subcutaneous (ly); and the like.

Example 1

A novel approach that disrupts viral auto-regulatory circuits with a DNA molecule and limits resistance by requiring multiple viral mutations is provided. DNA-based circuit-disruptor oligonucleotide therapies (C-DOTs) that exploit this mechanism by interfering with transcriptional negative feedback in human herpesviruses (CMV and HSV-1) thereby increasing viral transcription factors to cytotoxic levels are disclosed. C-DOTs reduce viral replication >100-fold, prevent emergence of resistant mutants in continuous culture, are effective in high-viremic conditions where existing antivirals are ineffective, and show efficacy in mice. Strikingly, no C-DOT-resistant mutants evolved in >60 days of culture, in contrast to approved herpesvirus antivirals where resistance rapidly evolved. Overall, the results demonstrate that oligonucleotide therapies targeting feedback circuits are escape resistant and could have broad therapeutic applicability to viruses, microbes, and neoplastic cells.

The time to emergence of drug-resistant 'escape' mutants is typically estimated from the mutation rate, $\mu$, and the effective population size, $N^{8,9}$. Many viruses exhibit large u such that frequency of mutants ($\mu \times N$) is >1, even for moderate virus population sizes (e.g., if $\mu \sim 10^5$ then for $\mu \times N > I$ requires only that $N > 10^5$). Herpesviruses, for example, exhibit high mutation rates[10,11], which may explain the substantial antiviral resistance observed in clinical settings[4,5]. In particular, herpes simplex virus type 1 (HSV-1)—a leading cause of blindness—exhibits resistance to acyclovir (ACV) in ~40% of transplant patients[6] while human herpesvirus 5, cytomegalovirus (CMV)—a leading cause of birth defects and transplant failure—exhibits resistance to ganciclovir (GCV) in 30-75% of patients[7]. ACV and GCV resistance arises because their antiviral activity requires herpesvirus thymidine kinase (TK), and single-base mutations destroy TK activity (with a u $\sim 10^{-3})^{10}$ driving TK escape mutants within a single generation[12], which ultimately led to the development of non-TK drug targets[13,14]. Resistance to these new therapies is still being clinically evaluated, but, given the generality of resistance to antimicrobials[1-3], is likely unavoidable.

Figure 1:
FIG. 1 depicts congenital infection, CMV retinitis, and infection in solid organ transplant as a result of CMV infection.
Figure 1:
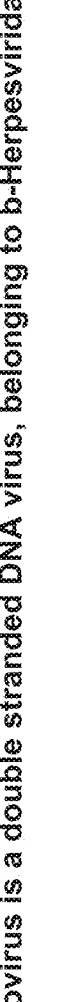
Figure 1:
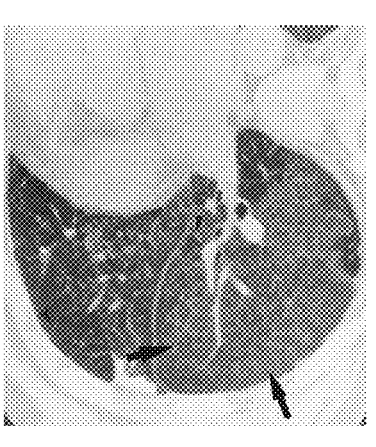
Figure 1:
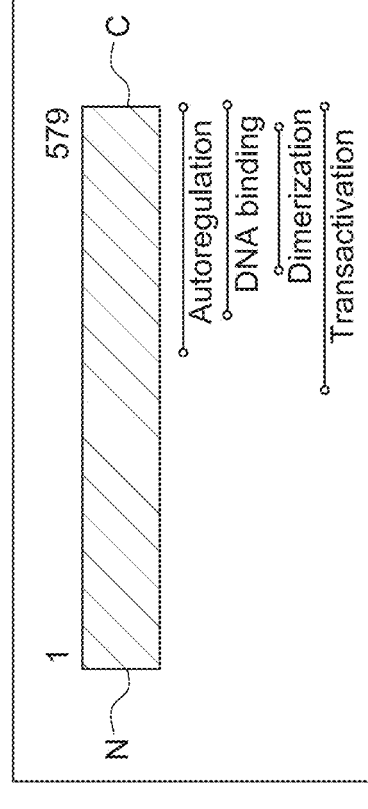
Figure 2A:
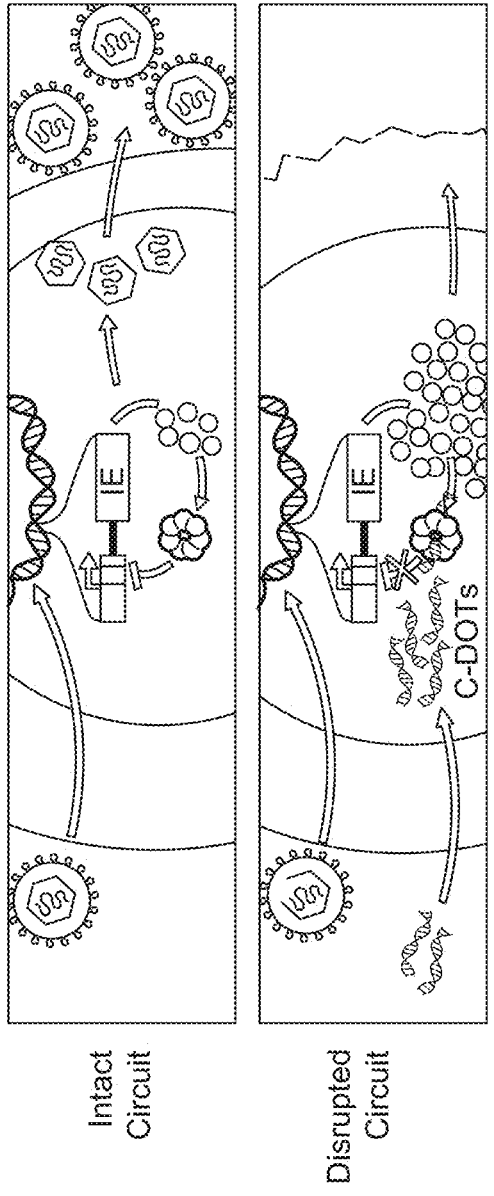
FIGS. 2A-2C provide a schematic depicting human cytomegalovirus (HCMV) transcriptional feedback circuits and their potential as escape-resistant drug targets (a); a graph showing an IE2-Oligo competition model (b); and calculations for the 50% emergence time of resistance mutants as a function of the mutation rate $\mu$ (c).

Combination therapy, wherein multiple drugs simultaneously inhibit different viral targets, is one approach used to limit antiviral resistance. For a two-drug therapy, escape mutants are predicted to arise at a rate $\sim \mu^2$ (i.e., the requirement for mutants to arise becomes $\mu^2 N > 1$), which requires substantially larger virus populations (i.e., $N > \mu^2$). However, each constituent antiviral must have a distinct molecular target, as well as favorable toxicity, efficacy, bioavailability, and dosing profiles. These criteria can be challenging to satisfy and such targets are still being characterized for herpesviruses. One proposed alternative has been to mimic the evolutionary benefits of combination therapy by inhibiting protein-protein or protein-DNA interactions with a single molecule; this has remained technically challenging but transcriptional auto-regulatory (feedback) circuits present an attractive target for this approach[15]. Both CMV and HSV-1 utilize transcriptional feedback to regulate immediate-early (IE) viral gene expression, which is obligate to transactivate downstream viral genes, ultimately licensing virus maturation[16-19]. In CMV, the 86-kDa immediate early (IE86; a.k.a. IE2) protein, and in HSV-1 the IE175 (a.k.a. ICP4) protein, are indispensable transcriptional transactivators[20,21]. Critically, IE86 and IE175 are cytotoxic when expression is misregulated above tightly auto-regulated homeostatic levels, and both CMV and HSV-1 encode negative-feedback circuits to maintain IE86 and IE175 levels below their respective cytotoxic thresholds[20,22]. These feedback circuits are comprised of a protein-DNA interaction wherein the IE protein binds to a 14-15 bp palindromic cis-repression sequence (crs) within its respective promoter and auto-represses its own transcription (FIG. 2a). Disrupting this feedback by altering the crs increases IE protein levels to cytotoxic levels, leading to a >100-fold reduction in viral replication[22,23].

Figure 2B:
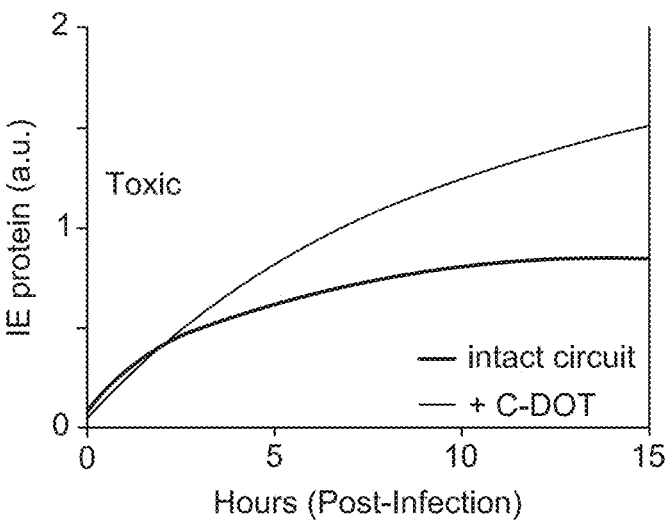
Figure 2C:
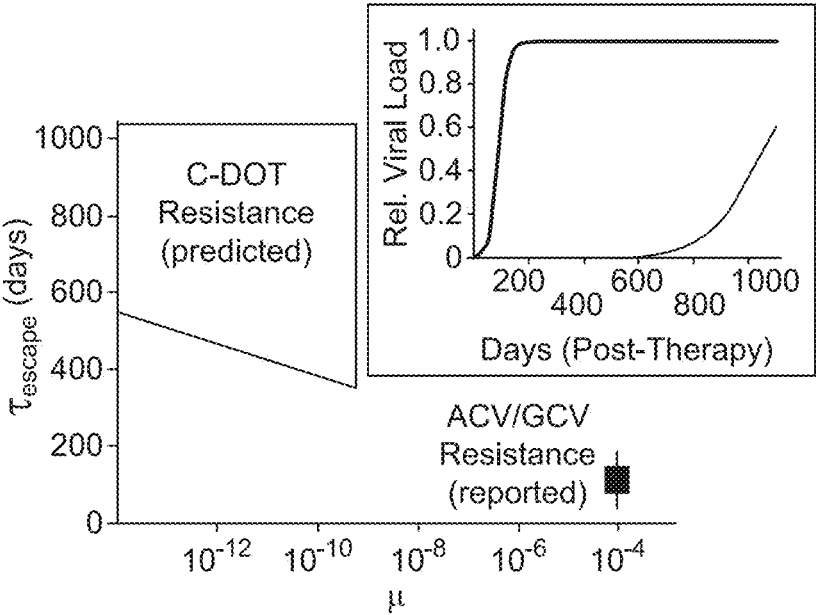
Figure 3A:
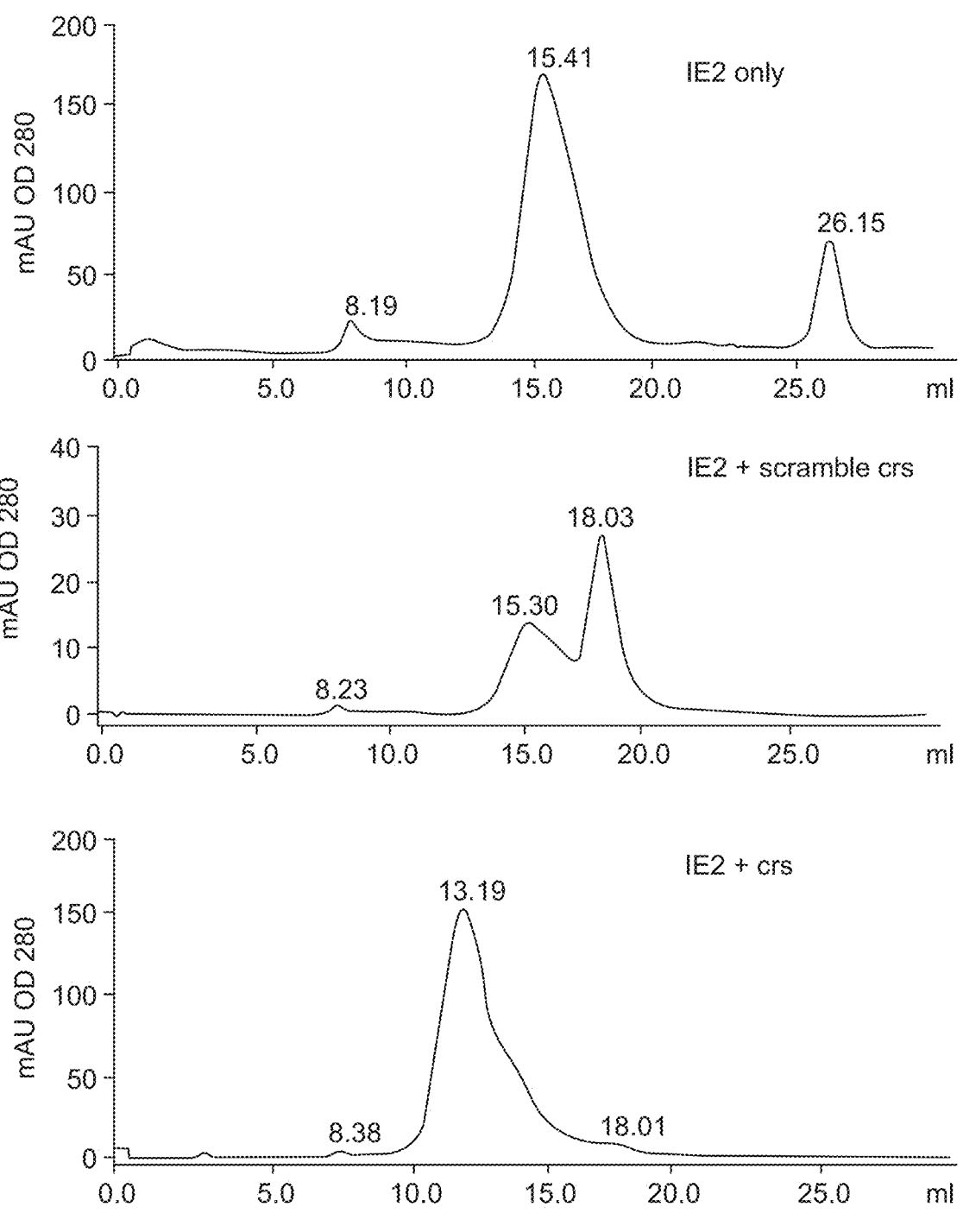
FIG. 3A provides graphs illustrating IE2 oligomerization by a double stranded oligonucleotide (ONT) having the sequence GACAGATCGTTTAGTGAACCGTACACGA (SEQ ID NO: 1).
Figure 3B:
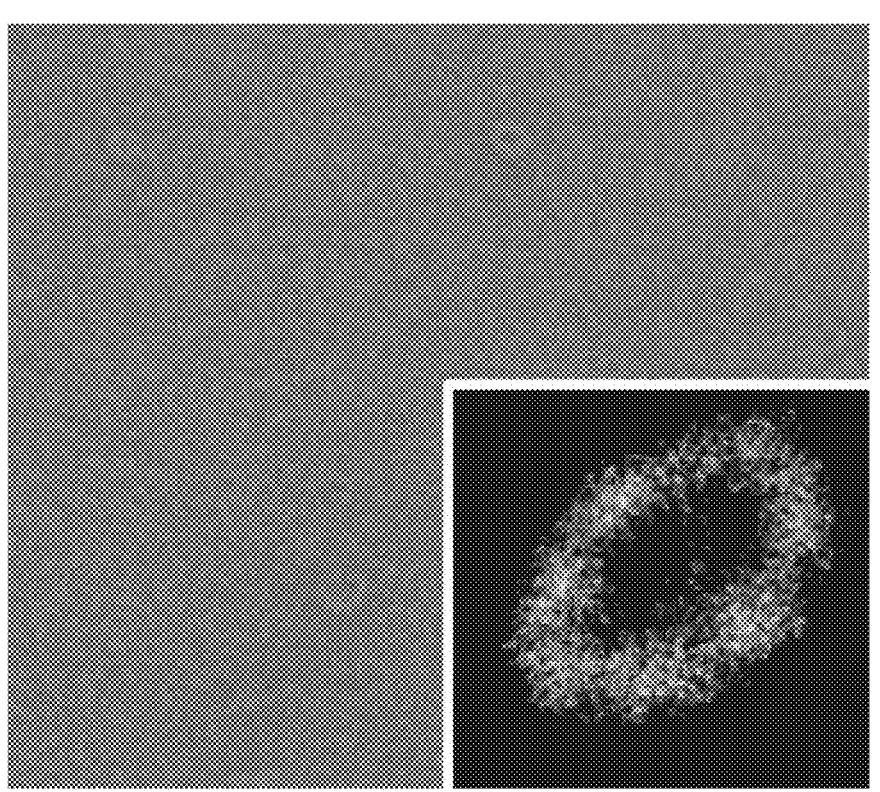
FIG. 3B provides an image showing that IE2 oligomerizes as a ring around a double stranded oligonucleotide (ONT) having the sequence (SEQ ID NO: 1)
GACAGATCGTTTAGTGAACCGTACACGA.
Figure 4A:
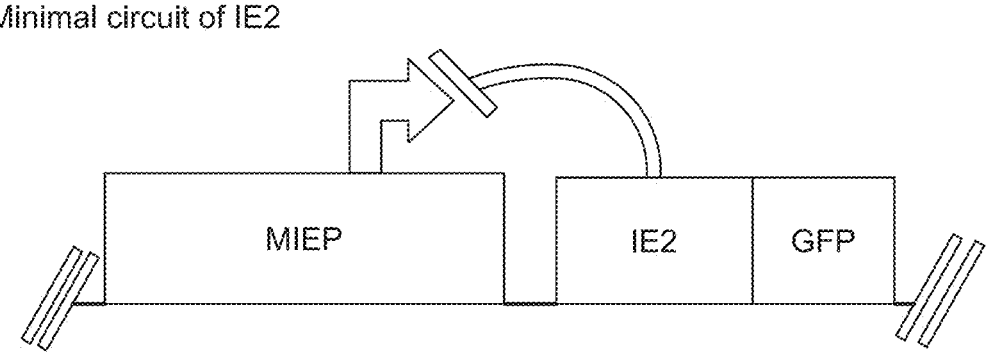
FIG. 4A provides a schematic illustrating a minimal regulatory circuit of IE2.
Figure 4B:
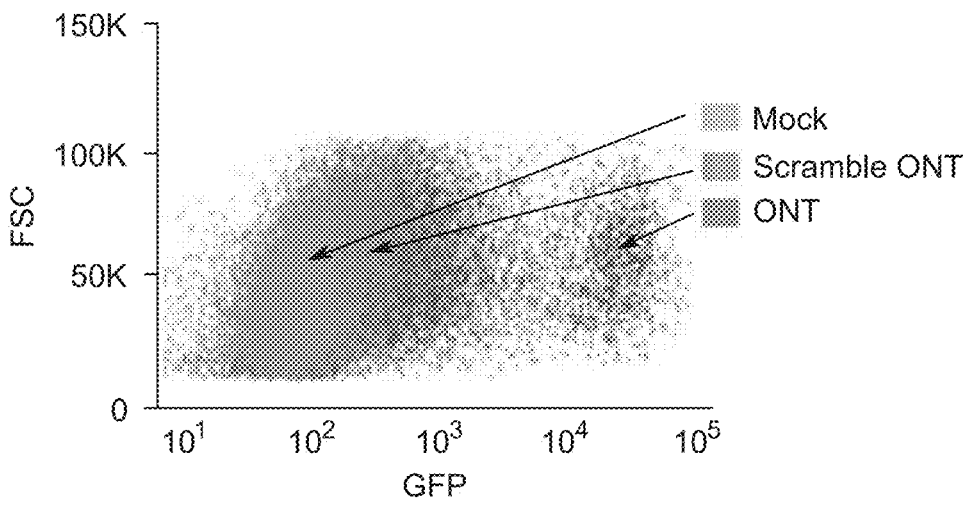
FIG. 4B provides a graph illustrating that a double stranded oligonucleotide (ONT) having the sequence GACAGATCGTTTAGTGAACCGTACACGA (SEQ ID NO: 1) breaks negative feedback in an IE2 minimal circuit.
Figure 4C:
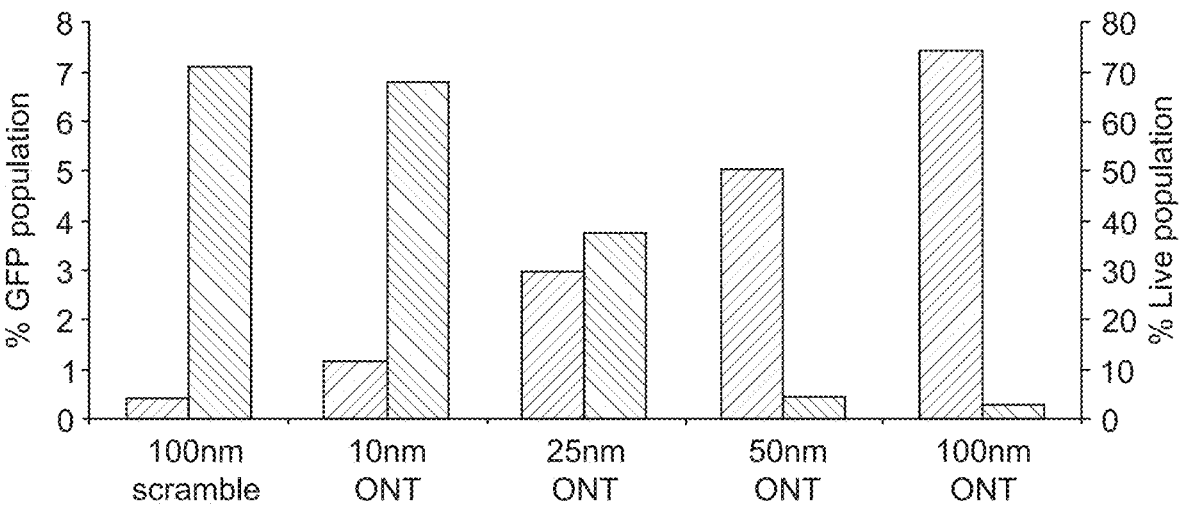
FIG. 4C provides a graph illustrating that a double stranded oligonucleotide (ONT) having the sequence GACAGATCGTTTAGTGAACCGTACACGA (SEQ ID NO: 1) breaks IE2 negative feedback leading to cytotoxicity in a dose dependent manner.
Figure 5:
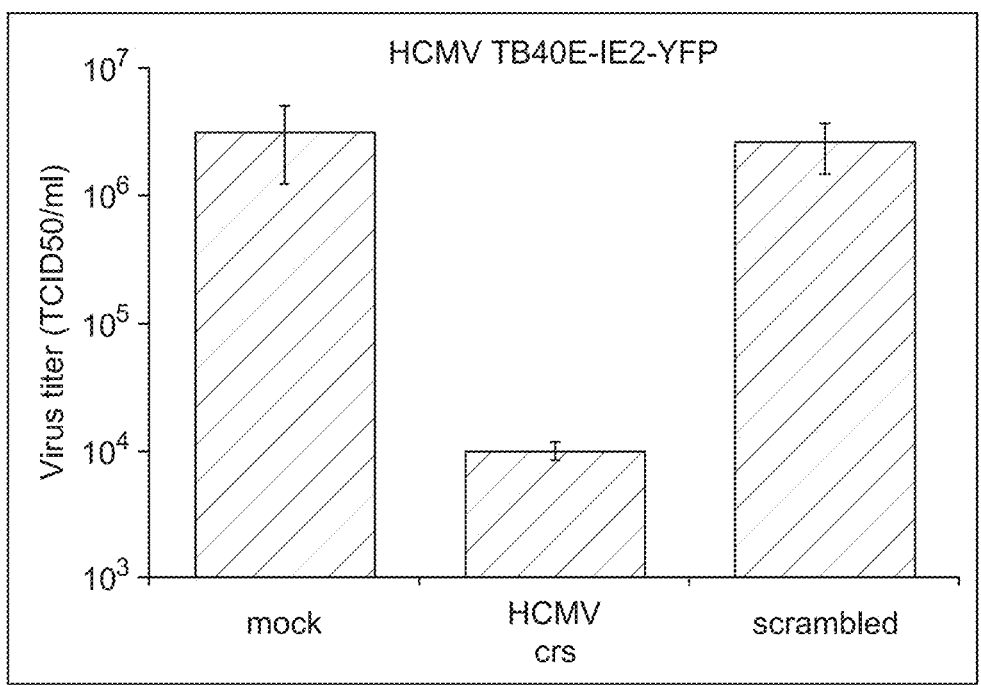
FIG. 5 provides graphs illustrating that transcription regulatory circuit disruptors interfere with Herpesvirus productive infection in cell culture. The ONT including the sequence of the HCMV crs has the sequence
GACAGATCGTTTAGTGAACCGTACACGA (SEQ ID NO: 1). The ONT including the sequence of the Mouse CMV (MCMV) crs has the sequence
GACAGACCAGCGTCGGTACCGTACACGA (SEQ ID NO: 2). The ONT including the sequence of the HSV-1 crs has the sequence (SEQ ID NO: 3)
CCGAGGACGCCCCGATCGTCCACACGGAG.
Figure 5:
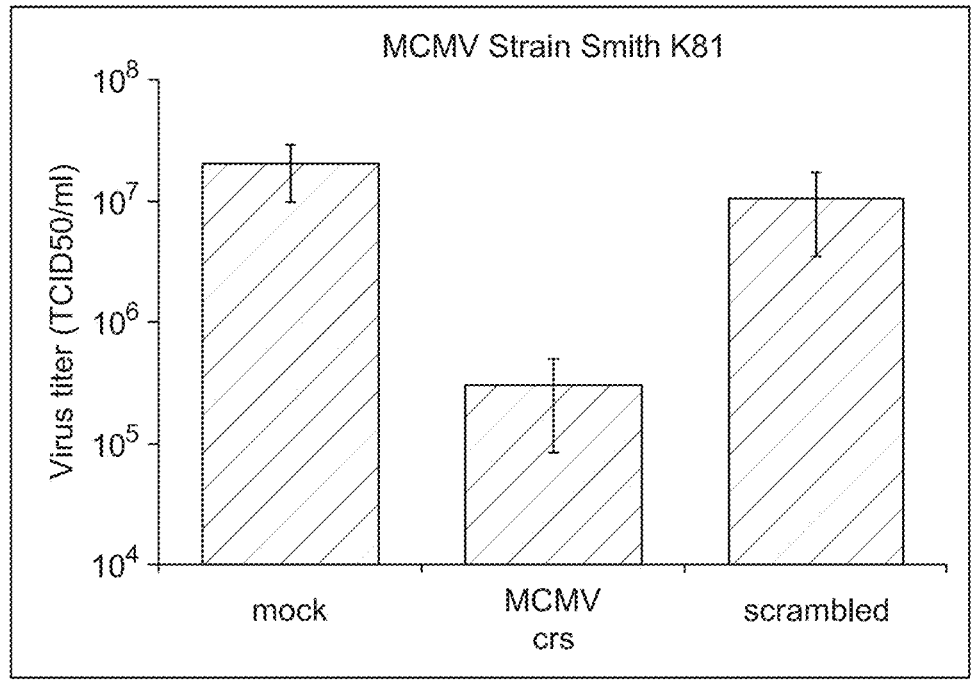
Figure 11A:
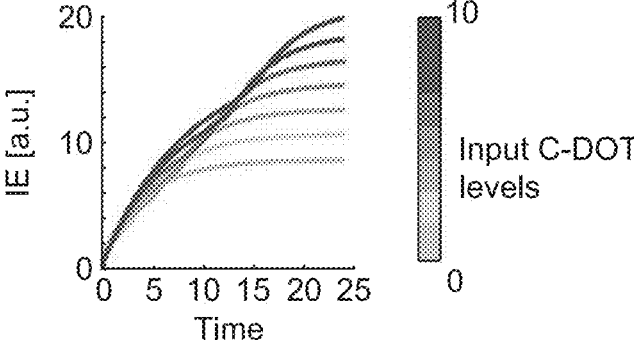

It was hypothesized that oligonucleotides mimicking the palindromic DNA-binding site could titrate IE proteins away from the ers and act as competitive inhibitors to disrupt IE negative feedback (FIG. 2a). Mathematical modeling predicted that such circuit-disrupting oligonucleotide therapies (C-DOTs) may in fact raise IE protein to cytotoxic levels (FIG. 2b and FIG. 11a). Theoretically, to escape C-DOTs and recapitulate a feedback loop, the virus would need to evolve a new IE-protein domain to recognize a new DNA sequence and simultaneously evolve a new cognate DNA binding sequence in the IE promoter; these C-DOT escape mutants would evolve on order of $\mu^2$, which would occur substantially slower than observed for ACV/GCV resistance (FIG. 2c). It is conceivable that single mutants in the IE protein could arise and bind alternate crs-like sequences pre-existing in the promoter region, thereby circumventing the combinatorial mutation hypothesis. However, there are no comparable palindromes within 500 bp of the MIEP promoter and if such sequences were present, then crs-deletion mutants should strongly select for such IE86 mutants that can recapitulate negative feedback, which does not occur over ~ 1 month of culturing[22].

FIG. 2: Theory predicts that antiviral disruption of transcriptional feedback would substantially delay evolution of resistance. (a) Schematics of the herpesvirus IE (IE86 and IE175) transcriptional negative-feedback circuits in the intact wild-type form (upper) and after disruption (lower) by putative circuit-disrupting oligonucleotide therapy (C-DOT). When feedback is intact, IE proteins bind the cis repression DNA sequence in their respective IE promoters (cyan) and downregulate transcriptional activity to prevent IE protein levels from reaching cytotoxic levels. When feedback is disrupted, for example by IE proteins being titrated away by binding free oligonucleotides encoding cis-repression sequences, IE promoter activity is not down-regulated and IE proteins reach cytotoxic levels (~1.5-fold above homeostatic levels)[22]. (b) Numerical solutions of an experimentally validated computational model of IE feed-back[22,24] showing that C-DOTs effectively break feedback to increase IE protein levels into the cytotoxic regime. See also FIG. 11a. (c) Analytical calculation for the 50% emer-gence time of resistance mutants ($T_{resistance}$) as a function of the mutation rate u. The observed emergence of resistance to GCV in the clinic[7] is shown as a point above the measured TK mutation rate ($\mu=10^{-4}$). Putative C-DOT resistance, predicted to require at least two mutations (one in the protein and one in the promoter), is shown as a line corresponding to measured $\mu^{11}$. Inset: representative dynamics of emer-gence for either a GCV mutant (black) or a putative C-DOT mutant (cyan) that requires only viral two mutations. See Methods for equations.

Figure 8A:
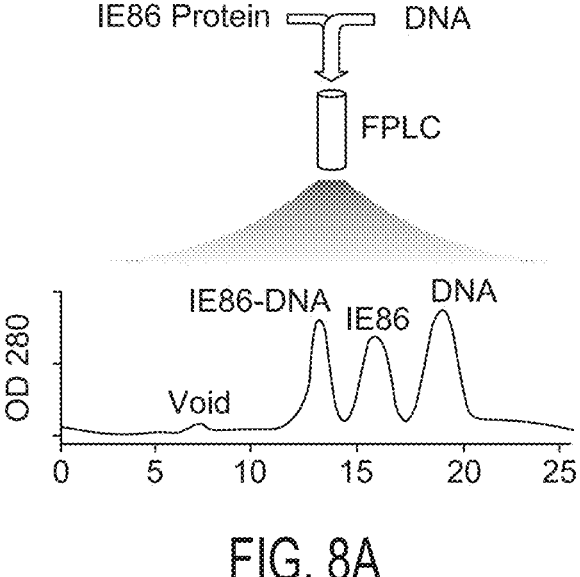
Figure 8B:
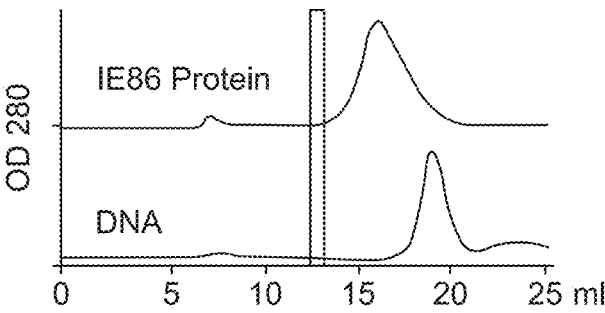
Figure 8C:
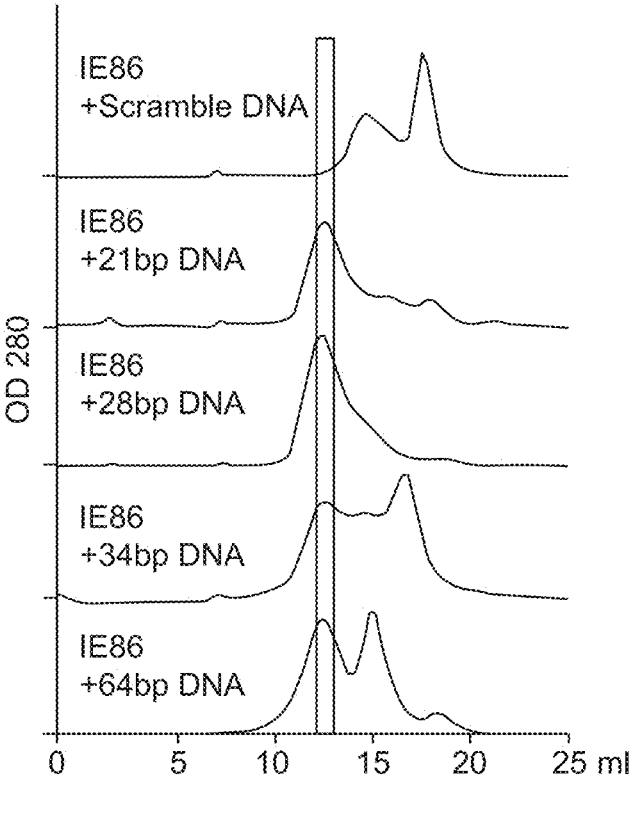
Figure 11B:
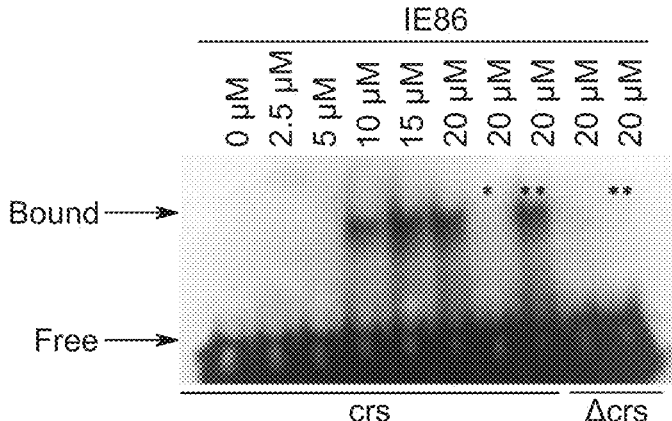
Figure 11C:
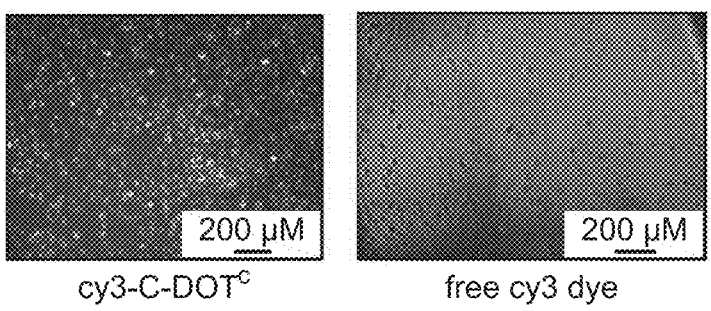

To find oligonucleotides that optimally titrate IE proteins, an in vitro liquid-chromatography assay was developed to quantify the efficiency of various linear DNA oligonucle-otides in catalyzing formation of the IE86 protein-DNA complex (FIG. 8a). To validate the assay, electrophoretic mobility shift assays (EMSA) were used and it was verified that purified IE86 protein bound double-stranded DNA oligonucleotides in a sequence-specific manner (FIG. 11b). An array of crs-encoding oligonucleotides of various lengths was tested and it was found that a linear 28 base-pair (bp) DNA most efficiently catalyzed formation of the IE86-DNA complex (FIG. 8b-c). Shorter or longer crs-encoding DNAs were less efficient at titrating IE86 and promoting protein-DNA complex formation.

Figure 8D:
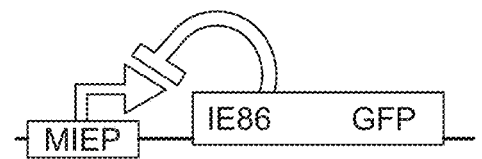
Figure 8D:
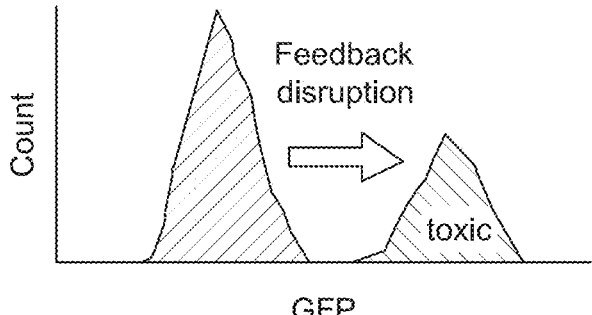
Figure 8D:
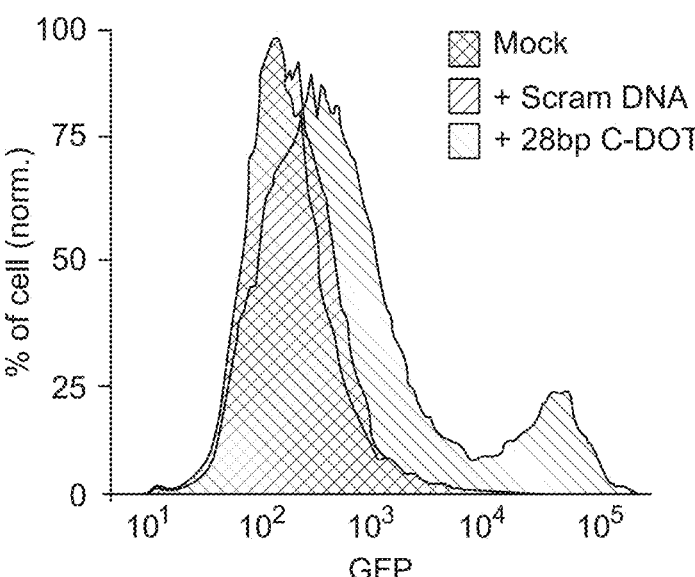
Figure 8E:
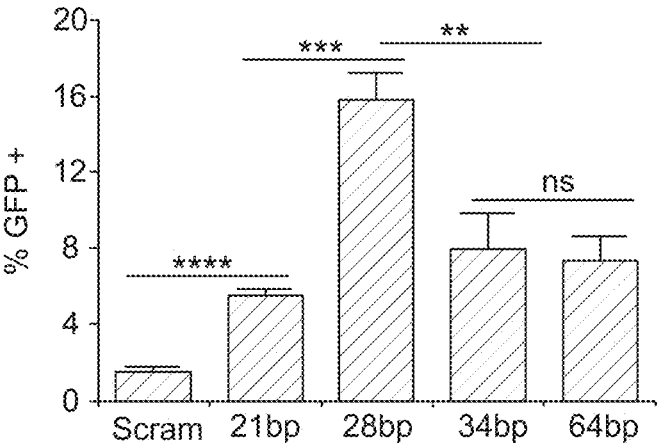
Figure 8F:
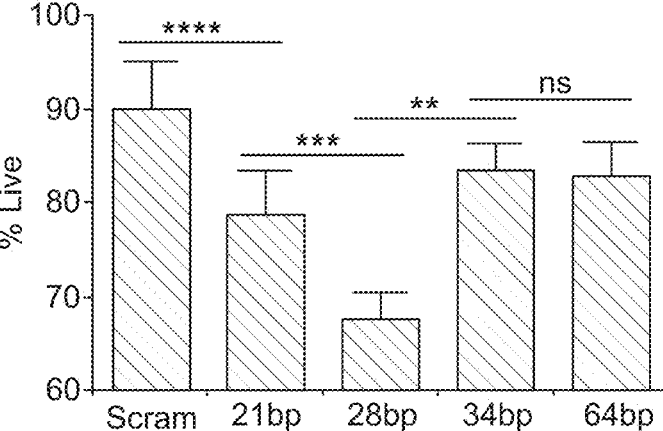
Figure 11D:
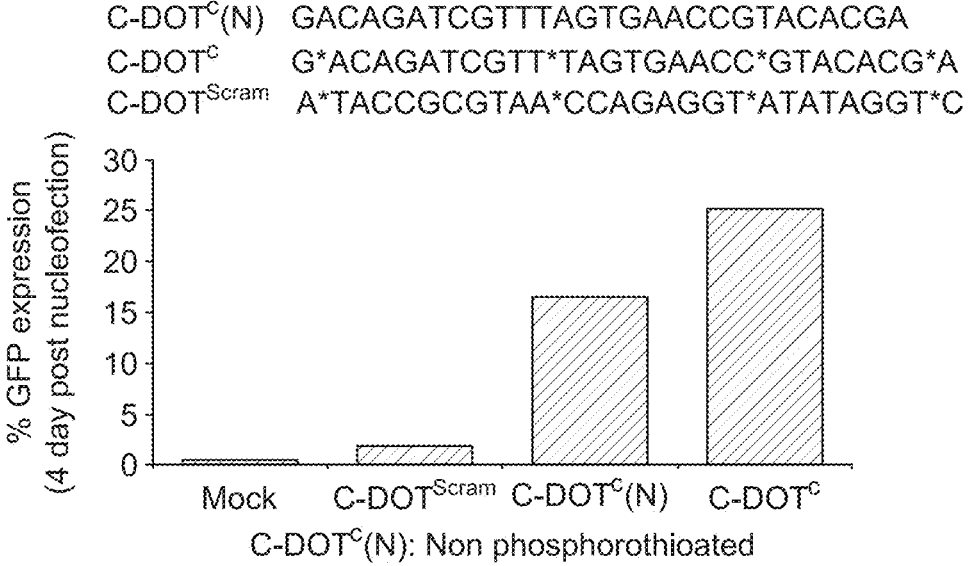

To test if these DNAs disrupted negative feedback, a retinal pigment epithelial cell line stably transduced with a previously described minimal IE86 negative-feedback reporter circuit[22] was used. These cells express the IE86 and GFP under the control of the IE86 promoter-enhancer such that increases in GFP indicate disruption of negative-feed-back leading to cell death 48-72 hours later (FIG. 8d). Cells were nucleofected with the putative C-DOTs, or sequence-scrambled control oligonucleotides, and GFP expression assayed by flow cytometry at 48 h (FIG. 8d). DNA uptake by cells was verified by cy3 fluorescence (FIG. 11c) and to enhance oligonucleotide stability, DNAs were modified by internal phosphorothioate bonds (FIG. 11d). In agreement with the biochemical assays, the 28 bp DNA most efficiently increased the GFP+ population (FIG. 8e) and correspond-ingly decreased live-cell percentages (FIG. 8f). Feedback-circuit disruption was dose dependent (FIG. 12a-b) and was enhanced by concatemerization as well as using nanopar-ticles to enhance cell uptake (FIG. 13a-c). Collectively, these results indicated that relatively short (<30 bp) double-stranded DNAs might be viable circuit disruptor oligonucle-otides.

FIG. 8: Biochemical and in vitro analyses identify oligo-nucleotides that disrupt transcriptional feedback circuitry. (a) Schematic of the IE86-protein binding assay: the C-ter-minus of the IE86 protein was expressed in E. coli, concen-trated and incubated with 14-64 bp DNA oligonucleotides for 30 minutes at room temperature, then passed through an FPLC column. Protein-DNA complex formation was quan-tified by optical density (OD 280 nm) of FPLC fractions; the IE86 protein (obligate dimer) fragment elutes in the 15 mL fraction, free dsDNA oligonucleotides elute in the 18 mL fraction, and the multimeric protein-DNA complex elutes in the 13 mL fraction. (b) FPLC chromatography profiles of IE86 protein fragment input and dsDNA input prior to co-incubation. (c) Chromatographs of IE86 fragment incu-bated with either a sequence-scrambled control dsDNA oligonucleotides or crs-containing dsDNA oligonucleotides of differential lengths. The 28 bp crs DNA oligonucleotide most efficiently titrates free protein from the 15 ml fraction into the 13 mL fraction (~98% of protein is found in the 13 mL protein-DNA complex fraction when the 28 bp ers DNA oligonucleotide is added). (d) Left: Schematic of the mini-mal IE negative-feedback circuit (MIEP-IE86-IRES-GFP) encoded within the feedback-reporter cell line. Disruption of negative feedback generates increases in GFP fluorescence. Right: Flow cytometry of feedback reporter cells 48 h after nucleofection with either a 28 bp crs-containing DNA oligonucleotide, a scrambled DNA oligonucleotide (nega-tive control), or mock nucleofection (no DNA oligonucle-otide) showing that ers-encoding DNA oligonucleotides disrupt feedback and act as a putative C-DOTs. (e, f) The 28 bp crs-containing DNA oligonucleotide optimally disrupts feedback and induces cytotoxicity in the feedback-reporter cell line. DNA oligonucleotides (from the FPLC analysis in panel c above) were nucleofected into the reporter cell line and analyzed by flow cytometry after 48 h to determine IE86 expression (GFP; panel e), and cytotoxicity (panel f). (p-value less than 0.05 was considered statistically signifi-cant: *<0.05, <0.01, *<0.001, ****<0.0001).

FIG. 11: Simulations and in-vitro analyses indicate that excess ers DNA oligos competitively bind IE86 and would break negative feedback to increase IE86 levels. (a) Numeri-cal solutions of an experimentally validated Ordinary Dif-ferential Equation (ODE) model of the Major Immediate Early circuit of CMV[22, 24] modified to include C-DOTs as described in Methods. All parameters are kept the constant and initial levels of oligos at t=0 are varied as indicated. (b) Electrophoresis mobility shift assays (EMSA) verify that the C-terminus of IE86 sequence specifically interacts with ers-containing DNA. Digoxygenin (DIG)-labeled DNA oligo probes of the crs and Δcrs sequences, as described[36], were used for binding and detection. EMSA was performed after incubating DIG-labeled DNA probes with increasing concentrations of IE86 protein (0 μM to 20 μM) for 30 minutes at room temperature (lanes 1-6). To determine if the IE86-crs interaction was sequence specific, either 20-fold excess of unlabeled crs (*) was added (lane 7) or 20-fold unlabeled Δcrs (**) was added (lanes 7-10). (c) Delivery and stability of C-DOTs in the IE86 minimal-circuit cell line. Fluorescence micrographs of ARPE-19 cells four days post nucleofection with cy3-labeled 28 bp DNA oligomer cy3-C-DOT$^C$ (left) or free cy3 dye (right). (d) Top: Sequence schematics of the unmodified 28 bp C-DOT$^C$ (N), the phosphorothioated 28 bp C-DOT$^C$ (* indicates phosphoro-thioated bases), and 28 bp scrambled DNA (also referred to as C-DOT$^{Scram}$), which also contains phosphorothioated bases. Bottom: Flow cytometry of ARPE-19 IE86 minimal circuit cell line four days after nucleofection with the various DNA C-DOTs.

FIG. 13: C-DOT nanoparticles enhance cell delivery and C-DOT concatemers enhance IE86 sequestration and feed-back disruption. (a) Cells take up C-DOT$^C$-SNA nanopar-ticles more efficiently than 'free' C-DOT$^C$. Cy3-tagged C-DOT$^C$ DNA oligos were conjugated to 10-nm gold nan-oparticles to generate 'spherical nucleic acid' (SNA) nan-oparticles. Cells were then incubated in culture with the C-DOTs SNA nanoparticles. 4 days later, cells were assayed for cy3 uptake by microscopy. Micrographs of ARPE-19 cells 4 days after incubation with cy3-tagged C-DOT$^C$-SNA, cy3-tagged 'free' C-DOT$^C$, or unlabeled 15-nm gold nan-oparticles lacking cy3 (as a control) are shown in the cy3 fluorescence channel (left) and the bright field channel (right). (b) FPLC of purified C terminus IE86 protein (N-terminus tagged with maltose binding protein and fractionated for the dimeric form, as in FIG. 2a) then incubated with a C-DOT$^H$ containing one crs sequence (C-DOT 1×) of two concatenated crs sequences (C-DOT 2λ-concat) for 30 minutes at room temperature (see Extended Data Table 1 for C-DOT sequences). Oligomerized fraction (% absorbance at ~13 ml fraction at OD280) was compared for both the samples. (c) Flow cytometry analysis of the IE86 minimal-circuit reporter cell line (ARPE-19 cells) two days after nucleofection with C-DOT (1×), C-DOT (2×)-concat, or the scrambled DNA oligo (C-DOT$^{Scram}$, negative control).

Figure 7A:
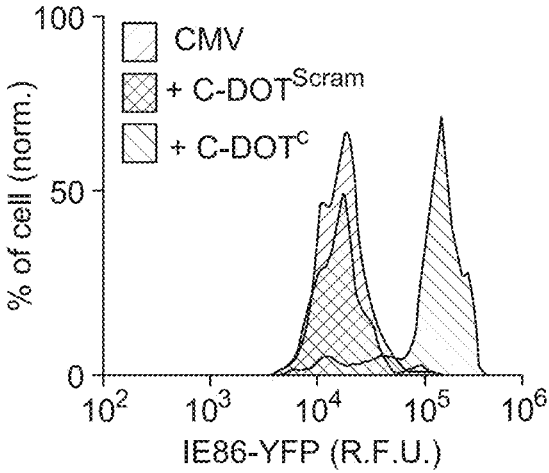
Figure 7B:
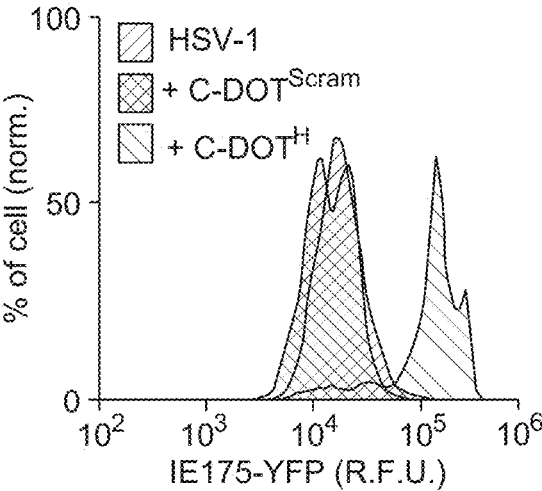

Next, the effects of disrupting transcriptional feedback in the context of viral infection were investigated. The 28 bp DNA for CMV IE86 was designated as C-DOT$^C$ (C-DOT for CMV) and it was found that C-DOT$^C$ efficiently disrupted IE86 negative feedback in cells infected with a clinically-derived isolate of CMV[24] (FIG. 7a). It was next hypothesized that replacing the 14 bp crs within C-DOT$^H$ with the 15 bp repression sequence from IE175's promoter could generate a C-DOT for HSV-1 (now termed C-DOT$^H$). As predicted, C-DOT$^H$ disrupted IE175 negative feedback in cells infected with clinically-derived HSV-125 (FIG. 7b). There was minimal difference in % IE positive cells, indicating that C-DOTs did not alter permissiveness of cells to viral infection (FIG. 12c). Strikingly, the C-DOTs also reduced single-round viral replication titers for both CMV and HSV-1 at multiplicity of infection (MOI) of 0.1 by ~100 fold (FIG. 7c-d), in agreement with genetic disruption of IE negative feedback[22]. To be sure that the observed antiviral effects were not specific to the virus strain or cell type used, the following were also tested (i) CMV strain AD169 and (ii) various GCV-resistant CMV strains in human foreskin fibroblasts, as well as (iii) murine CMV and (iv) rhesus CMV, in mouse and primate cells respectively, and in all cases found similar 100-fold titer reduction using the corresponding C-DOTs (FIG. 14a-c).

FIG. 12: C-DOTs break IE negative feedback in a dose-dependent manner and do not alter cell permissiveness to viral infection. (a) Flow cytometry dot plots of the IE86 minimal circuit reporter cell line after nucleofection with increasing doses of the 28 bp C-DOT$^C$ and 100 μM of the 28 bp C-DOT$^{Scram}$ (negative control). % GFP+ population was quantified two days post nucleofection (SSC=side scatter). (b) Top: Quantitative (LICOR™) Western blot analysis of IE86 from cell lysates of panel A at two days post C-DOT nucleofection; Bottom: IE86 loading control. (c) Flow cytometry dot plots of naïve or C-DOT-nucleofected ARPE-19 cells after infection with CMV strain TB40/E-IE86-YFP or HSV-1 strain 17syn+IE175-YFP. Cells were infected 12 h after nucleofection with the indicated C-DOT and analyzed at one-day post infection.

FIG. 14: C-DOTs can be engineered to interfere with a broad range of species-specific herpesviruses including drug-resistant strains. (a) Sequence homology for the crs of human CMV, rhesus CMV (RhCMV), and murine CMV (MCMV). Sequence homology and divergence are represented. (b)C-DOT$^{MCMV}$ interferes with MCMV replication. NIH 3T3 mouse fibroblast cells were nucleofected with either 28 bp C-DOT$^{MCMV}$, or C-DOT$^{Scram}$, or mock nucleofected 24 hours prior to MCMV infection at MOI=0.1. 4 days post infection, virus titers were assayed by TCID50. (c)C-DOT$^{RhCMV}$ downregulates RhCMV replication. (Upper) Fluorescent micrographs, 4-day post nucleofection, of Telo-RF cells nucleofected with either a 28 bp C-DO-T$^{RhCMV}$, or a C-DOT$^{Scram}$, or mock nucleofected and then infected with RhCMV (RhCMV 68.1 GFP) at MOI=0.1. (Lower) Virus titers assayed by TCID-50 at 4 days post infection. (d)C-DOT$^C$ interferes with replication of ganciclovir-resistant (GCV$^R$) and foscarnet-resistant (FOS$^R$) CMV strains. MRC-5 cells were nucleofected with C-DOT$^C$ or C-DOT$^{Scram}$ then infected 24-hour later with either the parent CMV AD169 (control) or GCV$^R$ or FOS$^R$ strains (CMV GDGrK17, CMV GDGrP53, CMV 759rD100-1, CMV PFArD100). Virus titers were assayed by TCID-50 at 4 days post infection.

Figure 7C:
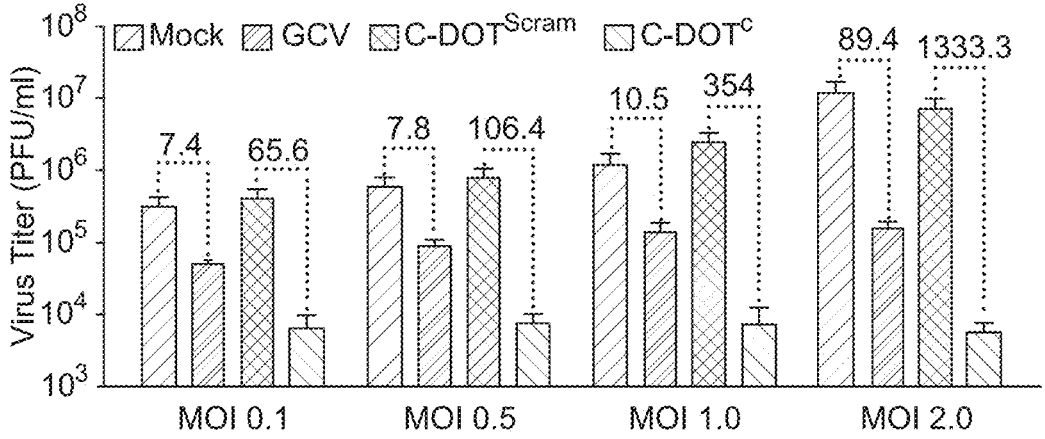
Figure 7D:
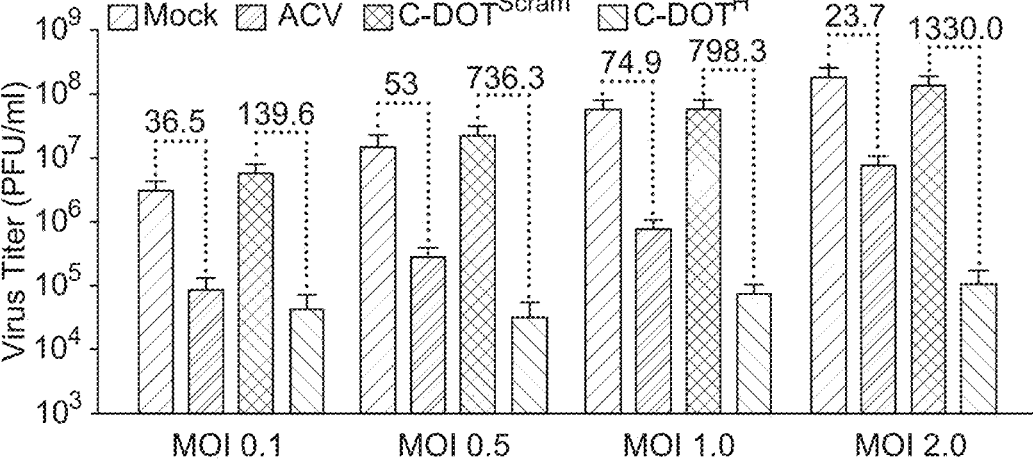

In stark contrast to ACV and GCV, C-DOT increases virus fold reduction at higher MOI, and, at MOI=2, C-DOTs exhibited a >1300× reduction whereas ACV/GCV elicited 35-70× reduction in viral replication (FIG. 7c-d). Such robustness to high-viremic conditions has not been previously described for an antiviral[26], but is consistent with the putative C-DOT mechanism of action through feedback disruption and IE-mediated cytotoxicity—higher MOIs deliver more genomes, which generates more potentially cytotoxic IE protein.

Figure 15A:
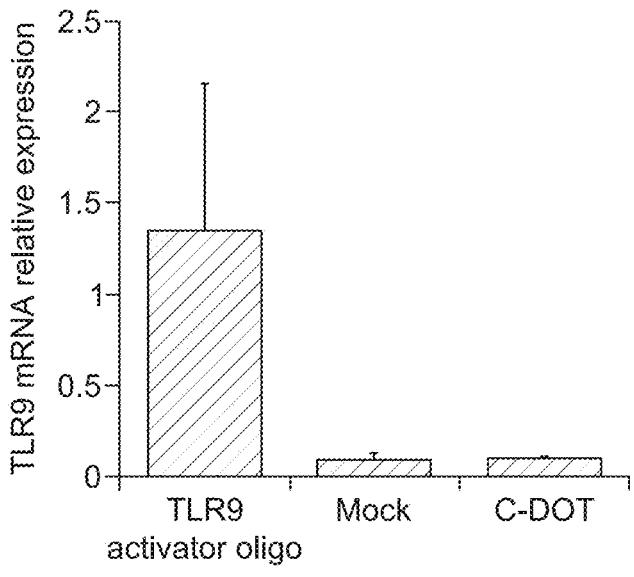
Figure 15B:
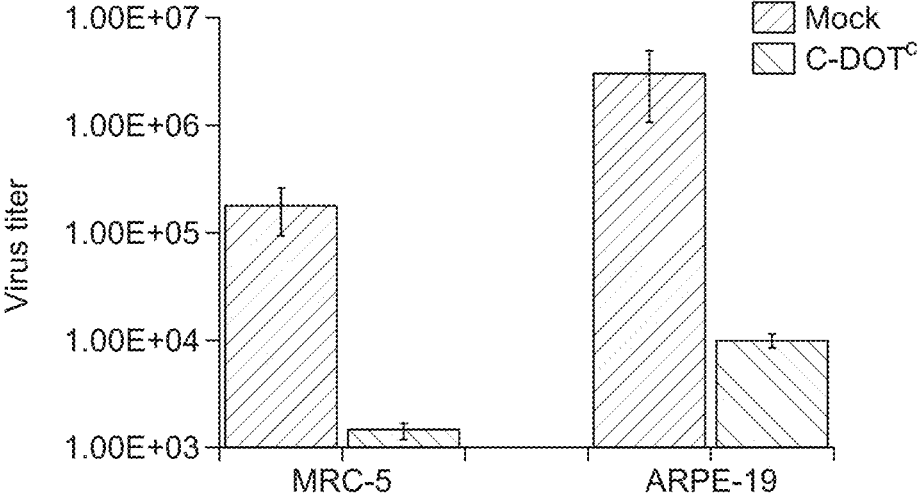

Importantly, sequence-scrambled oligonucleotides (C-DOT$^{Scram}$) did not exhibit antiviral effects suggesting that C-DOTs are not acting via innate-immune mechanisms (e.g., activation of cGAS-STING pathway via TLR9), which is consistent with efficient cGAS pathway activation requiring DNAs of >300bp27, whereas C-DOTs are <30 bp. However, to verify that C-DOT activity is independent of cGAS-STING, C-DOTs were tested under conditions of high and low cGAS-STING expression and observed little difference in C-DOT antiviral effects and no effects for C-DOT$^{Scram}$ in either setting (FIG. 15b). Moreover, C-DOTs did not activate TLR9 expression (FIG. 15a).

Figure 7E:
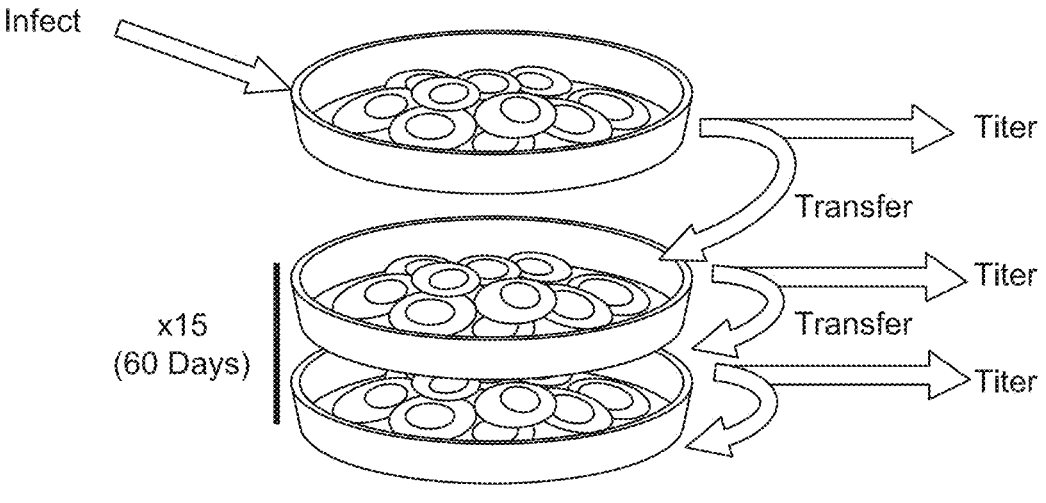
Figure 15C:
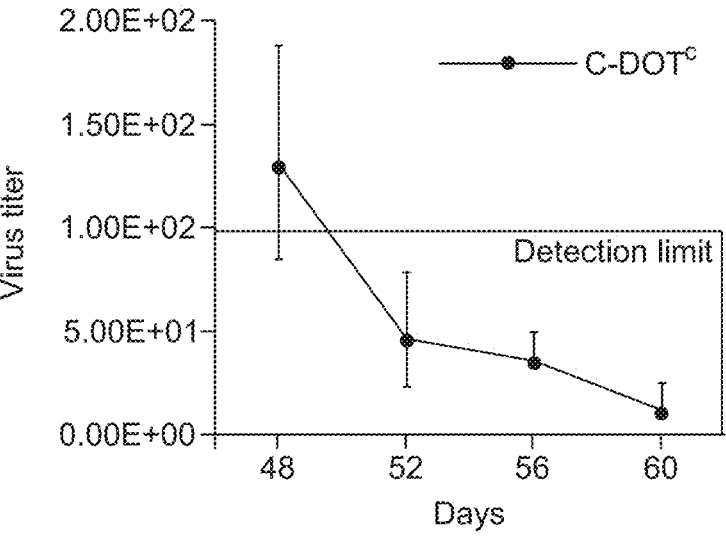
Figure 15D:
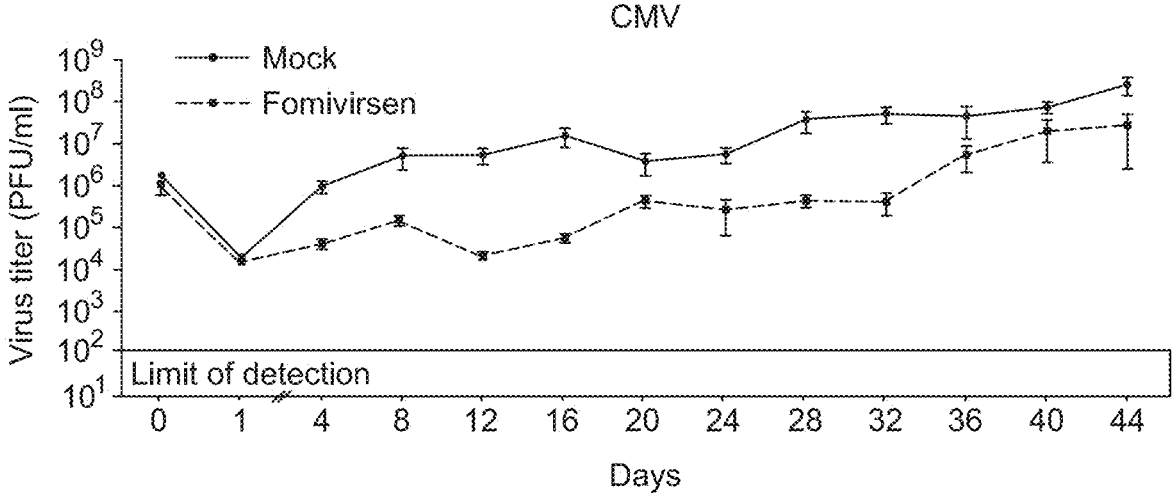
Figure 15E:
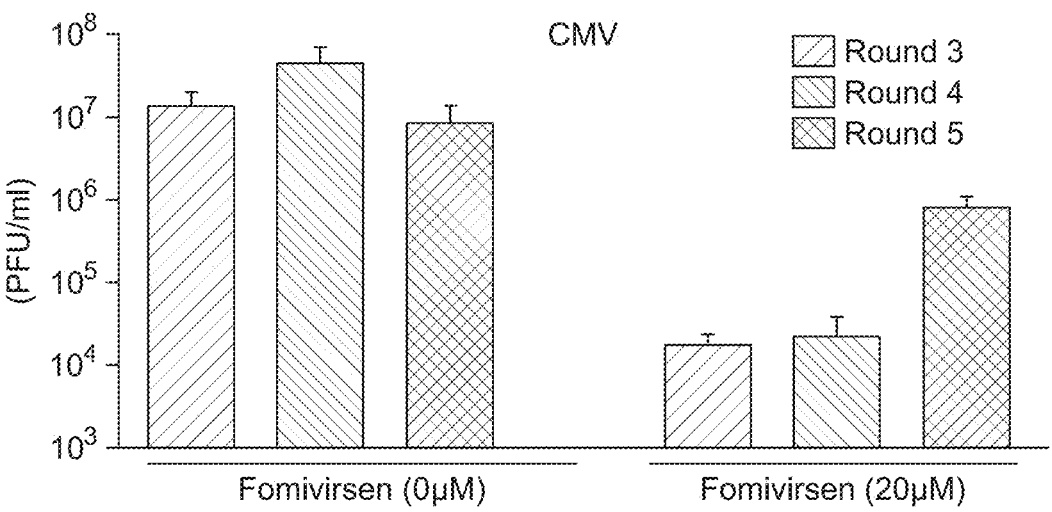
Figure 15F:
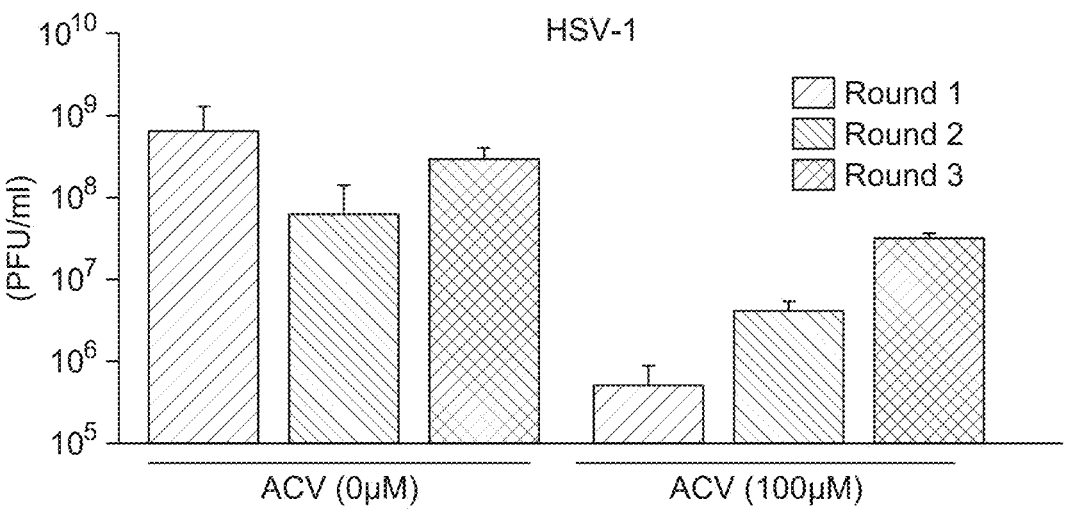

To examine the rate of emergence of viral escape mutants, the next step involved using a continuous-culture approach where virus was consecutively passaged from infected cells to fresh uninfected cells every 4 days (a typical CMV replication round) until virus was undetectable in presence of C-DOT treatment (~40-60 days; FIG. 7e). C-DOT$^C$ was compared to Fomivirsen[28], the first approved DNA oligonucleotide therapy (an antisense DNA for IE86); C-DOT$^H$ was compared with ACV. As previously reported[12], it was found that HSV-1 resistance to ACV emerges within two rounds of infection (FIG. 15f) and that CMV resistance to Fomivirsen[28] arises within 3-4 rounds of infection (FIG. 15d-e).

Figure 7F:
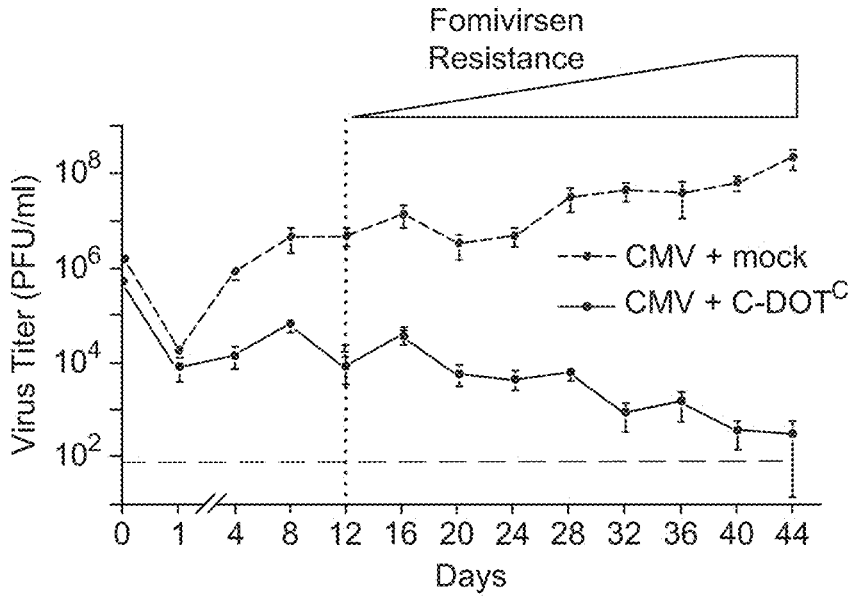
Figure 7G:
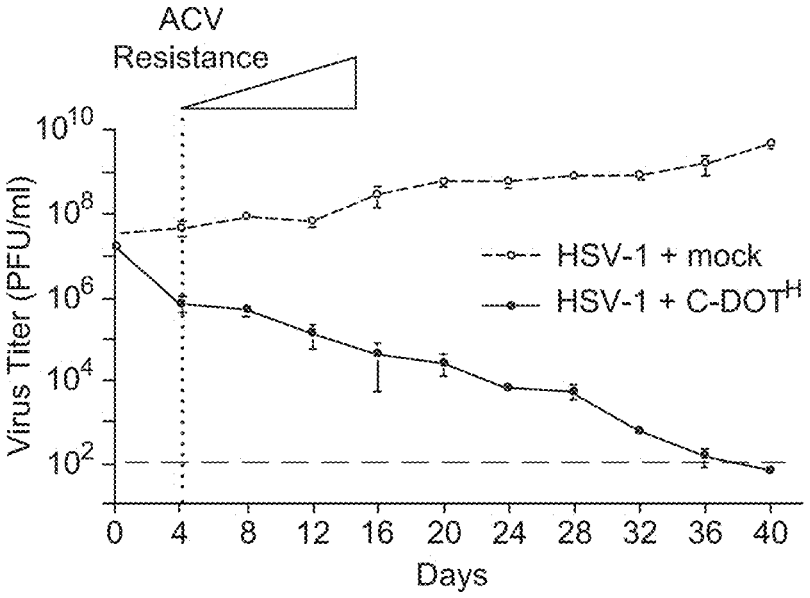

In striking contrast, C-DOT$^C$ steadily reduced CMV titers to below the limit of detection by day 52, with no evidence of CMV resistance to the C-DOT$^C$ (FIG. 7f). Subsequent sub-culturing showed that the virus was cleared (FIG. 15c). Similarly, C-DOT$^H$ steadily reduced HSV-1 titers to below detection by day 40, with no evidence of resistance (FIG. 7g). In agreement with this, sequence analysis indicated that no virus mutations arose in the 500 bp-region surrounding the promoter repression sequences and only single-nucleotide transient polymorphisms in the IE-protein regions responsible for DNA binding. Overall, these results indicate that disrupting feedback may be an escape-resistant antiviral strategy.

FIG. 7: Feedback circuit disruption interferes with viral replication even at high MOI and limits the evolution of resistance. (a) Flow cytometry of ARPE-19 cells nucleofected with the 28 bp dsDNA that titrates IE86 (C-DOT$^C$) or scrambled dsDNA sequence (C-DOT$^{Scram}$) and infected with a clinically derived CMV (TB40E) encoding an IE86-YFP (MOI=0.1) then analyzed at 2 days post infection (dpi). (b) Flow cytometry of ARPE-19 cells nucleofected with a 29 bp DNA to titrate IE175 (C-DOT$^H$) or scrambled dsDNA sequence (C-DOT$^{Scram}$) and infected with HSV-1 (17syn+ strain) encoding an IE175-YFP (MOI=0.1) then analyzed at 2 dpi. (c) Single-round viral titering of CMV in the presence of 100 μM GCV, PBS, or 25 μM C-DOT$^C$ (or C-DOT$^{Scram}$) at 4-days post infection under different initial MOIs. (d) Single-round viral titering of HSV-1 in presence of 100 μM ACV or 25 μM C-DOT$^H$ (or C-DOT$^{Scram}$) at 4-days post infection under different HSV-1 MOIS. (e) Schematic of the continuous-culture experiment; ARPE-19 cells (+/−C-DOT) were infected with CMV or HSV-1 (0.1 MOI) and at 4-day post infection, supernatant was collected and was used to infect naïve ARPE-19 cells +/−C-DOT until day 60. (f) Continuous culture titers for CMV (TB40E-IE86-YFP) in the presence of C-DOT$^C$ (red) or mock treatment (black). Fomivirsen resistance (positive slope of the titering dynamics) was observed beginning at day 12 (FIG. 15$d$,$e$). (g) Continuous culture for HSV-1 (17syn+IE175-YFP virus) in the presence of C-DOT$^H$ (red) or mock treatment (black). ACV resistance (positive slope of the titering dynamics) observed beginning at day 4 (FIG. 15$f$).

FIG. 15; C-DOTs do not activate innate immune responses in cell lines and—unlike fomivirsen and acyclovir—do not select for resistant viral mutants. (a)C-DOTs do not activate the TLR9 response. qPCR analysis of TLR9 expression in ARPE-19 cells 4 days after nucleofection of either mock nucleofection, nucleofection with a TLR9-activating oligonucleotide (ODN2216)[44], or nucleofection with C-DOT$^C$. Total RNA was extracted from cells and corresponding cDNA was quantified by qPCR using sequence specific primers for TLR9 (see Extended Data Table 1 for sequences). (b)C-DOTs do not act through the cGAS-STING pathway. ARPE-19 (low cGAS-STING activity) and MRC-5 cells (high cGAS-STING activity) were nucleofected with C-DOTE or mock and infected with TB40E-IE86-YFP or AD169, respectively. Virus titers were assayed by TCID-50 at 4 days post infection. (c)C-DOT$^C$ decreases CMV titers below detection by day 60 in the continuous culture setting. CMV titers from the continuous culture experiment followed out to day 60. ARPE-19 cells (+/−25 μM C-DOT) were infected with CMV (TB40E-IE86-YFP; MOI=0.1). (d) CMV and HSV-1 rapidly acquire resistance to approved antivirals (fomivirsen and acyclovir). Viral titers from the continuous culture experiment in the presence or absence of fomivirsen. Mock- or fomivirsen-nucleofected ARPE-19 cells were infected with CMV (TB40E-IE86-YFP; MOI=0.1); at 4 days post infection, supernatants were transferred to infect new naïve ARPE-19 cells (+/−fomivirsen) and transfers repeated every 4 days until day 44. (e) Viral titers from the continuous culture experiment (rounds 3 to 5), +/−25 μM fomivirsen. A positive slope in the titers+fomivirsen (i.e., emergence of resistance) is observed beginning at round 3 of infection. (f) HSV-1 resistance to acyclovir (ACV). Viral titers of ARPE-19 cells infected with HSV-1 (17syn+IE175-YFP; MOI=1)+/−100M ACV and supernatant transferred every 2 days over 3 consecutive rounds of infection. Virus titers were assayed by TCID50 every 2 days post transfer; positive slope in the titers (i.e., resistance) is evident despite 100 μM ACV.

Finally, it was tested if transcriptional feedback could be disrupted in vivo using the established model of herpes infection in mice[29]. Briefly, in this model, mice are infected with HSV-1 in the cornea, and interventions are topically applied at the site of infection to test efficacy. Using standard practice, mice were infected with HSV-1 IE175-YFP, then 6 hours later (to avoid interfering with virus uptake), oligonucleotides were applied and after two days, corneas were harvested for imaging and quantification of viral replication by q-PCR and titering (FIG. 6$a$). C-DOT uptake by cells was quantified by Cy3 fluorescence (FIG. 16$a$) and as predicted, C-DOT treatment first caused an increase in IE175 (FIG. 16$b$) followed by a significant reduction in the percentage of HSV-1 infected cells (FIG. 6$b$-$c$). In agreement with these data, C-DOT$^H$ treatment reduced viral titer by 150-fold (FIG. 6$d$) and significantly reduced viral genome replication (FIG. 6$e$). Together, these results demonstrate that feedback disruption reduces viral replication in vivo.

FIG. 6A: Feedback disruption inhibits viral replication in an in vivo model. (a) Schematic of the HSV-1 corneal infection model in mice. BL-6 mice, 6-10 weeks old, undergo corneal debridement followed by infection with HSV-1 17syn+IE175-YFP virus (1×10$^5$ PFU). 6 hours post infection, 25 μM C-DOT$^H$, or C-DOT$^{Scram}$, or PBS, was topically applied to the cornea. Corneas were harvested at 2 days post infection, imaged for YFP, HSV-1 levels quantified by virus titering, and viral genomes quantified by qPCR. (b) Representative YFP-fluorescence images of corneas after harvesting (nuclei stained with DAPI). (c) Quantification of HSV-1 YFP expressing cells in corneas, as determined from the YFP: DAPI ratio. S corneas imaged per sample. (d) HSV-1 viral titers from HSV-1 infected corneas 2 days after treatment with either 25 μM PBS, C-DOT$^{Scram}$ or C-DOT$^H$. Corneas were dissociated using collagenase, subjected to three freeze-thaw and supernatant was used to titer virus using end time dilution method (TCID50). Each data point represents a pooling of corneas from three mice (i.e., 9 corneas per treatment). (e) HSV-1 viral genomic DNA quantification by qPCR 2 days after treatment. Each data point represents a pooling of corneas from three mice (i.e., 9 corneas per treatment). p-values less than 0.05 were considered statistically significant: *<0.05, <0.01, *<0.001.

FIG. 16: C-DOTs can diffuse into naïve mouse corneal cells and increase IE175 expression in mouse corneas following HSV-1 infection. (a) Fluorescence micrographs of dissected mouse comeas incubated with 25 μM cy3-tagged C-DOT$^H$ for 1 hour. Corneas were washed three times in PBS and immediately imaged. (b) YFP and DAPI fluorescence micrographs of dissected mouse corneas +/−C-DOT$^H$ at one day post HSV-1 infection (17syn+IE175-YFP).

Overall, these results indicate that transcriptional feedback could represent a new antiviral target with the potential to substantially delay the emergence of resistance (FIG. 7) and overcome significant treatment barriers including the reduction-in-efficacy at high-viremic loads[26]. In general, oligonucleotide therapies offer specificity with the potential for fewer off target effects over small molecules. While delivery of oligonucleotides remains a major challenge, significant clinical advances have been made with the recent FDA approval of antisense and exon-skipping oligonucleotide therapies delivered via nanoparticles[30-32]. Therefore, C-DOTs using nanoparticle carriers, in the absence of transfection, were also tested and similar antiviral effects were found (FIG. 17$a$-$b$). One could envision nanoparticles harboring combinatorial C-DOTs to treat infections of unknown etiology—a significant problem for ocular infections[33,34] —and the data indicate that such combinatorial 'multiplexed' C-DOTs may be feasible (FIG. 17$c$-$d$).

FIG. 17: Nanoparticle C-DOTs efficiently break transcriptional negative feedback and interfere with virus replication and C-DOTs efficiently inhibit virus replication in a mixed infection setting. (a) Flow cytometry analysis of IE86-GFP minimal circuit cell line treated with 10-nm gold nanoparticles (control) or 10-nm C-DOT$^C$. SNAs at 4 days post incubation. (b) ARPE-19 cells were treated with gold nanoparticles or C-DOT$^C$ SNA, subsequently infected with CMV followed by viral titer at 4 days post infection (by TCID50) (see Extended Data Table 1 for sequences). (c-d) C-DOTs downregulate CMV and HSV-1 infection in a mixed infection setting. (c) Schematic of the mixed infection experiment: ARPE-19 cells nucleofected with equimolar amounts of C-DOTS and C-DOT$^H$ or C-DOT$^{Scram}$ were co-infected with CMV (TB40/E-IE86-YFP) and HSV-1 (17syn+IE175-YFP) at MOI=0.1. (d) qPCR analysis of CMV and HSV-1 viral genomes in the infected cells at four days post infection using primers specific for CMV and HSV-1 (see Table 1 for sequences).

From the perspective of resistance, disrupting autoregulatory circuits yields several theoretical advantages and the calculations represent a lower limit for the time to escape from feedback disruptors. Regulatory loci typically have lower genetic variability than enzymes or receptors 10,35 so mutants in the promoter region and reading frame will arise relatively slowly. Second, >2 mutations will likely be required for generating new DNA-recognition domains in proteins; for herpesviruses even assuming that the regulatory region mutates with average viral frequencyl[0,35] (it is in fact lower) translates to the escape rate scaling as $\sim 10^{-4n}$ (where n>2). Furthermore, putative escape mutants, if they are generated, would have a relative fitness roughly equivalent to wild type, so their selection coefficient and pre-existing abundance will be low. As such, it is predicted that feedback circuit disruption may be an attractive target in other viruses, microbes, and in neoplastic cells with aberrant auto-regulatory circuits.

Material and Methods

Mathematical Modeling and Numerical Simulations

An experimentally validated ODE model of the CMV IE86 negative feedback circuit[22, 24] modified to include state variables for free crs DNA oligomers (C-DOTs) and the IE86-C-DOT bound complex (BC) was used:

$$\frac{d[IE86]}{dt} = \alpha_0 + \frac{\alpha_1 k_1^{h_1}}{[IE86]^{h_1} + k_1^{h_1}} + \qquad \text{eq. 1}$$
$$h_1 k_2 [BC] - h_1 k_{-2} [IE86]^{h_1} [CDOT] - \gamma_1 [IE86]$$

$$\frac{d[CDOT]}{dt} = k_2 [BC] - k_{-2} [IE86]^{h_1} [CDOT] \qquad \text{eq. 2}$$

$$\frac{d[BC]}{dt} = k_{-2} [IE86]^{h_1} [CDOT] - k_2 [BC] \qquad \text{eq. 3}$$

where $a_0$ represents the basal IE86 expression rate (2 unit/hr), $a_1$ represents the IE86 negative-feedback gain constant (10 unit/hr), $h_1$ represents the IE86 cooperativity index (hill coefficient), $k_1$ represents a Michaelis constant (set to 1) for IE86 feedback, $\gamma_1$ represents the per-capita IE86 protein degradation rate (0.23 hr-1), $k_2$ represents the BC dissociation rate (2 hr-1), and $k_{-2}$ represents the BC association rate (1 unit-$\eta$1*hr-1). In this model, the IE86 can oligomerize ($h_1$ ~6) 22 to bind either the ers in its own promoter (MIEP)—thereby mediating negative feedback and down-regulating its own expression rate—or can bind the crs in C-DOT DNA oligo, thereby sequestering IE86 that might otherwise downregulate its own expression via negative feedback. For both binding events, IE86 can transition between free and oligobound states but the negative feedback bound state is not explicitly modeled for parsimony and to not introduce unnecessary parameters. The DNA oligonucleotides were assumed to be stable (i.e., not degrade) over the course of the simulation time (validated below). For FIG. 11, the initial levels of C-DOT at time=0 were varied as indicated, all other initial conditions were zero. The ODEs were numerically solved using Matlab™

For calculations of the time to emergence of escape mutants, an analytic approach[7] previously used to calculate fitness differences between viral strains in patients and the time to emergence of GCV-resistant mutants was utilized. Briefly, the equation $$s = \frac{1}{t} \ln \left[ \frac{q(t) p_0}{p(t) q_0} \right]$$

describes the relative fitness, s, of the population and assumes replication occurs in continuous time. The time dynamics of the proportions of most and least fit viral variants (p and q), can be calculated given initial $p_0$, $q_0$, and s, (measured at 5.6% for GCV-resistant virus?. The mutant arisal time (defined as the time when p(t)=q(t)) can be calculated by algebraic rearrangement $$t_{mut} = \frac{1}{s} \ln \left[ \frac{1 - \mu}{\mu} \right].$$

The $\mu$ value for TK[8] generates a $I_{mma}$ ~100 days as observed in the clinic?. To predict the time to arisal for a putative C-DOT mutant that has only two single-point mutations (one in IE86 and one in the MIEP region), $$t_{mut} = \frac{1}{s} \ln \left[ \frac{1 - \mu^2}{\mu^3} \right],$$

where u for IE86 and the MIEP region are taken from[9]. The further maximally conservative assumption is made that s for C-DOT escape mutants is the same as for TK-escape mutants (in reality, s for C-DOT mutants is far lower as it must account for the single mutants that have a 100-fold fitness cost both in presence and absence of C-DOTs).

Protein Expression, EMSA and DNA Binding Assays

BL21 competent *E. Coli* cells (New England Biolabs Inc) were transformed with a pMALcXS plasmid encoding the C-terminus part of IE86 fused to the maltose binding protein, as described[36], and induced with isopropyl b-D thiogalactoside (IPTG) in 1L luria broth (Thermofisher Scientific) containing ampicillin (Sigma-Aldrich). Cells were pelleted at 10,000 RPM for 30 minutes at 4° C. and resuspended in 40 mL lysis buffer (20 mM HEPES, pH 7.4, 1M NaCl, 1 mM EDTA, 1 mM DTT, Roche protease inhibitor cocktail). Lysozyme was added at a final concentration of 1 mg/ml and cells were incubated on ice for 30 minutes, followed by addition of 1 mM PMSF and sonication on ice (sonicator at 40% amplitude, 10 seconds on, 30 seconds off-6 repeats). 1 mM $MgSO_4$, 0.1 mg/ml DNAse (Sigma-Aldrich, St Louis, MO) and 25 U/ml Benzonase (Sigma-Aldrich) were then added, cells further incubated on ice for 15-30 minutes, centrifuged at 12,000 rpm for 30 minutes at 4° C. and the supernatant incubated with amylose resins (Sigma-Aldrich, St Louis, MO) for 2 hours at 4° C. with gentle agitation. Batch bound resin was poured into a column and washed with 10 column volumes of lysis buffer, and eluted in elution buffer (20 mM HEPES, pH 7.4° C., 250 mM NaCl, 10 mM Maltose, 1 mM EDTA and 1 mM DTT). The eluted protein was passed through a Superose 6 column (GE Healthcare Life Sciences) using gel filtration buffer (20 mM HEPES, pH 7.4, 250 mM NaCl and 1 mM DTT) and used for EMSA or for binding assays. Briefly, digoxygenin labeled oligo probe was made using sequences for crs and Δcrs (see Table 1) as described previously[36]. Binding assays were performed by incubating dsDNA oligonucleotides of various lengths with purified MBP-IE86 for 30 minutes at room temperature and running on Superpose-6 column in the presence of gel filtration buffer and monitored oligomerized form of MBP-IE86 (at 13 ml column volume on FPLC) in the presence of different sizes of C-DOT$^C$. To verify the sequence specific interaction between ers and MBP-IE86, EMSAs were performed using the DIG gel-shift kit, $2^{nd}$ generation (Sigma-Aldrich) according to the manufacturer's instructions. DNA oligonucleotides were obtained from Integrated DNA Technologies (San Jose, CA) (see Table 1 for sequences) and resuspended in annealing buffer (100 mM Potassium acetate; 30 mM HEPES, pH 7.5). Oligonucleotides of complimentary sequences were mixed in equimolar amount, heated to 95° C. for 2 minutes, and gradually cooled to 25° C. over 45 minutes in a S1000 Thermocycler (Bio-Rad) and stored at −20° C.

Cell-Culture Conditions and Flow Cytometry

ARPE-19 cells were maintained in a 1:1 mixture of Dulbecco's Modified Eagle's Medium (DMEM)/F-12 (Mediatech Inc.) with 10% fetal bovine serum (FBS) (HyClone) and 50 U/ml Penicillin-Streptomycin (Mediatech Inc.) at 37° C. and 5% $CO_2$ in a humified incubator. MRC-5 fibroblasts, NIH 3T3 mouse fibroblast and Telo-RF were maintained in DMEM with 10% FBS and SOU/ml Penicillin and Streptomycin (Mediatech Inc.). Fomivirsen (NIH), Ganciclovir and Acyclovir (Sigma-Aldrich, St Louis, MO) were added to media at the indicated concentrations following virus inoculate removal. The ARPE-19 stably expressing the MIEP-IE86-GFP minimal circuit were previously described[22]. ARPE-19, Telo-RF (telomerase life extended rhesus fibroblast), NIH 3T3 mouse fibroblast and MRC-5 cell lines were obtained from ATCC. Flow cytometry was performed on BD FACS-Calibur (BD, Biosciences) at the Gladstone flow cytomtery core and analyzed suing FlowJo™ (FlowJo, LLC).

Western Blot Analysis $10^6$ ARPE-19 cells were centrifuged at 2,000 g for 10 min at 4° C. and resuspended in PBS (Sigma-Aldrich, St Louis, MO). Cells were pelleted, resuspended in ice-cold RIPA lysis buffer (Sigma-Aldrich, St Louis, MO) by vortexing and incubated at 4° C. for 30 min. The lysed samples were then pelleted at 13,000 rpm for 20 min at 4° C. and supernatants were assayed by western blot as previously described[24]. Briefly, 20 μg of cell lysate total protein was added to 1× loading buffer (100 mM Tris-HCl (pH6.8), 200 mM DTT, 4% SDS, 0.1% Bromophenol blue, 20% glycerol), and boiled for 10 minutes at 95° C. The lysed samples and precision plus kaleidoscope prestained protein marker (Bio-Rad) were then loaded on 10% Mini-PROTEAN TGX precast protein gel (Bio-Rad) in duplicate and ran at 90V for 2 hours in Tris-glycine running buffer (925 mM Tris, 250 mM Glycine and 0.1% SDS). One gel was stained for two hours at room temperature with coomassie blue stain (1 g coomassie brilliant blue (Bio-Rad), Methanol (50% [v/v]), Glacial acetic acid (10% [v/v]), final volume to IL with Milli-Q $H_2O$, followed by destaining (40% methanol, 7% acetic acid in final volume of IL in Milli-Q $H_2O$. The gel was blotted on a PVDF membrane using a semi-dry transfer unit (Trans-Blot Semi-Dry Electrophotetic transfer cell, Bio-Rad) at 25V for 45 minutes. The membrane was blocked with Li-Cor Odyssey™ blocking buffer for 2 hours at room temperature with gentle agitation. IE86 protein was detected by a 2-hour incubation of the membrane with an anti-IE86 antibody (1:100 dilution, Mab 810, Chemicon) in Li-Cor Odyssey™ blocking buffer at room temperature followed by 3 5-minute wash steps (1× PBS+0.01% Tween-20). The membrane was then incubated with a secondary Li-Cor detection antibody (1:20,000 dilution, goat anti-mouse 800CW) for 1 hour in the dark, washed three times in wash buffer (1×PBS+0.01% Tween-20) and imaged on an Odyssey system (Li-Cor).

Viral Replication Kinetics

The CMV TB40E-IE86-YFP virus was previously described[24] and CMV AD169, GDGIK17, CMV GDGrP53, CMV 759rD100-1, CMV PFArD100 were obtained through the NIH AIDS Reagent Program. MCMV strain K18137 was kindly provided by Lewis Lanier (UCSF) and Rhesus CMV 68.1 EGFP virus[38] was kindly provided by Peter Barry, UC-Davis. The clinical strain of HSV-1 17syn+IE175-YFP[39] was kindly provided by Roger Everett, MRC Virology Unit, Glasgow, Scotland that was passaged originally from a clinical isolate[40]. $1×10^6$ ARPE-19 cells were nucleofected with C-DOT$^C$, C-DOT$^H$ or C-DOT$^{Scram}$ using Amaxa nucleofector (Lonza). 24 hours post-nucleofection cells were infected in triplicate with 0.1 MOI of CMV (TB40E IE86-YFP) or HSV-1 (17syn+IE175-YFP). Four days post infection, cells were harvested and subjected to three freeze-thaw cycles and used for 10-fold serial dilution titration on naïve ARPE-19 cells. As similar protocol was used to nucleofect MRC-5 cells prior to infection with AD169 and titration on naïve MRC-5 cells. Titration results were converted to PFU/ml using median tissue culture infectious dose (TCID50) 41. Similarly, corneal tissues were dissociated using collagenase I (Sigma-Aldrich, St Louis, MO) for 30 minutes, subjected to three freeze-thaw cycles and used for TCID50 analysis.

qPCR, Flow Cytometry and Fluorescent Microscopy

Genomic DNA from CMV or HSV-1 infected ARPE-19 cells or mouse corneal tissue dissociated with collagenase I for 30 minutes was extracted using DNeasy Blood and tissue kit (Qiagen). TLR9 expression analysis was performed by total cell RNA extraction using an RNEASY RNA isolation kit (74104; QIAGEN) and reverse transcription using a QuantiTet Reverse Transcription kit (205311; QIAGEN). Relative quantification of genomic DNA or cDNA was performed on a 7900HT Fast Real-Time PCR System (ThermoFisher Scientific, 4329003) using sequence specific primers (Table 1) and Fast SYBR Green Master Mix (Applied Biosystems, 4385612). To measure the mean fluorescent intensity of YFP, flow cytometry was performed on trypsinized cells using BD FACS Calibur (BD Biosciences). Fluorescent microscopy of the cornea infected with HSV-1 was performed using Leica Zeiss fluorescent microscope for DAPI (excitation at 345 nm) and YFP (excitation at 514 nm). Images were analyzed using Image J software at threshold 100 for DAPI and YFP mask images, followed by particle analysis at size 2 micron^2 for YFP and 10 micron^2 for DAPI.

Corneal Infection Assays in Mice

All experiments were performed with 6- to 10-week old male and female sibling Black 6 mice. Breeding pairs were purchased from Jackson laboratories (Bar Harbor, Maine) and maintained under pathogen-free conditions in the UCSF barrier facility. All animal experiments were conducted in accordance with procedures approved by the UCSF Institutional Animal Care and Use Committee. Corneal epithelial debridement was performed on mice as previously described[42]. Briefly, mice were anesthetized by isofluorane inhalation (Abbott Laboratories, Alameda, CA). The central part of the epithelium was removed down to the basement membrane using an Algerbrush II (Katena Products, Inc., Denville, NJ). 5ul of HSV-1 17syn+YFP-IE175 ($10^5$ pfu) were immediately applied to the debrided cornea. 6 h later, mice were anesthetized again and 5 μl of C-DOT$^H$, C-DOT$^{Scram}$ or PBS were applied to the cornea for 5 min. At the indicated time post infection, eyes were enucleated and the corneas were dissected to remove the lens, iris, and retina. Four incisions were made equal distances apart to aid in flattening the corneas. Fresh corneas were counterstained using 0.5 μg/ml DAPI, mounted on slides with Fluoro-gel (Electron Microscopy Sciences, Hatfield, PA) and imaged using Leica Zeiss Confocal microscopy. Corneas were dissociated using collagenase I (Sigma-Aldrich, St Louis, MO), total DNA was extracted using DNeasy Blood & Tissue kit (QIAGEN), and subjected to qPCR using Fast SYBR green master mix (4385612; Applied Biosystems), analyzed on a 7900HT Fast Real-Time PCR System (4329003; Thermofisher Scientific). Virus titer was determined as described above.

Statistical Analysis

Statistical differences were determined by using the two-tailed unpaired Student's/test (GraphPad Prism, La Jolla, CA). A p-value less than 0.05 was considered statistically significant: *<0.05, <0.01, *<0.001, ****<0.0001, ns: not significant.

Oligonucleotide Preparation, Modification, and Nanoparticle Construction

C-DOT$^C$, C-DOT$^H$, C-DOT$^{MCMV}$, C-DOT$^{RhCMV}$, cy3-C-DOT$^C$ were made by annealing sequence specific oligonucleotides (see Table 1 for sequences). Briefly, DNA oligonucleotides were obtained from Integrated DNA Technologies (San Jose, CA) and resuspended in annealing buffer (100 mM Potassium acetate; 30 mM HEPES, pH 7.5). Oligonucleotides of complimentary sequences were mixed in equimolar amount, heated to 95° C. for 2 minutes, and gradually cooled to 25° C. over the period of 45 minutes in a S1000 Thermocycler (Bio-Rad) and stored at −20° C. Spherical nucleic acids (cy3-C-DOT$^C$-SNA) were made using 3' thiol labeled C-DOT$^C$ forward strand and 5' cyanine 3-phosphoramidite (cy3) tagged reverse strand oligo obtained from Bioneer, Inc (Alameda, CA) (see Table 1 for sequences). Oligonucleotides were annealed as mentioned above and cy3-C-DOT-SNA were made as described previously[43]. Briefly, annealed oligonucleotides were added to 10 nm citrate stabilized gold nanoparticle (Sigma-Aldrich, St Louis, MO) (~3nmol oligonucleotide per 1 ml of 10 nM colloid). After 20 minutes, 10% SDS (Sigma-Aldrich, St Louis, MO) was added to bring down the concentration of SDS to 0.1% in phosphate buffer (0.01M, pH 7.4). 2.0M NaCl was then added to bring salt concentration to 0.1M. Oligonucleotides were incubated under shaking conditions at room temperature for 30 min, followed by two successive additions of 2.0M NaCl at 30-minute interval to bring the final concentration of NaCl to 0.3M. The final mixture was incubated under shaking conditions to complete the functionalization of oligonucleotides on gold nanoparticles. The cy3-C-DOT-SNA was recovered by three centrifugation steps (13,000 rpm, 20 minutes), resuspended in 1×PBS buffer and stored at 4° C. until used.

TABLE 1

List of oligonucleotides and primers used in the study

| Name | Sequence |
|---|---|
| crs | Fw: TAATACGACTCACTATAG GGCGAATTGGAGCTCGTTTAGT GAACCGTCAGATCTCTAGAAGC TT (SEQ ID NO: 12) Rw: AAGCTTCTAGAGATCTGA CGGTTCACTAAACGAGCTCCAA TTCGCCCTATAGTGAGTCGTAT TA (SEQ ID NO: 13) |
| Dcrs | Fw: TAATACGACTCACTATAG GGCGAATTGGAGCTCGGCAGGC ATGCAAGCTT (SEQ ID NO: 14) Rw: AAGCTTGCATGCCTGCCG AGCTCCAATTCGCCCTATAGTG AGTCGTATTA (SEQ ID NO: 15) |
| 21 bp DNA | Fw: AGATCGTTTAGTGAACCG TAC (SEQ ID NO: 16) Rw: GTACGGTTCACTAAACGA TCT (SEQ ID NO: 17) |
| 28 bp DNA | Fw: GACAGATCGTTTAGTGAA CCGTACACGA (SEQ ID NO: 1) Rw: TCGTGTACGGTTCACTAA ACGATCTGTC (SEQ ID NO: 18) |
| 28 bp Scramble | Fw: ATACCGCGTAACCAGAGG TATATAGGTC (SEQ ID NO: 19) Rw: GACCTATATACCTCTGGT TACGCGGTAT (SEQ ID NO: 20) |
| 34 bp DNA | Fw: CGTTTAGTGAACCGCGCG CGATAGTACATAATCA (SEQ ID NO: 21) Rw: TGATTATGTACTATCGCG CGCGGTTCACTAAACG (SEQ ID NO: 22) |
| 64 bp DNA | Fw: TAATACGACTCACTATAGGGC GAATTGGAGCTCGTTTAGTGA ACCGTCAGATCTCTAGAAGC TT (SEQ ID NO: 12) Rw: AAGCTTCTAGAGATCT GACGGTTCACTAAACGAGCT CCAATTCGCCCTATAGTGAG TCGTATTA (SEQ ID NO: 13) |
| C-DOT$^C$ | Fw: G*ACAGATCGTT*TAG TGAACC*GTACACG*A (SEQ ID NO: 5) Rw: T*CGTGTAC*GGTTCA CTA*AACGATCTGT*C (SEQ ID NO: 39) |
| C-DOT$^{Scram}$ | Fw: A*TACCGCGTAA*CCA GAGGT*ATATAGGT*C (SEQ ID NO: 40) Rw: G*ACCTATAT*ACCTC TGG*TTACGCGGTA*T (SEQ ID NO: 41) |

| 33 | | 34 |
|---|---|---|

TABLE 1-continued

List of oligonucleotides and
primers used in the study

| Name | Sequence |
|---|---|
| C-DOT$^{RhCMV}$ | Fw: G*ACAGATCGT*TTAG GGA AC*CGTACACG*A (SEQ TD NO: 8) Rw: T*CGTGTACG*GTTCC CTAA*ACGATCTGT*C (SEQ ID NO: 43) |
| c-DOT$^{MCMV}$ | Fw: G*ACAGACCA*GCGTC GG*TACCGTACACG*A (SEQ ID NO: 9) Rw: T*CGTGTACGGT*ACC GACGC*TGGTCTGT*C (SEQ ID NO: 42) |
| cy3-C-DOTC | Fw: /5Cy3/GACAGATCGT TTAGTGAACCGTACACGA (SEQ ID NO: 23) Rw: TCGTGTACGGTTCACT AAACGATCTGTC (SEQ ID NO: 18) |
| C-DOT$^C$ (1×) Concat | Fw: CGTTTAGTGAACCGCG CGCGATAGTACATAATCA (SEQ ID NO: 21) Rw: TGATTATGTACTATCG CGCGCGGTTCACTAAACG (SEQ ID NO: 22) |
| C-DOT$^C$ (2×) Concat | Fw: CGTTTAGTGAACCGCGC GCGCGTTTAGTGAACCG (SEQ ID NO: 24) Rw: CGGTTCACTAAACGCGC GCGCGGTTCACTAAACG (SEQ ID NO: 25) |
| C-DOT$^H$ | Fw: CCG*AGGAC*GCCCCGA TC*GTCCACACG*GAG (SEQ ID NO: 11) Rw: CTC*CGTGTGGAC*GAT CGGGGC*GTCCT*CGG (SEQ ID NO: 26) |
| cy3-C-DOT$^H$ | Fw: /5Cy3/CCG*AGGAC*G CCCCGATC*GTCCACACG*GA G (SEQ ID NO: 44) Rw: CTC*CGTGTGGAC*GAT CGGGGC*GTCCT*CGG (SEQ ID NO: 26) |
| ODN 2216 FW | Fw: GGGGGACGATCGTCGGG GGG (SEQ ID NO: 27) Rw: CCCCCCGACGATCGTCC CCC (SEQ ID NO: 28) |
| TLR9-qPCR | Fw: CCGTGACAATTACCTGG CCTTC (SEQ ID NO: 29) Rw: CAGGGCCTTCAGCTGGT TTC (SEQ ID NO: 30) |
| MIEP 250 bp crs | Fw: TTCCTACTTGGCAGTAC ATCTAC (SEQ ID NO: 31) Rw: CCTATAGGCTAAGCTAT ACCATC (SEQ ID NO: 32) |
| IE86 Exon 5 | Fw: TGACATCCTCGCCCAGG (SEQ ID NO: 33) Rw: TTACTGAGACTTGTTCC TCAGGT (SEQ ID NO: 34) |
| IE86-qPCR | Fw: TGACCGAGGATTGCAAC GA (SEQ ID NO: 35) |

TABLE 1-continued

List of oligonucleotides and
primers used in the study

| Name | Sequence |
|---|---|
| | Rw: CGGCATGATTGACAGCC TG (SEQ ID NO: 36) |
| IE175-qPCR | Fw: CCTATAGGCTAAGCTAT ACCATC (SEQ ID NO: 32) Rw: GTCTGACGGTCTGTCTC TGG (SEQ ID NO: 37) |
| GAPDH-qPCR | Fw: GTCTGACGGTCTGTCTC TGG (SEQ ID NO: 37) Rw: CAAGAAGATGCGGCTGT CTC (SEQ ID NO: 38) |

* Phosphorothioate bond

\* Phosphorothioate bond

REFERENCES

1 Meylan, S., Andrews, I. W. & Collins, J. J. Targeting Antibiotic Tolerance, Pathogen by Pathogen. Cell 172, 1228-1238, doi: 10.1016/j.cell.2018.01.037 (2018).

2 Lee, H. H., Molla, M. N., Cantor, C. R. & Collins, J. J. Bacterial charity work leads to population-wide resistance. Nature 467, 82-85, doi: 10.1038/nature09354 (2010).

3 Goldberg, D. E., Siliciano, R. F. & Jacobs, W. R., Jr. Outwitting evolution: fighting drug-resistant TB, malaria, and HIV. Cell 148, 1271-1283, doi: 10.1016/j.cell.2012.02.021 S0092-8674 (12) 00221-8 [pii] (2012).

4 Piret, J. & Boivin, G. Antiviral drug resistance in herpesviruses other than cytomegalovirus. Rev Med Virol 24, 186-218, doi: 10.1002/rmv.1787 (2014).

5. Lurain, N. S. & Chou, S. Antiviral drug resistance of human cytomegalovirus. Clin Microbiol Rev 23, 689-712, doi: 10.1128/CMR.00009-10 23/4/689 [pii] (2010).

6 Frobert. E. et al. Resistance of herpes simplex viruses to acyclovir: an update from a ten-year survey in France. Antiviral Res 111, 36-41, doi: 10.1016/j.antiviral.2014.08.013 (2014).

7 Emery, V. C. & Griffiths, P. D. Prediction of cytomegalovirus load and resistance patterns after antiviral chemotherapy. Proc Natl Acad Sci USA 97, 8039-8044, doi: 10.1073/pnas. 140123497 (2000).

8 Perelson, A. S. Modelling viral and immune system dynamics. Nat Rev Immunol 2, 28-36, doi: 10.1038/nri700 (2002).

9 Coffin, J. M. HIV population dynamics in vivo: implications for genetic variation, pathogenesis, and therapy. Science 267, 483-489 (1995).

10. Lu, Q., Hwang, Y. T. & Hwang, C. B. Mutation spectra of herpes simplex virus type 1 thymidine kinase mutants. J Virol 76, 5822-5828 (2002).

11 Renzette, N., Bhattacharjce, B., Jensen, J. D., Gibson, L. & Kowalik, T. F. Extensive genome-wide variability of human cytomegalovirus in congenitally infected infants. PLOS Pathog 7, e1001344, doi: 10.1371/journal.ppat. 1001344 (2011).

12 Coen, D. M. & Schaffer, P. A. Two distinct loci confer resistance to acycloguanosine in herpes simplex virus type 1. Proc Natl Acad Sci USA 77, 2265-2269 (1980).

13 Goldner, T. et al. The novel anticytomegalovirus compound AIC246 (Letermovir) inhibits human cytomegalovirus replication through a specific antiviral mechanism that involves the viral terminase. *J Virol* 85, 10884-10893, doi: 10.1128/JVI.05265-11 (2011).

14 Jaishankar, D. et al. An off-target effect of BX795 blocks herpes simplex virus type 1 infection of the eye. *Sci Transl Med* 10, doi: 10.1126/scitranslmed.aan5861 (2018).

15. Pai, A. & Weinberger, L. S. Fate-Regulating Circuits in Viruses: From Discovery to New Therapy Targets. *Annu Rev Virol* 4, 469-490, doi: 10.1146/annurev-virology-110615-035606 (2017)

16 Enquist, L. W. & Leib, D. A. Intrinsic and Innate Defenses of Neurons: Detente with the Herpesviruses. *J Virol* 91, doi: 10.1128/JVI.01200-16 (2017).

17 Weller, S. K. & Coen, D. M. Herpes simplex viruses: mechanisms of DNA replication. *Cold Spring Harb Perspect Biol* 4, a013011, doi: 10.1101/cshperspect.a013011 (2012).

18 Shenk. T. E. & Stinski, M. F. Human cytomegalovirus. Preface. *Curr Top Microbiol Immunol* 325, v (2008).

19 Mocarski, E. S., Shenk, T. & Pass, R. F. in *Fields' virology* (ed David M. Knipe) 2708-2772 (Lippincott Williams & Wilkins, 2006).

20 Liu, B., Hermiston, T. W. & Stinski, M. F. A cis-acting element in the major immediate-early (IE) promoter of human cytomegalovirus is required for negative regulation by IE2. *J Virol* 65, 897-903 (1991).

21 Paterson, T. & Everett, R. D. The regions of the herpes simplex virus type 1 immediate early protein Vmw 175 required for site specific DNA binding closely correspond to those involved in transcriptional regulation. *Nucleic Acids Res* 16, 11005-11025 (1988).

22 Teng. M. W. et al. An endogenous accelerator for viral gene expression confers a fitness advantage. *Cell* 151, 1569-1580, doi: 10.1016/j.cell.2012.11.051 (2012).

23 Isomura, H. et al. A cis element between the TATA Box and the transcription start site of the major immediate-early promoter of human cytomegalovirus determines efficiency of viral replication. *J Virol* 82, 849-858, doi: 10.1128/JVI.01593-07 (2008).

24 Vardi, N., Chaturvedi, S. & Weinberger, L. S. Feedback-mediated signal conversion promotes viral fitness. *Proc Natl Acad Sci USA* 115, E8803-E8810, doi: 10.1073/pnas.1802905115 (2018).

25 Everett, R. D., Murray, J., Orr, A. & Preston, C. M. Herpes simplex virus type 1 genomes are associated with ND10 nuclear substructures in quiescently infected human fibroblasts. *J Virol* 81, 10991-11004, doi: 10.1128/JVI.00705-07 (2007).

26 Asberg, A. et al. Lessons Learned From a Randomized Study of Oral Valganciclovir Versus Parenteral Ganciclovir Treatment of Cytomegalovirus Disease in Solid Organ Transplant Recipients: The VICTOR Trial. *Clin Infect Dis* 62, 1154-1160, doi: 10.1093/cid/ciw084 (2016)

27 Luecke, S. et al. cGAS is activated by DNA in a length-dependent manner. *EMBO Rep* 18, 1707-1715, doi: 10.15252/embr.201744017 (2017).

28 Mulamba, G. B., Hu, A., Azad, R. F., Anderson, K. P. & Coen, D. M. Human cytomegalovirus mutant with sequence-dependent resistance to the phosphorothioate oligonucleotide fomivirsen (ISIS 2922). *Antimicrob Agents Chemother* 42, 971-973 (1998).

29 Lahmidi, S., Yousefi, M., Dridi, S., Duplay, P. & Pearson, A. Dok-1 and Dok-2 Are Required To Maintain Herpes Simplex Virus 1-Specific CD8 (+) T Cells in a Murine Model of Ocular Infection. *J Virol* 91, doi: 10.1128/JVI.02297-16 (2017).

30 Adams, D. et al. Patisiran, an RNAi Therapeutic, for Hereditary Transthyretin Amyloidosis. *N Engl J Med* 379, 11-21, doi: 10.1056/NEJMoal716153 (2018), 31 Kanasty, R., Dorkin, J. R., Vegas, A. & Anderson, D. Delivery materials for siRNA therapeutics. *Nat Mater* 12, 967-977, doi: 10.1038/nmat3765 (2013).

32 Khvorova, A. & Watts, J. K. The chemical evolution of oligonucleotide therapies of clinical utility. *Nat Biotechnol* 35, 238-248, doi: 10.1038/nbt.3765 (2017).

33 Cunningham, E. T. Cytomegalovirus: ophthalmic perspectives on a pervasive pathogen. *Expert Review of Ophthalmology* 6, 489-491, doi: 10.1586/eop. 11.50 (2011).

34 Elia, M. H., J.J., and Gaudio, P. A. in *EyeNet Magazine* 37-38 (2016).

35 Renzette, N. et al. Limits and patterns of cytomegalovirus genomic diversity in humans. *Proc Natl Acad Sci USA* 112, E4120-4128, doi: 10.1073/pnas.1501880112 1501880112 [pii] (2015).

36. M. P. Macias, M. F. Stinski, An in vitro system for human cytomegalovirus immediate early 2 protein (IE2)-mediated site-dependent repression of transcription and direct binding of IE2 to the major immediate early promoter. *Proc Natl Acad Sci USA* 90, 707-711 (1993).

37. P. J. Morley, P. Ertl, C. Sweet, Immunisation of Balb/c mice with severely attenuated murine cytomegalovirus mutants induces protective cellular and humoral immunity. *J Med Virol* 67, 187-199 (2002).

38. W. L. Chang, P. A. Barry, Cloning of the full-length rhesus cytomegalovirus genome as an infectious and self-excisable bacterial artificial chromosome for analysis of viral pathogenesis. *J Virol* 77, 5073-5083 (2003).

39. R. D. Everett, G. Sourvinos, A. Orr, Recruitment of herpes simplex virus type 1 transcriptional regulatory protein ICP4 into foci juxtaposed to ND10 in live, infected cells. *J Virol* 77, 3680-3689 (2003).

40. S. M. Brown, D. A. Ritchie, J. H. Subak-Sharpe, Genetic studies with herpes simplex virus type 1. The isolation of temperature-sensitive mutants, their arrangement into complementation groups and recombination analysis leading to a linkage map. *J Gen Virol* 18, 329-346 (1973).

41. L. J. Reed, & Muench, H., A simple method of estimating fifty percent endpoints. *Am. J. Hygiene* 27, 493-497 (1938).

42. M. F. Chan, Z. Werb, Animal Models of Corneal Injury. *Bio Protoc* 5, e1516 (2015).

43. N. L. Rosi et al., Oligonucleotide-modified gold nanoparticles for intracellular gene regulation. *Science* 312, 1027-1030 (2006).

44. M. K. Skouboe et al., STING agonists enable antiviral cross-talk between human cells and confer protection against genital herpes in mice. *PLOS Pathog* 14, e1006976 (2018).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising a double stranded DNA molecule comprising a cis regulatory sequence (crs) of the herpesvirus, wherein the crs is flanked on the 5' end by a first sequence of at least 2 base pairs and on the 3' end by a second sequence of at least 2 base pairs, wherein the herpesvirus is HCMV and the sequence of the herpesvirus crs comprises CGTTTAGTGAACCG (SEQ ID NO: 4), wherein the sequence of the herpesvirus crs flanked on the 5' end by a first sequence of at least 2 base pairs and on the 3' end by a second sequence of at least 2 base pairs comprises GACAGATCGTTTAGTGAACCGTACACGA (SEQ ID NO: 1).

2. The composition of claim 1, wherein the crs is flanked on the 5' end by a first sequence of at least 7 base pairs and on the 3' end by a second sequence of at least 7 base pairs.

3. A method for inhibiting replication of a herpesvirus in a cell infected with a herpesvirus, the method comprising contacting the cell with the composition of claim 1.

4. The method of claim 3, wherein the crs is flanked on the 5' end by a first sequence of at least 7 base pairs and on the 3' end by a second sequence of at least 7 base pairs.

5. The method of claim 3, wherein the sequence of the herpesvirus crs flanked on the 5' end by a first sequence of at least 2 base pairs and on the 3' end by a second sequence of at least 2 base pairs comprises G*ACAGATCGTT*TAGTGAACC*GTACACG*A (SEQ ID NO: 5), wherein * is a phosphorothioated bond.

6. A method of treating a herpesvirus infection in an individual, the method comprising administering to the individual an effective amount of the composition of claim 1.

7. The method of claim 6, wherein the ers is flanked on the 5' end by a first sequence of at least 7 base pairs and on the 3' end by a second sequence of at least 7 base pairs.

8. The method of claim 6, wherein the sequence of the herpesvirus crs flanked on the 5' end by a first sequence of at least 2 base pairs and on the 3' end by a second sequence of at least 2 base pairs comprises G*ACAGATCGTT*TAGTGAACC*GTACACG*A (SEQ ID NO: 5), wherein * is a phosphorothioated bond.

9. A composition comprising a double stranded DNA molecule comprising a cis regulatory sequence (crs) of the herpesvirus, wherein the crs is flanked on the 5' end by a first sequence of at least 2 base pairs and on the 3' end by a second sequence of at least 2 base pairs, wherein the herpesvirus is HCMV and the sequence of the herpesvirus crs comprises CGTTTAGTGAACCG (SEQ ID NO: 4), wherein the sequence of the herpesvirus crs flanked on the 5' end by a first sequence of at least 2 base pairs and on the 3' end by a second sequence of at least 2 base pairs comprises G*ACAGATCGTT*TAGTGAACC*GTACACG*A (SEQ ID NO: 5), wherein * is a phosphorothioated bond.

10. The composition of claim 9, wherein the ers is flanked on the S' end by a first sequence of at least 7 base pairs and on the 3' end by a second sequence of at least 7 base pairs.

* * * * *